(12) United States Patent
Spoeth, Jr. et al.

(10) Patent No.: US 8,197,389 B2
(45) Date of Patent: Jun. 12, 2012

(54) EXERCISING APPARATUS

(75) Inventors: Carl R. Spoeth, Jr., Bayonet Point, FL (US); Jeffrey A. Pearson, Plymouth, MA (US); Jacob Fitzgerald, Boston, MA (US)

(73) Assignee: Michael G. Lannon, Orleans, MA (US)

(\*) Notice: Subject to any disclaimer, the term of this patent is extended or adjusted under 35 U.S.C. 154(b) by 0 days.

(21) Appl. No.: 12/814,948

(22) Filed: Jun. 14, 2010

(65) Prior Publication Data

US 2010/0292052 A1 Nov. 18, 2010

Related U.S. Application Data

(63) Continuation of application No. 11/811,524, filed on Jun. 11, 2007, now Pat. No. 7,771,319, which is a continuation-in-part of application No. 11/125,569, filed on May 10, 2005, now Pat. No. 8,105,207.

(60) Provisional application No. 60/662,935, filed on Mar. 16, 2005, provisional application No. 60/569,535, filed on May 10, 2004.

(51) Int. Cl.
*A63B 71/00* (2006.01)

(52) U.S. Cl. .................... 482/8; 482/9; 482/94

(58) Field of Classification Search ............... 482/4–5, 482/8, 93–94, 98–102, 901–902; 248/323, 248/580, 581, 248, 671, 917, 919–920

See application file for complete search history.

(56) References Cited

U.S. PATENT DOCUMENTS

| 3,735,101 A | 5/1973 | Stewart |
| 3,869,121 A | 3/1975 | Flavell |
| 4,158,511 A * | 6/1979 | Herbenar ...................... 403/113 |
| 4,493,485 A | 1/1985 | Jones |
| 4,549,555 A | 10/1985 | Fraser et al. |
| 4,728,099 A | 3/1988 | Pitre |
| 4,735,195 A | 4/1988 | Blum et al. |
| 4,746,113 A | 5/1988 | Kissel |
| 4,765,613 A * | 8/1988 | Voris ............................... 482/5 |
| 4,817,940 A | 4/1989 | Shaw et al. ...................... 482/9 |

(Continued)

FOREIGN PATENT DOCUMENTS

WO WO2010/019644 2/2010

OTHER PUBLICATIONS

U.S. Appl. No. 60/569,535, filed May 10, 2004, Lannon et al.

(Continued)

*Primary Examiner* — Glenn Richman
(74) *Attorney, Agent, or Firm* — Fish & Richardson P.C.

(57) ABSTRACT

An apparatus is disclosed for enabling an operator to exercise comprising a frame having a body, a base and a top. A load is positioned on the frame for providing a resistive force. A press is positioned on the frame for displacement by the operator. A linkage joins the load with the press for displacing the load upon displacement of the press by the operator. An arm extends between a support end and a user end. A support pivot secures the support end of the arm to the top of the frame for pivoting the arm about the frame. A user interface inputs and outputs data. A user pivot securing the user interface to the user end of the arm for pivoting the user interface about the arm.

27 Claims, 35 Drawing Sheets

U.S. PATENT DOCUMENTS

| | | | |
|---|---|---|---|
| 4,828,257 A | 5/1989 | Dyer et al. | |
| 4,831,242 A | 5/1989 | Englehardt et al. | 235/382 |
| 4,902,009 A | 2/1990 | Jones | |
| 4,907,795 A | 3/1990 | Shaw et al. | 482/9 |
| 4,911,427 A | 3/1990 | Matsumoto et al. | |
| 4,919,418 A | 4/1990 | Miller | 482/6 |
| 5,018,726 A | 5/1991 | Yorioka | |
| 5,020,794 A | 6/1991 | Englehardt et al. | |
| 5,020,795 A | 6/1991 | Airy et al. | |
| 5,037,089 A | 8/1991 | Spagnuolo et al. | 482/5 |
| 5,082,001 A | 1/1992 | Vannier et al. | |
| 5,149,084 A | 9/1992 | Dalebout et al. | |
| 5,216,817 A | 6/1993 | Misevich et al. | |
| 5,290,214 A | 3/1994 | Chen | 482/137 |
| 5,323,784 A | 6/1994 | Shu | |
| 5,324,247 A | 6/1994 | Lepley | |
| 5,328,429 A | 7/1994 | Potash et al. | |
| 5,410,472 A * | 4/1995 | Anderson | 482/9 |
| 5,429,140 A | 7/1995 | Burdea et al. | |
| 5,435,799 A | 7/1995 | Lundin | |
| 5,458,548 A | 10/1995 | Crossing et al. | |
| 5,603,330 A | 2/1997 | Suga | |
| 5,653,669 A * | 8/1997 | Cheng | 482/138 |
| 5,655,997 A | 8/1997 | Greenberg et al. | |
| 5,679,102 A | 10/1997 | Hammer | |
| 5,704,875 A | 1/1998 | Tanabe | |
| 5,715,160 A | 2/1998 | Plotke | |
| 5,740,813 A | 4/1998 | Ogata et al. | |
| 5,785,632 A | 7/1998 | Greenberg et al. | |
| 5,800,310 A | 9/1998 | Jones | |
| 5,803,870 A | 9/1998 | Buhler | |
| 5,810,747 A | 9/1998 | Brudny et al. | |
| 5,853,351 A | 12/1998 | Maruo et al. | |
| 5,879,270 A | 3/1999 | Huish et al. | |
| 5,916,063 A | 6/1999 | Alessandri | |
| 5,921,891 A | 7/1999 | Browne | |
| 5,931,763 A | 8/1999 | Alessandri | |
| 5,947,869 A | 9/1999 | Shea | |
| 5,980,429 A | 11/1999 | Nashner | |
| 6,013,009 A | 1/2000 | Karkanen | |
| 6,033,227 A | 3/2000 | Ishige | |
| 6,050,924 A | 4/2000 | Shea | |
| 6,053,844 A | 4/2000 | Clem | |
| 6,077,193 A | 6/2000 | Buhler et al. | |
| 6,117,049 A | 9/2000 | Lowe | |
| 6,190,287 B1 | 2/2001 | Nashner | |
| 6,210,301 B1 | 4/2001 | Abraham-Fuchs et al. | |
| 6,228,000 B1 | 5/2001 | Jones | |
| 6,231,481 B1 | 5/2001 | Brock | |
| 6,354,996 B1 | 3/2002 | Drinan et al. | |
| 6,358,188 B1 | 3/2002 | Ben-Yehuda et al. | |
| 6,439,893 B1 | 8/2002 | Byrd et al. | |
| 6,471,363 B1 * | 10/2002 | Howell et al. | 362/11 |
| 6,494,811 B1 | 12/2002 | Alessandri | |
| 6,497,638 B1 | 12/2002 | Shea | |
| 6,503,173 B2 | 1/2003 | Clem | |
| 6,527,674 B1 | 3/2003 | Clem | |
| 6,551,214 B1 * | 4/2003 | Taimela | 482/10 |
| 6,605,044 B2 | 8/2003 | Bimbaum | |
| 6,607,483 B1 | 8/2003 | Holland | |
| 6,626,799 B2 | 9/2003 | Watterson et al. | |
| 6,626,800 B1 | 9/2003 | Casler | |
| 6,626,805 B1 | 9/2003 | Lightbody | |
| 6,632,158 B1 | 10/2003 | Nashner | |
| 6,632,161 B1 | 10/2003 | Nir | |
| 6,648,798 B2 | 11/2003 | Yoo | |
| 6,659,946 B1 | 12/2003 | Batchelor et al. | |
| 6,669,600 B2 | 12/2003 | Warner | |
| 6,672,991 B2 | 1/2004 | O'Malley | |
| 6,687,535 B2 | 2/2004 | Hautala et al. | |
| 6,689,057 B1 | 2/2004 | Shinsel et al. | |
| 6,719,667 B2 | 4/2004 | Wong et al. | |
| 6,740,007 B2 | 5/2004 | Gordon et al. | |
| 6,746,370 B1 | 6/2004 | Fleming et al. | |
| 6,793,607 B2 | 9/2004 | Neil | |
| 6,808,472 B1 | 10/2004 | Hickman | |
| 6,863,641 B1 | 3/2005 | Brown et al. | |
| 6,866,613 B1 | 3/2005 | Brown et al. | |
| 6,899,442 B2 * | 5/2005 | Howell et al. | 362/147 |
| 6,913,559 B2 | 7/2005 | Smith | |
| 6,916,274 B2 | 7/2005 | Glusco | |
| 6,918,858 B2 | 7/2005 | Watterson et al. | |
| 6,921,351 B1 | 7/2005 | Hickman et al. | |
| 6,973,688 B2 * | 12/2005 | Barker et al. | 5/600 |
| 7,163,488 B2 * | 1/2007 | Anders et al. | 482/4 |
| 7,243,892 B2 * | 7/2007 | Pfister | 248/371 |
| 7,369,672 B2 * | 5/2008 | Hirschhorn | 381/333 |
| 7,410,138 B2 * | 8/2008 | Parsons | 248/278.1 |
| 2003/0235320 A1 * | 12/2003 | Hirschhorn | 381/333 |
| 2004/0171464 A1 | 9/2004 | Ashby et al. | |
| 2005/0041048 A1 * | 2/2005 | Hillman et al. | 345/905 |
| 2005/0239600 A1 * | 10/2005 | Liang et al. | 482/1 |
| 2007/0265138 A1 | 11/2007 | Ashby | |

OTHER PUBLICATIONS

U.S. Appl. No. 60/662,935, filed Mar. 16, 2005, Lannon et al.
PCT International Search Report and Written Opinion, PCT/US2009/053518, dated Feb. 22, 2010, 13 pages.

* cited by examiner

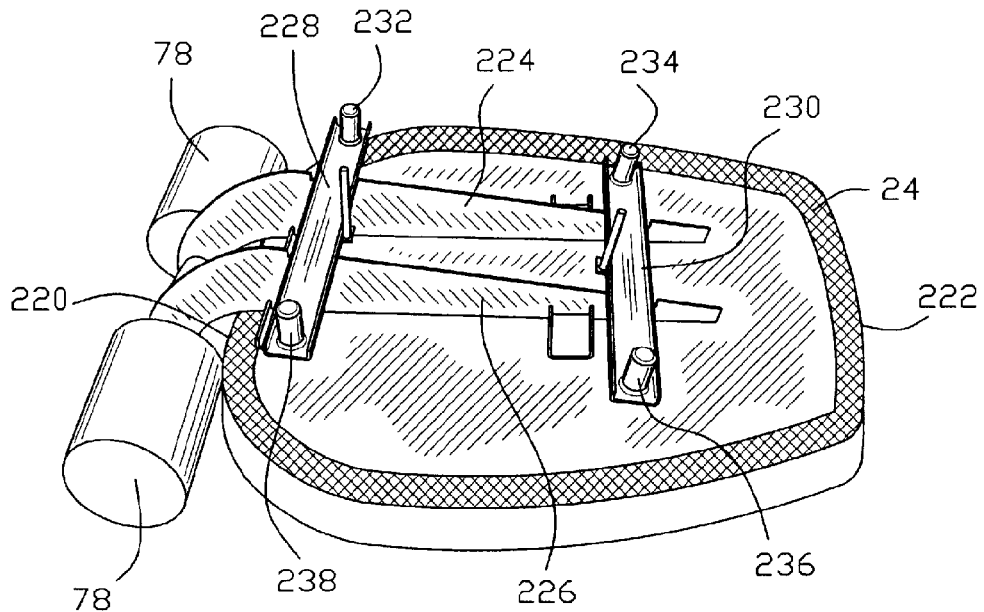
FIG. 17
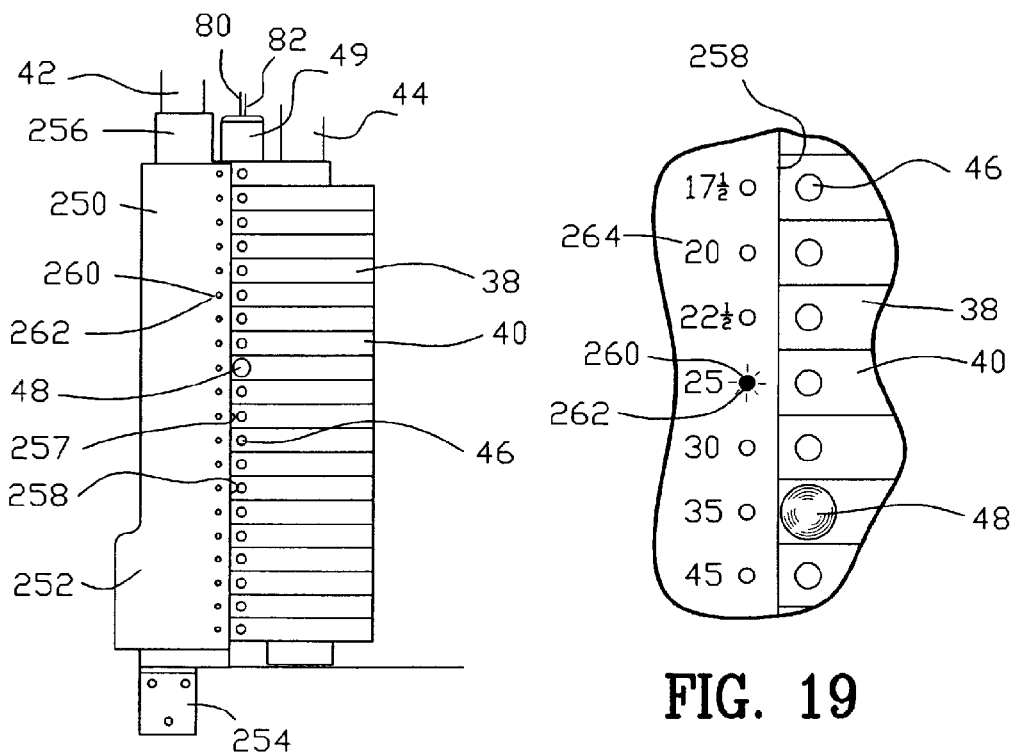
FIG. 18
FIG. 19

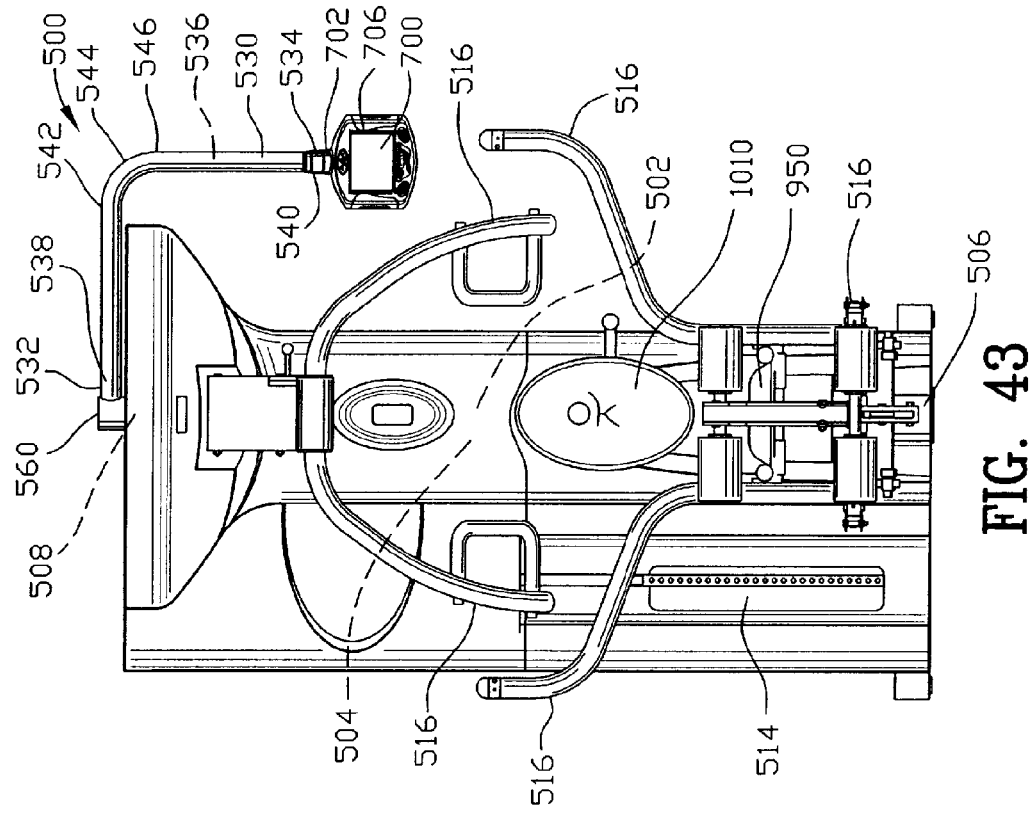

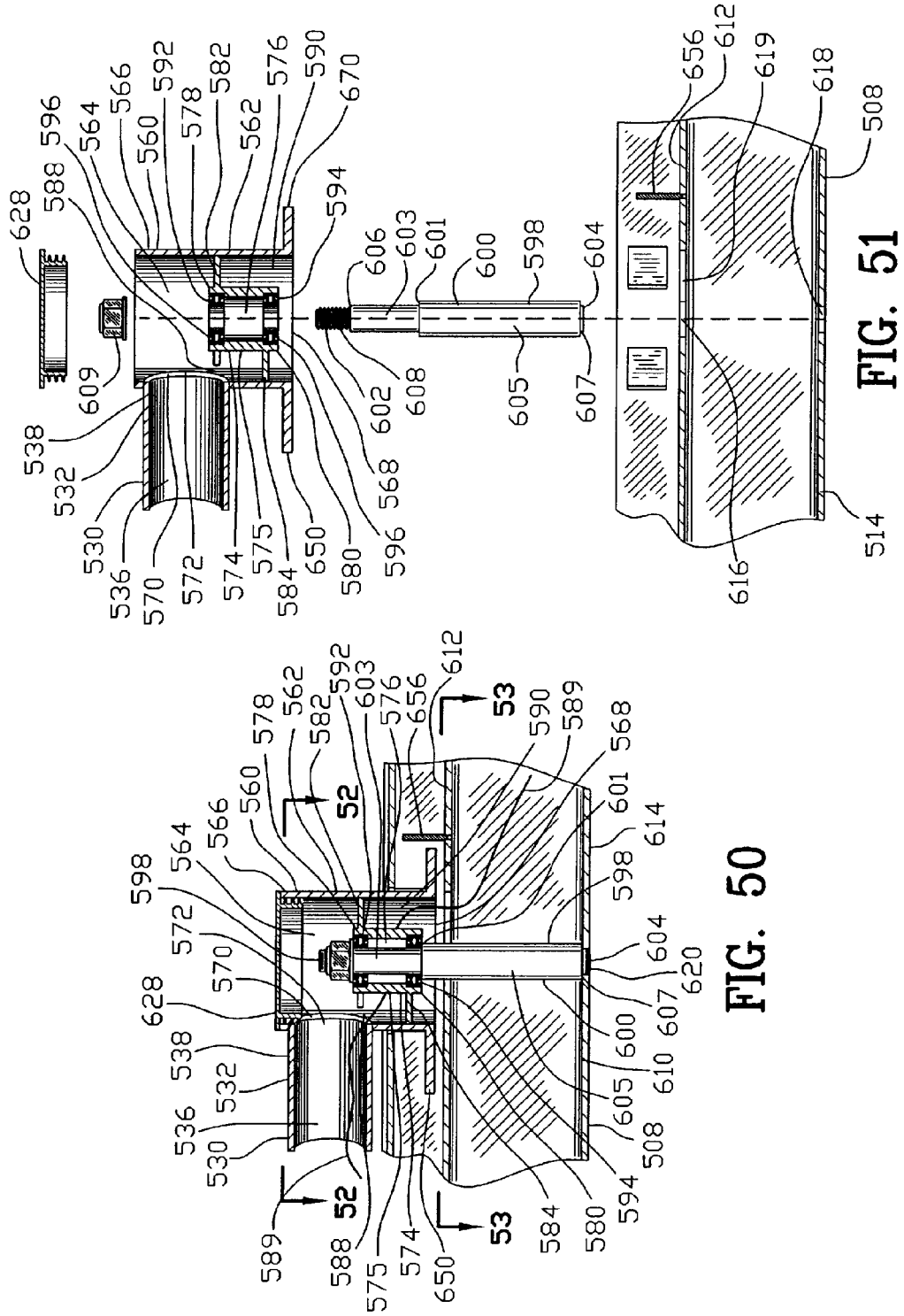

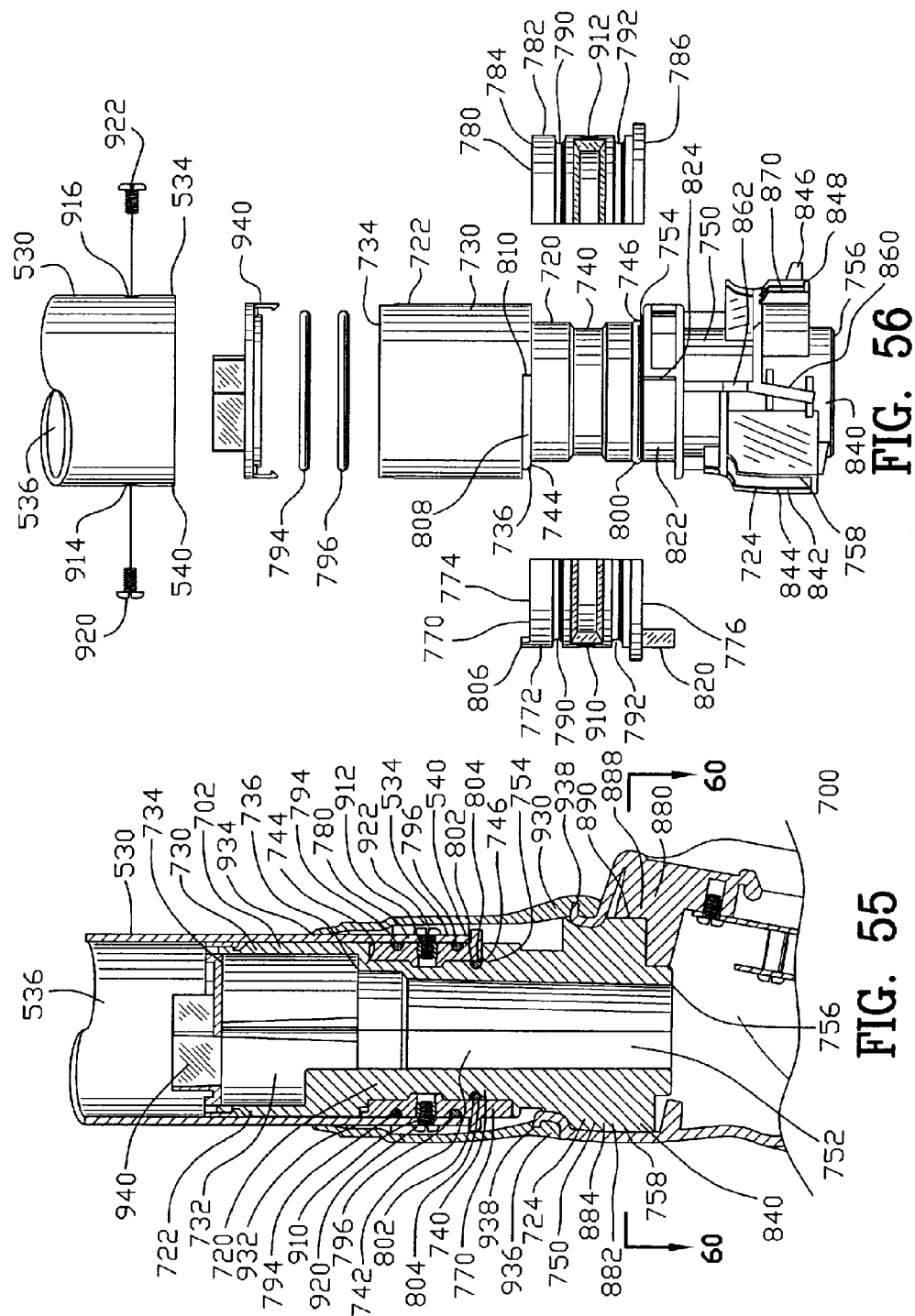

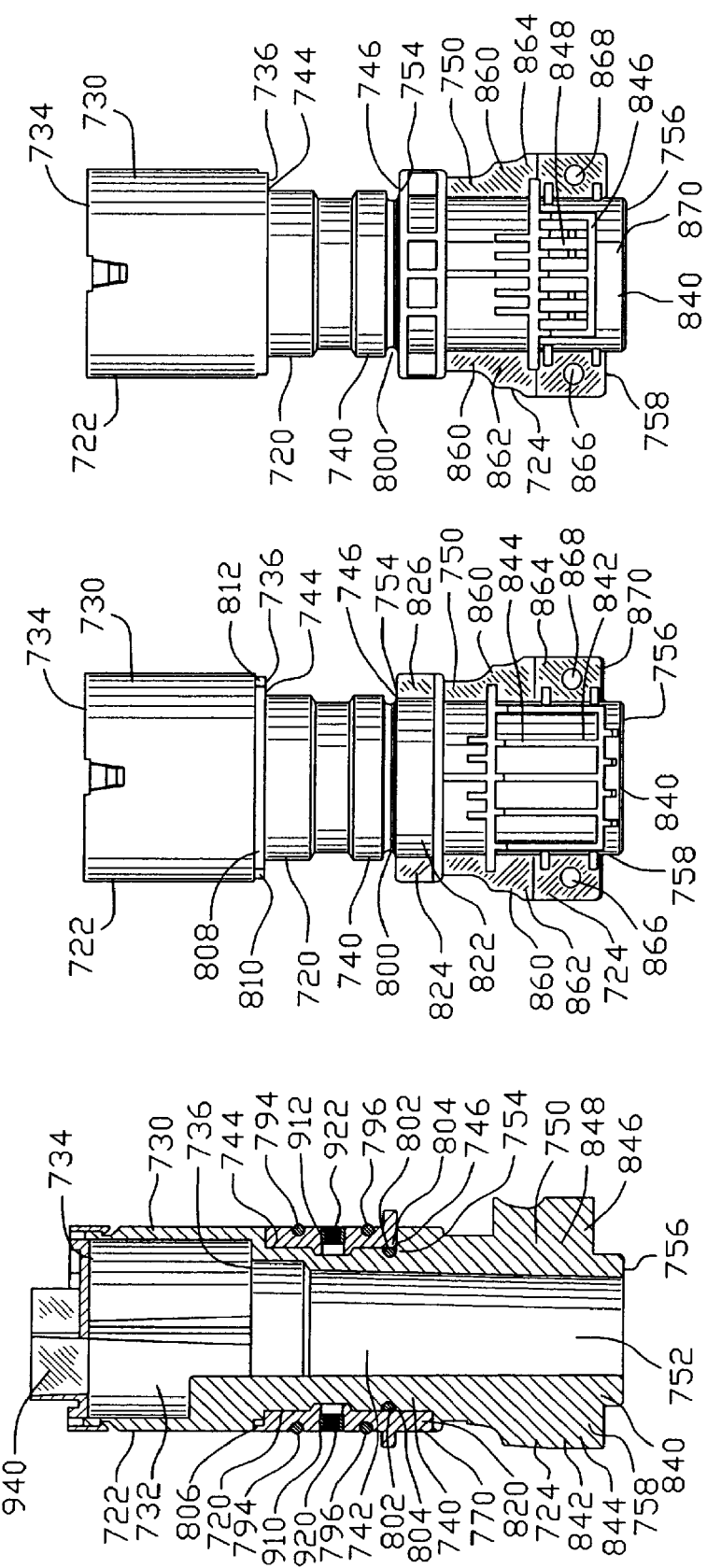

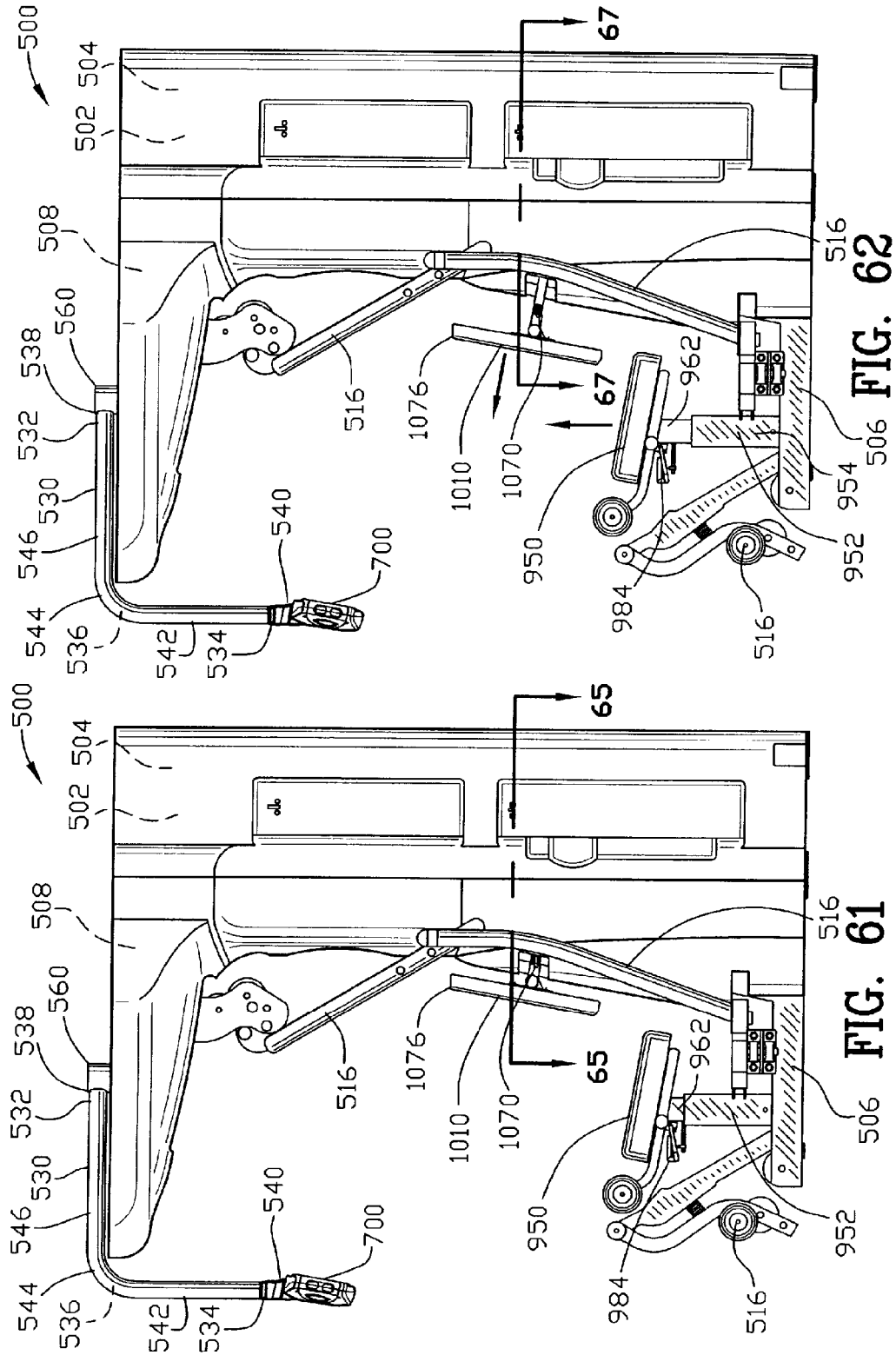

EXERCISING APPARATUS

CROSS-REFERENCE TO RELATED APPLICATIONS

This is a continuation of U.S. application Ser. No. 11/811,524 filed Jun. 11, 2007 now U.S. Pat. No. 7,771,319, which is a continuation-in-part of U.S. application Ser. No. 11/125,569 filed May 10, 2005 now U.S. Pat. No. 8,105,207. U.S. application Ser. No. 11/811,524 filed Jun. 11, 2007 claims the benefit of priority from U.S. Provisional Application Ser. No. 60/662,935, filed Mar. 16, 2005, and from U.S. Provisional Application Ser. No. 60/569,535 filed May 10, 2004. All subject matter set forth in the above referenced applications are hereby incorporated by reference into the present application as if fully set forth herein.

BACKGROUND OF THE INVENTION

1. Field of the Invention

This invention relates to exercising and more particularly to the improved apparatus for enabling an operator to exercise.

2. Background of the Invention

Regular exercise and physical activity are extremely important and beneficial for long-term health and well-being. Some of the benefits of exercise and physical activity include a reduced risk of premature death, heart disease, high blood pressure, cholesterol and a reduced risk of developing colon cancer and diabetes. In addition, the benefits of exercise and physical activity further include a reduced body weight, a reduced risk of depression and improved psychological well-being.

As such, various types of exercising equipment have been proposed by the prior art for enabling an operator to exercise. Currently used exercising equipment is difficult to use and requires the expertise of an instructor or a personal trainer to teach the user the proper techniques and usage of the equipment. The user must also remember the required settings for the equipment and understand when these settings should be changed as the physical ability and strength of the user increases. Unfortunately, because of these limitations in order for an individual to properly and effectively utilize the exercise equipment the supervision of an experienced trainer is required.

The need exists for an exercise device which minimizes the need for extensive instruction from a personal trainer or instructor. Further, a device capable of recording the progress of the user would enable the user to more easily match the settings of the device to the improvement in the physical condition of the user. The ability of the device to record strength, and personal physical condition of the user such as heart rate would further increase the value of the device to the user. By combining these features in a device which is simple to maintain would provide a significant contribution to the art. The following U.S. patents are the examples of an attempt of the prior art to solve these problems.

U.S. Pat. No. 5,785,632 to Greenberg, et al. discloses an apparatus for providing feedback to a user of a weight stack machine having weights for lifting and an enclosure adapted for attachment to the weight stack machine. A weight sensor for determining the number of weights lifted is provided as well as an means for detecting the motion of the weights during a lift. An electronic detector is operatively coupled to the weight sensor and the encoder for computing data describing the number of weights lifted. An interface for transmitting the computed data from the electronic detector to a central storage and the display is provided. The interface also receives information from the central storage and displays it on the display.

U.S. Pat. No. 5,931,763 to Alessandri discloses a system for programming training on exercise apparatus, with a series of exercises defining a personalized program, includes a central unit with first processor and a bi-directional data transferor; a portable medium, with a portable memory for data storage; a plurality of stations, not connected to one another by a data transmission line, and located at the exercise apparatus, with a second processor and a bi-directional data transferor from and to the portable medium, so as to receive as input the data in the portable memory relative to the exercise to be performed on an individual apparatus, for programming the apparatus, and so as to transfer as output to the portable memory upon completion of the exercise, data relative to the performance of the exercise so as to allow such data to be controlled. The first processor, after receiving from the portable medium the actual data for an exercise just completed, through the bi-directional data transferor of the said central unit, being capable of modifying the program in accordance with the actual data received. The central unit has data storage and/or comparator means, connected to the first processor, or the plurality of stations have data storage and/or comparator means, connected to the second processor, in order to allow the use of specific data.

U.S. Pat. No. 6,228,000 to Jones discloses a method and apparatus for testing the muscle strength of a subject wherein both static and dynamic strength tests are conducted on the subject during which forces exerted by the muscles are measured by devices which are connected to a computer and a display screen for displaying the strength of the muscles at different positions of a subject's body part. In the dynamic strength test, the subject moves a movement arm by exerting the muscles to be tested. The movement arm is connected to a resistance weight to oppose movement by the subject. In the static strength test, the movement arm is fixed in position and the subject exerts a body part against the movement arm upon exertion of the muscles to be tested. Force and angle measuring devices are connected to the movement arm and the computer for enabling the muscle strength to be displayed in terms of torque at various angular positions of the body part.

Although the aforementioned prior art have contributed to the development of the art of exercising equipment, none of these prior art patents have solved the needs of this art.

Therefore, it is an object of the present invention to provide an improved apparatus for enabling an operator to exercise.

Another object of this invention is to provide an improved apparatus for placing an object between a storage position to a usage position.

Another object of this invention is to provide an improved pivotable holder wherein the pivotable holder's structure, attachment mechanism and locking device are simplified.

Another object of this invention is to provide an improved pivotable holder wherein the pivotable holder's attachment to a support base does not require drastically altering the support base.

Another object of this invention is to provide an improved exercise device requiring a minimum of expert instruction.

Another object of this invention is to provide an improved exercise device capable of recording the progress and physical characteristics of the user in a portable format.

Another object of this invention is to provide an improved exercise device which is simple to maintain.

Another object of this invention is to provide an improved exercise device with a pivoting arm.

Another object of this invention is to provide an improved exercise device with a pivoting user interface.

Another object of this invention is to provide an improved exercise device with an adjustable seat.

Another object of this invention is to provide an improved exercise device with an adjustable seatback.

The foregoing has outlined some of the more pertinent objects of the present invention. These objects should be construed as being merely illustrative of some of the more prominent features and applications of the invention. Many other beneficial results can be obtained by modifying the invention within the scope of the invention. Accordingly other objects in a full understanding of the invention may be had by referring to the summary of the invention and the detailed description describing the preferred embodiment of the invention.

SUMMARY OF THE INVENTION

A specific embodiment of the present invention is shown in the attached drawings. For the purpose of summarizing the invention, the invention relates to an apparatus for enabling an operator to exercise comprising a frame having a body, a base and a top. A load is positioned on the frame for providing a resistive force. A press is positioned on the frame for displacement by the operator. A linkage joins the load with the press for displacing the load upon displacement of the press by the operator. An arm extends between a support end and a user end. A support pivot secures the support end of the arm to the top of the frame for pivoting the arm about the frame. A user interface inputs and outputs data. A user pivot securing the user interface to the user end of the arm for pivoting the user interface about the arm.

In a more specific embodiment of the invention, the support pivot comprises a cylindrical body defining an interior chamber extending between a first end and a second end. A pin traverses through the top of the frame and through the interior chamber of the support pivot to pivotably mount the support pivot to the top of the frame. A stop plate extends from the second end of the cylindrical body. A stop pin extends from the top of the frame for contacting the stop plate for terminating rotation of the arm. A brake plate extends from the second end of the cylindrical body. A brake extends from the top of the frame for contacting the brake plate for restricting the rotational speed of the arm.

In a more specific embodiment of the invention, the arm includes an interior chamber extending from the user end. The user pivot has a bushing bearing neck interposed between a pivot head and a pivot base. A first bushing and a second bushing rotatably engage the bushing bearing neck. A base receiver is positioned within the user interface for receiving the pivot base of the user pivot. A keying receiver is integral to the base receiver. A keying mount is integral to the pivot base for engaging the keying receiver to lock the user pivot to the user interface. The pivot head and the bushing bearing neck is inserted into the interior chamber of the arm for positioning the first bushing and the second bushing within the arm. A first fastener secures the first bushing relative to the arm for rotatably pivoting the user pivot relative to the arm. A second fastener secures the second bushing relative to the arm for rotatably pivoting the user pivot relative to the arm.

In a more specific embodiment of the invention, a first seat support includes a cylindrical body defining an interior chamber extending between a first end and a second end. The second end of the first seat support is secured to the base. A second seat support has a cylindrical body defining an interior chamber extending between a first end and a second end. The second end of the second seat support is inserted into the first end of the first seat support for telescoping the second seat support within the interior chamber of the first seat support. A seat is secured to the first end of the second seat support. A pneumatic cylinder is interposed between the first end of the second seat support and the base for supporting the seat at multiple positions. A seat actuator is secured to the seat for the operator to operate the pneumatic cylinder.

In a more specific embodiment of the invention, a first backseat support has a cylindrical body extending between a first end and a second end. The second end of the first backseat support is secured to the first frame coupling. The first end of the first backseat support is secured to the second frame coupling. A second backseat support has a cylindrical body defining an interior chamber extending between a first end and a second end. A first backseat guide is secured to the second frame coupling for slidably engaging the cylindrical body of the second backseat support. A second backseat guide is secured to the second end of the second backseat support for slidably engaging the cylindrical body of the first backseat support. A backseat is secured to the first end of the second backseat support. A locking plate pivotably engages the second backseat guide and slidably engaging the cylindrical body of the first backseat support for locking the second backseat guide relative to the first backseat support for supporting the backseat at multiple positions. A backseat actuator is secured to the second backseat support to operate the locking plate.

In one embodiment of the invention an electrical network enables an operator to exercise including a plurality of exercise machines. Each of the plurality of exercise machines has an exercise electric storage for storing data relative to the exercise of the operator on the plurality of exercise machines respectively. A serial link electrically couples the plurality of exercise machines for transferring the data relative to the exercise of the operator between the plurality of exercise machines respectively. A data transfer device has a transfer electric storage and is electrically coupled to the serial link for transmitting and receiving the data between the plurality of exercise machines and the data transfer device. A local computer has a local electric storage for storing the data relative to the exercise of the operator on the plurality of exercise machines respectively. A local link electrically couples the data transfer device to the local computer for transmitting and receiving the data between the data transfer device and the local computer. A remote computer has a remote electric storage for storing the data relative to the exercise of the operator on the plurality of exercise machines respectively. A network electrically couples the local computer to the remote computer for transmitting and receiving the data between the local computer and the remote computer.

The foregoing has outlined rather broadly the more pertinent and important features of the present invention in order that the detailed description that follows may be better understood so that the present contribution to the art can be more fully appreciated. Additional features of the invention will be described hereinafter which form the subject matter of the invention. It should be appreciated by those skilled in the art that the conception and the specific embodiments disclosed may be readily utilized as a basis for modifying or designing other structures for carrying out the same purposes of the present invention. It should also be realized by those skilled in the art that such equivalent constructions do not depart from the spirit and scope of the invention.

BRIEF DESCRIPTION OF THE DRAWINGS

For a fuller understanding of the nature and objects of the invention, reference should be made to the following detailed description taken in connection with the accompanying drawings in which:

FIG. 17 is a bottom view of the seat;

FIG. 18 is a magnified view of a lower portion of FIG. 5;

FIG. 19 is a magnified view of a portion of FIG. 18;

FIG. 42 is a front view of a second embodiment of the subject invention;

FIG. 43 is a view similar to FIG. 42 illustrating an arm and a user interface in an alternative position;

FIG. 50 is a magnified view of a portion of FIG. 49;
FIG. 51 is an exploded view of FIG. 50;
FIG. 55 is a magnified view of a portion of FIG. 49;
FIG. 56 is an exploded view of FIG. 55;
FIG. 57 is a right side view of a portion of FIG. 56;
FIG. 58 is a left side view of a portion of FIG. 56;
FIG. 59 is a magnified view of a portion of FIG. 55.

FIG. 61 is a view similar to FIG. 45 illustrating a seat and backseat positioned in a first position;

FIG. 62 is a view similar to FIG. 61 illustrating the seat and backseat positioned in a second position;

Similar reference characters refer to similar parts throughout the several Figures of the drawings.

DETAILED DISCUSSION

Figure 1:
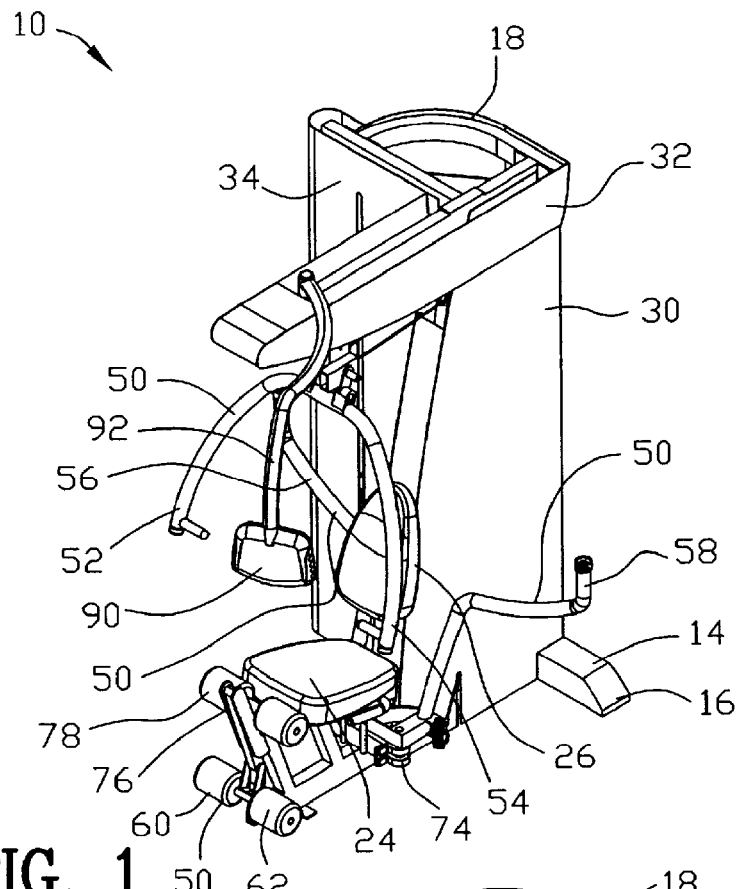
FIG. 1 is an isometric view of an apparatus for enabling an operator to exercise incorporating the present invention.
Figure 2:
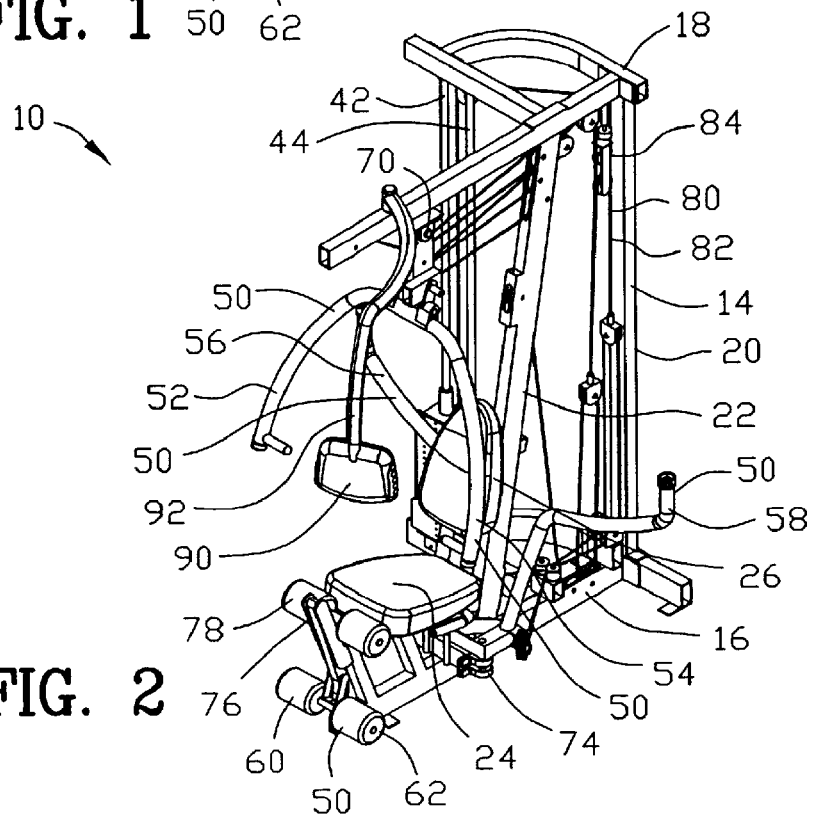
FIG. 2 is an isometric view of the apparatus of FIG. 1 without a plurality of shrouds.
Figure 3:
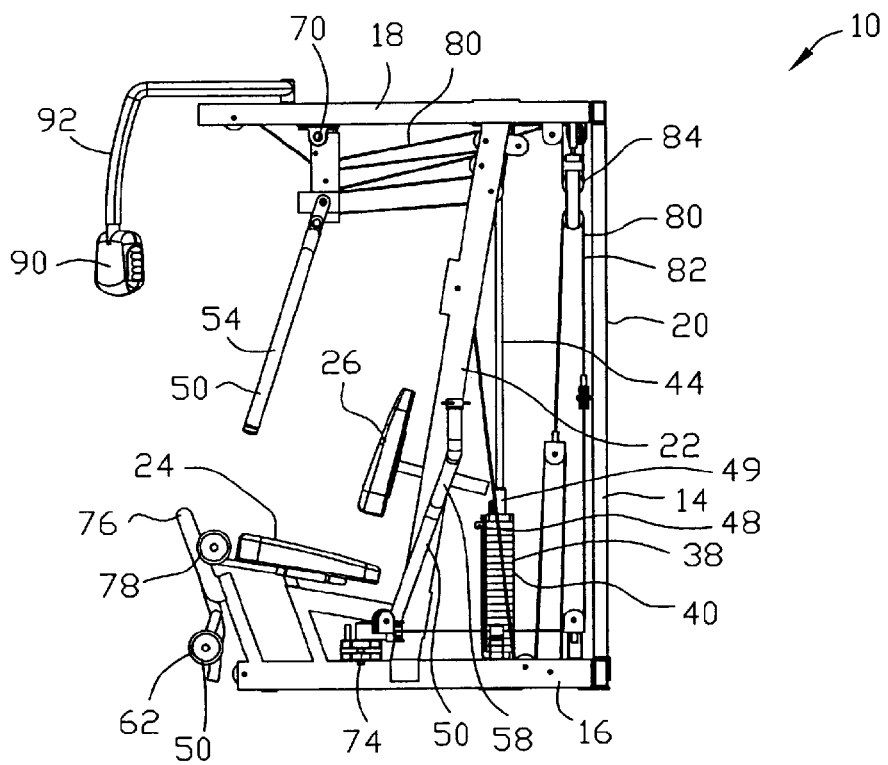
FIG. 3 is a right side view of FIG. 2.
Figure 4:
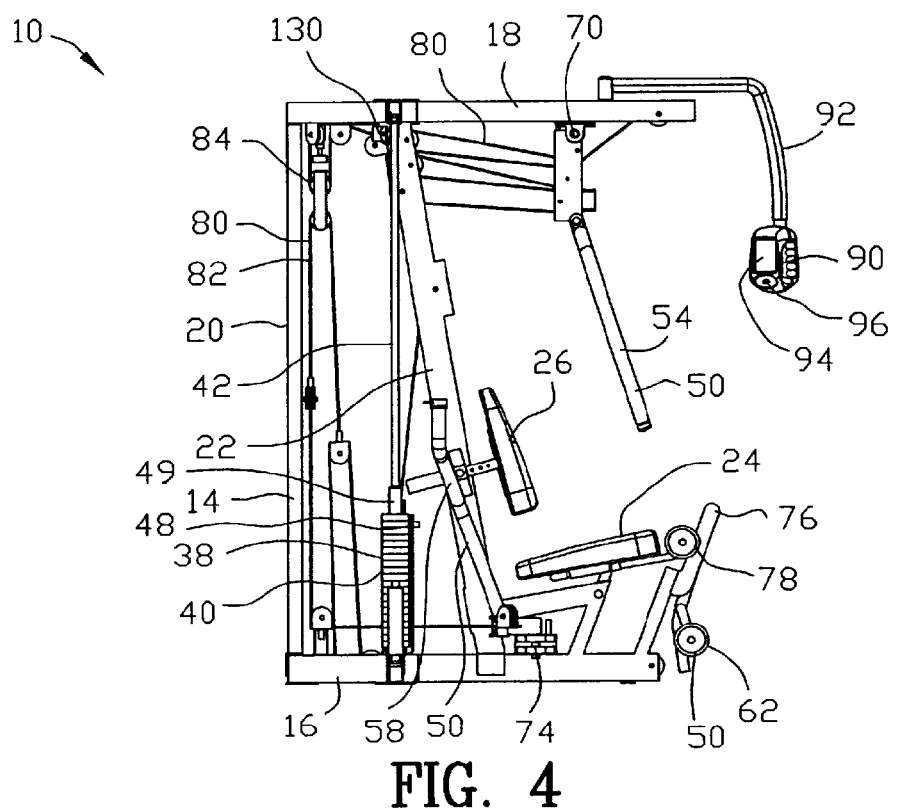
FIG. 4 is a left side view of FIG. 2.
Figure 5:
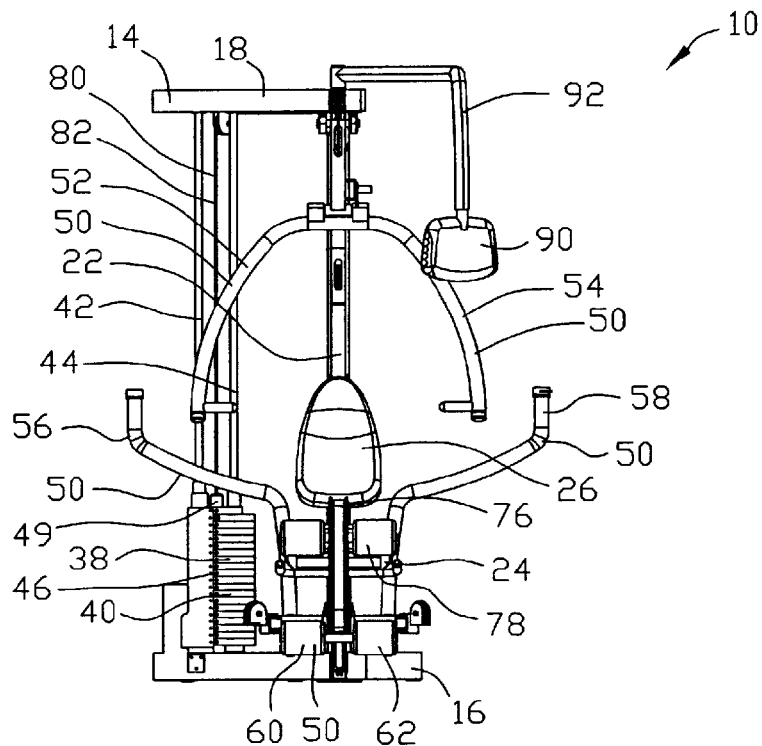
FIG. 5 is a front view of FIG. 2.
Figure 6:
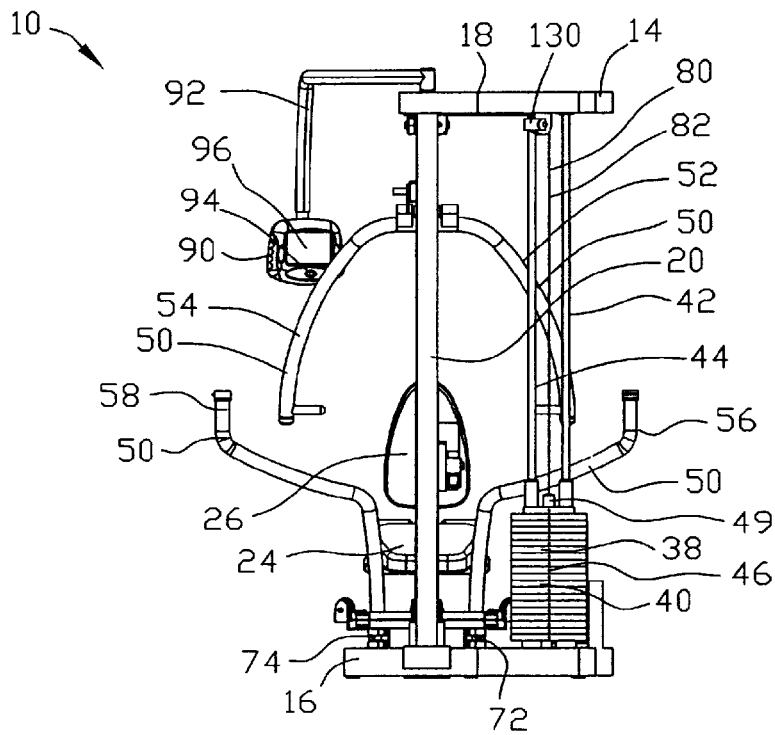
FIG. 6 is a rear view of FIG. 2.
Figure 7:
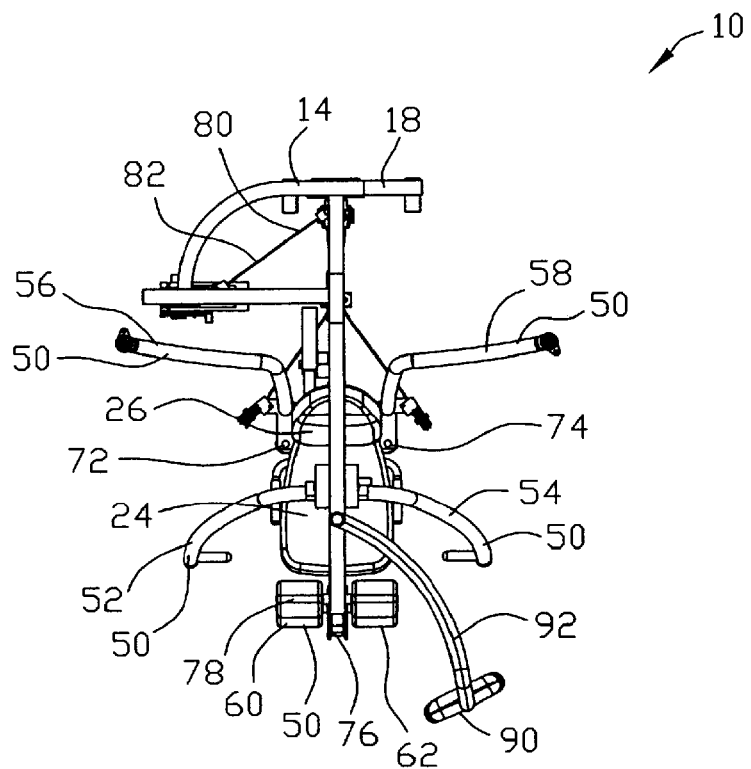
FIG. 7 is a top view of FIG. 2.
Figure 8:
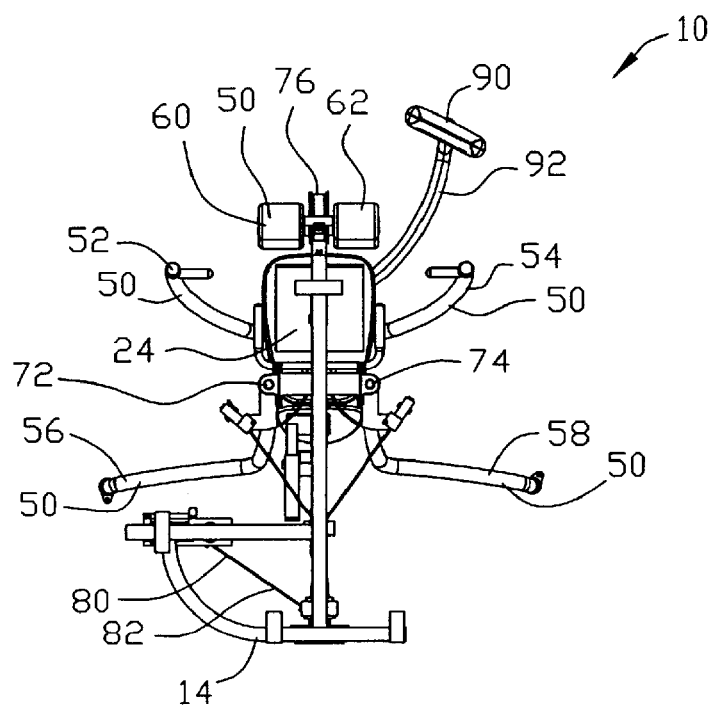
FIG. 8 is a bottom view of FIG. 2.

FIGS. 1-8 are various views of an apparatus 10 for enabling an operator 12 (not shown) to exercise incorporating the present invention. The frame 14 includes a lower frame unit 16 and an upper frame unit 18 separated and supported by a first frame coupling 20 and a second frame coupling 22. The frame 14 may be constructed from square tubing apprising steel or other similar material. The lower frame unit 16 includes a seat 24 for supporting a lower portion of the operator 12. The second frame coupling 22 includes a back rest 26 for supporting an upper portion of the operator 12.

The apparatus 10 may further include a central frame shroud 30 for concealing the first and second frame coupling 20 and 22. The upper frame unit 18 may include an upper frame shroud 32 for concealing the upper frame unit 18. The central frame shroud 30 and the upper frame shroud 32 may be constructed of a polymeric material or other similar material.

A load 38 is positioned on the frame 14 by providing a first and a second weight guide 42 and 44 extending from the lower frame unit 16 to the upper frame unit 18. The load 38 provides a resistive force to resists a force exerted by the operator 12. The load 38 may further comprise a plurality of weights 40 each including a horizontal weight cavity 46 for receiving a pin 48. Each of the plurality of weights 40 also include a vertical bore 47 (not shown) for receiving a lifter pin 49. The lifter pin 49 has a plurality of horizontal pin cavities 45 (not shown) for receiving the pin 48. To lift the load 38 the pin 48 is inserted into a horizontal weight cavity 46 of one of the plurality of weights 40 and engages one of the horizontal pin cavities 45. A vertical force is then applied to the lifter pin 49 to lift the load 38. The plurality of weights 40 may be constructed of plate steel or other similar material. The load 38 may be concealed by a weight frame shroud 34 secured to the frame 34. The weight frame shroud 34 may be constructed of a polymeric material or other similar material.

The apparatus 10 further includes a press 50 positioned on the frame 14 for displacement by the operator 12. The press 50 may include a first and second chest press 52 and 54 for exercising the chest muscles of the operator 12. The first and second chest press 52 and 54 are secured to the frame 14 by a chest pivot 70 secured to the upper frame unit 18. The press 50 may also include a first and second back press 56 and 58 for exercising the back muscles of the operator 12. The first and second back press 56 and 58 are secured to the frame 14 by a first and second back pivot 72 and 74 respectively. The first and second back pivot 72 and 74 are secured to the lower frame unit 16. The press 50 may also include a first and second leg press 60 and 62 for exercising the leg muscles of the operator 12. The first and second leg press 60 and 62 are secured to the frame 14 by a leg press pivot 76 secured to the lower frame unit 16. The frame 14 includes a leg rest 78 for cushioning the leg of the operator 12. The apparatus as shown with a chest press, a back press and leg press, however it should be understood that other presses may be utilized with the apparatus 10. The press 50 is joined to the load 38 by a linkage 80 such that the load is displaced upon displacement of the press 50 by the operator 12. The linkage 80 may include a plurality of cables 82 comprising steel or other similar material extending from the lifter pin 49 to the press 50. The linkage 80 may be routed from the load 38 to the press by a plurality of pulleys 84.

The plurality of cables 82, plurality of pulleys 84 and plurality of weights 40 are concealed by the central frame shroud 30, the upper frame shroud 32 and the weight frame shroud 34. The central frame shroud 30, upper frame shroud 32 and weight frame shroud 34 serve to prohibit access to the plurality of cables 82, plurality of pulleys 84 and plurality of weights 40 in order to prevent injury to the operator 12 or others. The central frame shroud 30, the upper frame shroud 32 and the weight frame shroud 34 also serve to make the apparatus 10 aesthetically pleasing.

Figure 9:
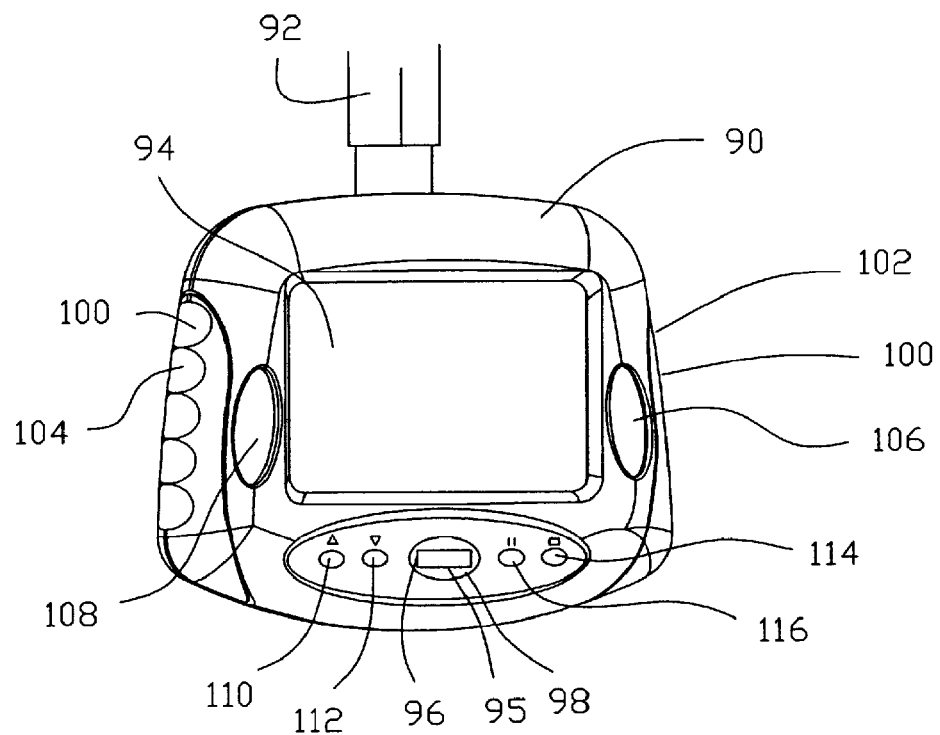
FIG. 9 is a magnified front view of a display.
Figure 10:
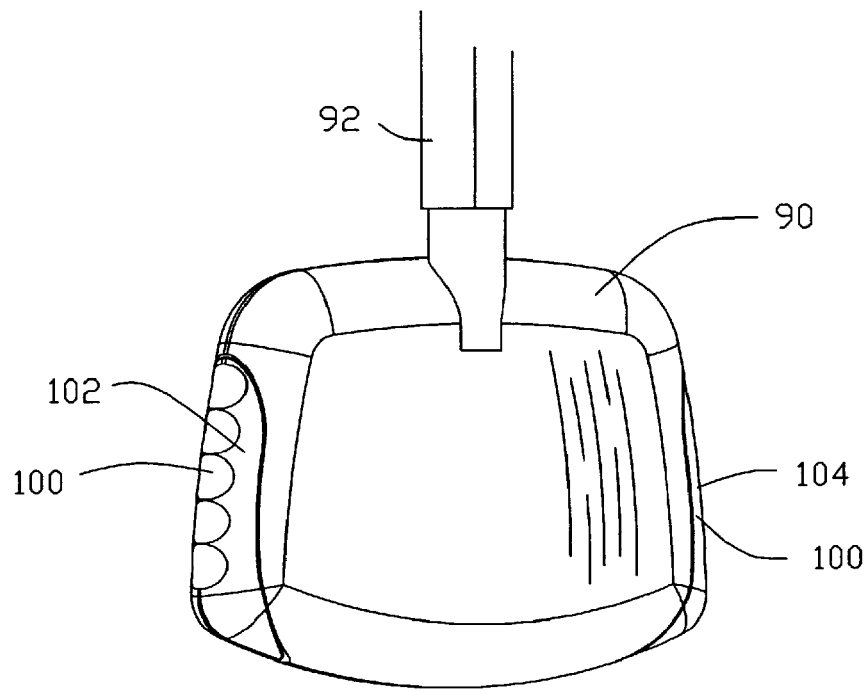
FIG. 10 is a rear view of FIG. 9.

FIGS. 9 and 10 are enlarged views of portions of FIGS. 1-8 illustrating a user interface module (UI) 90. The apparatus 10 includes a user interface module 90 secured to the upper frame unit 18 of the frame 14 by a support arm 92. The user interface module 90 includes a liquid crystal touch screen display 94 for presenting visual data and inputting data. The user interface module 90 includes an input port 95 for receiving a memory storage 96 for storing data. The input port 95 may include a USB port or other data port. The memory storage 96 may include a removable memory device 98 or other portable memory storage. The user interface module 90 also includes a contact 100 for measuring a heart rate and a body fat of the operator 12. The contact 100 may include a first and a second pad 102 and 104 positioned on either side of the user interface module 90. The contact 100 measures the heart rate of the operator 12 by positioning his hands upon the first and second pads 102 and 104. The first and second pads 102 and 104 determine the heart rate of the operator 12 by the contact method. The contact 100 can also measure the body fat of the operator by positioning his hands upon the first and second pads 102 and 104. The first and second pad 102 and 104 determine the body fat of the operator 12 by a Body Fat PCB technology or the bio-impedance method.

The user interface module 90 may further include a first and second speaker 106 and 108 creating audible signals to provide instructions or confirmation of an input into the user interface module 90. The user interface module 90 also includes a first and second function button 110 and 112 for increasing or decreasing a function. In addition, the user interface module 90 may include a stop button 114 and a pause button 116 for either terminating the exercising instruction or pausing the exercising instruction.

Figure 11:
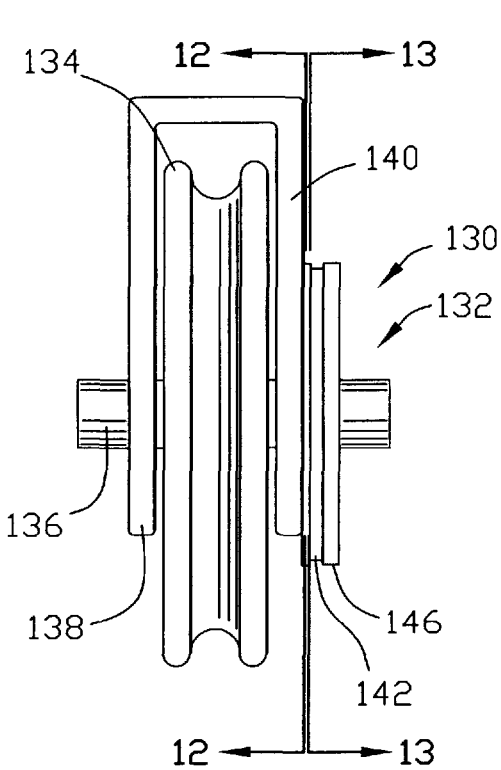
FIG. 11 is a front view of a pulley and a sensor for measuring a displacement and speed of a linkage.
Figure 12:
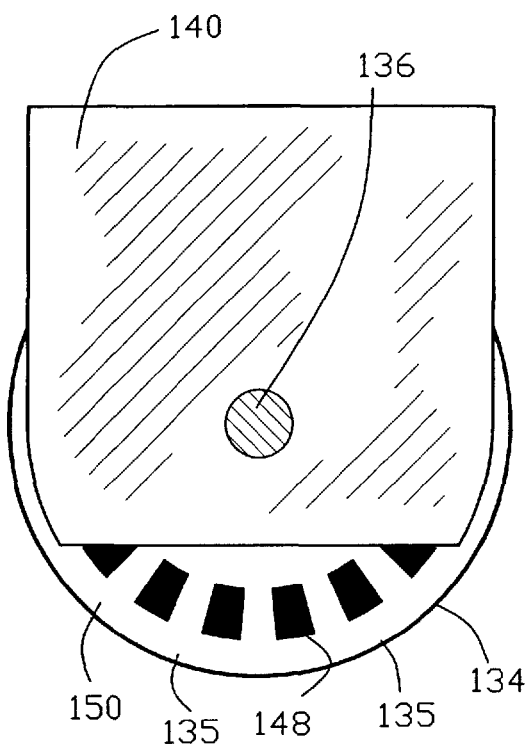
FIG. 12 is a sectional view along line 12-12 in FIG. 11.
Figure 13:
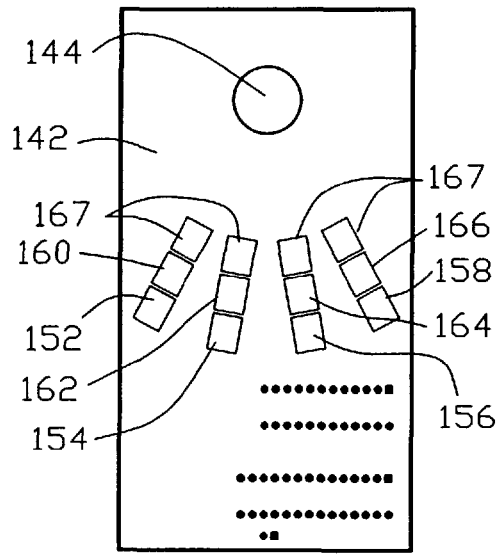
FIG. 13 is a sectional view along line 13-13 in FIG. 11.

FIGS. 11-13 are various views of a sensor 130 for measuring a displacement and a speed of the linkage 80. The sensor 130 is positioned on the upper frame unit 18 of the frame 14. The sensor 130 may include a rotary optical encoder 132. The rotary optical encoder 132 comprises a sensor pulley 134 rotating about a shaft 136. The sensor pulley 134 is retained on the shaft 136 by a first pulley retainer 138 and a second pulley retainer 140. A sensor board 142 is positioned adjacent to the sensor pulley 134. The sensor board 142 includes a shaft aperture 144 for engaging the shaft 136. The sensor board 142 is retained adjacent to the sensor pulley 134 by a sensor retainer 146. The sensor pulley 134 has an absorbent surface 148 adjacent to a reflective surface 150. The sensor board 142 has a first, second, third and fourth reflective optical sensors 152, 154, 156 and 158 respectively. In addition, the sensor board 142 has a first, second, third and fourth infrared LEDs 160, 162, 164 and 166 respectively. The reflective optical sensors 152, 154, 156 and 158 and infrared LEDs 160, 162, 164 and 166 are utilized at phase angles of 0, 45, 90 and 135 degrees. As the sensor pulley 134 is rotated about the shaft 136, the light emitted from the first, second, third and fourth infrared LEDs 160, 162, 164 and 166 are either reflected by the reflected surface 150 or absorbed by the absorbent surface 148 of the sensor pulley 134. Light emitted from the first, second, third and fourth infrared LEDs 160, 162, 164 and 166 that are reflected off the reflected surface 150 will strike the reflective optical sensors 152, 154, 156 and 158 respectively. Upon the reflective optical sensors 152, 154, 156 and 158 receiving a light emission, the reflective optical sensors 152, 154, 156 and 158 are switched on to allow current flow. When the reflective optical sensors 152, 154, 156 and 158 are not receiving a light emission, the reflective optical sensors 152, 154, 156 and 158 are switched off to terminate current flow. The result of the reflective optical sensors 152, 154, 156 and 158 switching on and off produce a pulse electrical signal.

Figure 14:
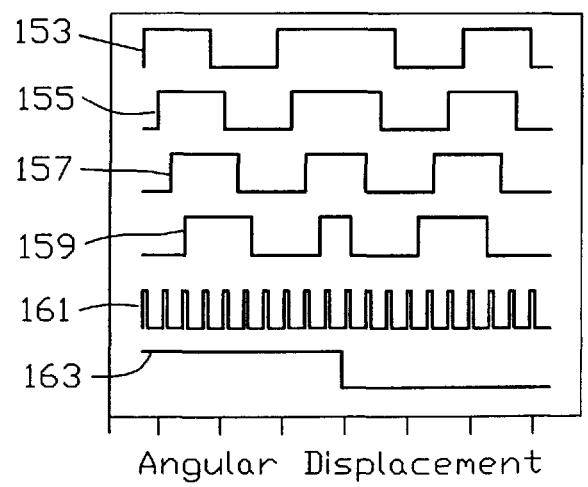
FIG. 14 is chart illustrating the plurality of electrical pulse signals from a sensor, a count per turn of a sensor pulley and the rotational direction of the sensor pulley.

FIG. 14 illustrates a first, second, third and fourth electrical signal 153, 155, 157 and 159 produced by the reflective optical sensors 152, 154, 156 and 158 respectively. After the pulse electrical signals are amplified and converted, both the angular displacement and the rotational direction of the sensor pulley 134 can be determined. The angular displacement of the sensor pulley 134 is converted to a count 161 per turn of the sensor pulley 134. The rotational direction of the sensor pulley 134 is converted to a direction 163 of the sensor pulley 134.

Each of the reflective optical sensors 152, 154, 156 and 158 and infrared LEDs 160, 162, 164 and 166 may include a Fairchild p/n QRD1114 consisting of a combined infrared LED/photodetector 167. The sensor pulley 134 includes alternating sectors of absorbent surfaces 148 and reflective surfaces 150 for absorbing or reflecting the infrared light emitted from the infrared LED/photodetector 167. The sensor pulley 134 may be constructed of a black ABS pulley wheel 135 and have a nominal radius 45 mm. The alternating sectors of absorbent surfaces 148 and reflective surfaces 150 may be constructed by masking the black ABS pulley wheel 135 and spraying a white paint into the voids of the mask. Alternatively, a pad-printing may be used to apply the alternating sectors of absorbent surfaces 148 and reflective surfaces 150 to the sensor pulley 134. The number of both absorbent surfaces 148 and reflective surfaces 150 positioned on infrared LED/photodetector 167 may include eighteen (18) wherein both absorbent surfaces 148 and reflective surfaces 150 have a width of 7.85 mm. The four infrared LED/photodetectors 167 are utilized at phase angles of 0, 45, 90 and 135 degrees and are placed at an angular spacing of 22.5 degrees to provide reliable position encoding with an angular resolution of 2.5 degrees.

The postscript program to generate a 36 half-element (number of alternating black and white surfaces) wherein the sensor pulley 134 has a nominal radius of 45 mm may include the following:

```
%! Postscript utility for printing an encoder wheel
%
/inch {72 mul} def   % #points/inch (don't change me)
/od 3.55 inch def         % outside diameter of wheel
/id 0.81 inch def         % inside diameter of wheel (hub)
/sod 3.55 inch def        % outside diameter of segments
/sid 2.75 inch def        % inside diameter of segments
/orad od 2 div def
/irad id 2 div def
/sorad sod 2 div def
/sired sid 2 div def
/segments 36 def    % number of segments (black and white)
/angle 360 segments div def
/wedge
{/radius exch def
/angle_s exch def
/angle_e exch def
newpath
% 0 0 moveto
0 0 radius angles_s angle_e arc
0 0 sired angle _e angle_s arc
closepath
}def
/circle
{
    /radius exch def
    newpath
    0 0 radius 0 360. arc
    closepath
} def
gsave
4.0 inch 4.0 inch translate
0 1 segments {
360 segments div rotate
angle 0 sorad wedge
2mod 0 eq{1}{0}ifelse
setgray fill
} for
0 setgray
0.5 setlinewidth
irad circle stroke
orad circle stroke
grestore
showpage
```

The decoding of the sensor 130 for measuring a displacement and a speed of the linkage 80 may be processed by using an Atmel ATF750CL-15 Complex Programmable Logic Device (CPLD) having the following equations:

```
Name Decoder8;
PartNo QD001;
Date 9/22/2004;
Revision 01;
Designer INW:
Company Inwoods Consulting;
Assembly AHF-003;
Location U8;
Device V750C;
/************* INPUT PINS *******************/
PIN 1= Clk;            /* 6MHz input Clock */
PIN 2= Rest;           /* Reset */
```

-continued

```
PIN 3= D0;             /* Phi 0 degrees*/
PIN 4= D1;             /* Phi 45 degrees */
PIN 5= 02;             /* Phi 90 degrees */
PIN 6= D3;             /* Phi 135 degrees */
/************* OUTPUT PINS *******************/
PIN 14= tCount;        /* Toggle Count*/
PIN 15= Up;            /* Up pulses, for internal use */
PIN 17= pCount;        /* un-delayed Count */
PIN 18= DIR;           /* Direction 1 = Up, 0 = Down */
PIN 19= Count;         /* Pulse count output*/
PIN 20= QD0;           /* Phi 0, delayed 2 DCLK*/
PIN 21= QD1;           /* Phi 45, delayed 2 DCLK */
PIN 22= QD2;           /* Phi 90, delayed 2 DCLK*/
PIN 23= QD3;           /* Phi 135, delayed 2 DCLK */
/*
** PINNODE 25..34 for Q1 of pins 14..23
** PINNODE 35..44 for Q0 of pins 14..23 (i.e. I/O pins)
*/
PINNODE 25 = DCLK0;
PINNODE 27 = DCLK1;
PINNODE 37 = DCLK2;
PINNODE 31 = Q0; /* Phi 0, delayed 1 DCLK, buried register */
PINNODE 32 = 01; /* Phi 45, delayed 1 DCLK, buried register */
PINNODE 33 = 02; /* Phi 90, delayed 1 DCLK, buried register */
PINNODE 34 = Q3; /* Phi 135, delayed 1 DCLK, buried register */
/** Declarations and Intermediate Variable Definitions **/
/* Equations*/
/* Timing States */
DCLK2.t = DCLK1 & DCLK0;
DCLK1.t = DCLK0;
DCLK0.t = 'b'1;
[DCLK2..0].ckmux = Clk;
[DCLK2..0).ar = !Rest;
[DCLK2..0).sp ='b'0;
T0 = !DCLK2 & !DCLK1 & !DCLK0;
T1 = !DCLK2 & !DCLKI & DCLK0;
T2 = !DCLK2 & !DCLK1 & !DCLK0;
T3 = !DCLK2 & DCLK1 & DCLK0;
T4 = DCLK2 & !DCLK1 & !DCLK0;
T5 = DCLK2 & !DCLK1 & DCLK0;
T6 = DCLK2 & DCLK1 & !DCLK0
T7 = DCLK2 & DCLK1 & DCLK0;
/* Latch the phase inputs on T0 */
[Q3..0].ar = !Rest;
[O3..0].sp = 'b'0;
[Q3..0).ck = T7;
QD0.d = Q0;
QD1.d = Q1;
QD2.d = Q2;
QD3.d = Q3;
/* Clock the latched inputs on T7, giving time for edge detection */
[QD3..0].ar = !Rest;
[QD3..0].sp ='b'0;
[QD3..0].ck = T7;
QD0.d = Q0;
QD1.d = Q1;
QD2.d = Q2;
QD3.d = Q3;
\* Edge Detection, sample for falling edges on T1 and rising edges on T3 */
D0low = (!Q0 & !QD0);
D0high = (Q0 & QD0);
D0rise = (Q0 & !QD0 & T3);
D0fall =(!Q0& QD0&T1);
D1low = (!Q1 & !QDI);
D1high = (Q1 & QD1);
D1rise = (Q1 & !QD1 & T3);
D1fall = (!Q1 & QD1 & T1);
D2low = (!Q2 & !QD2);
D2high = (Q2 & QD2);
D2rise = (Q2 & !QD2 & T3);
D2fall= (!Q2 & QD2 & T1
D3low = (!Q3 & !QD3);
D3high = (Q3 & QD3);
D3rise = (Q3 & !QD3 & T3);
D3fall = (!Q3 & QO3 & T1);
/* Output a "Count" Pulse for edge edge detected */
pCount.ck = Clk;
pCountsp ='b'0;
pCount.d = (D0rise # D1rise # D2rise #D3rise # D0fall # D1fall #
```

-continued

```
D2fall #D3fall);
pCount.oe = 'b'1;
pCount.ar= !Rest;
Count.ck = Clk;
Count_sp = 'b'0;
Count.d = pCount;
Count.oe = 'b'1;
Count.ar = !Rest;
/*Toggie Count - good for debug */
tCount.ar = !Rest;
tCount.sp = 'b'0;
tCount.ck = Count;          /*Toggie output on Count*/
tCount.d = !tCount
/*Direction - Define 8 states that are identified with the "UP"
direction */
S0 = D0rise & D1low;
S1 = D0high & D1 rise & D2low;
S2 = D1high & D2rise & D3low;
S3 = D2high & D3rise;
S4 = D0fall & D1high;
S5 = D0low & D1fall & D2high;
S6 = D1 low & D2fall & D3high;
S7 = D2low & D3fall;
Up =(SO#S1 #S2#S3#S4#S5#S6#S7);
Up.oe = 'b'1;
Up.ar = !Rest;
DIR.ck = pCount;
DIR.sp ='b'0;
DIR.d = Up;
DIR.oe ='b'1;
DIR.ar = !Rest;
```

Figure 15:
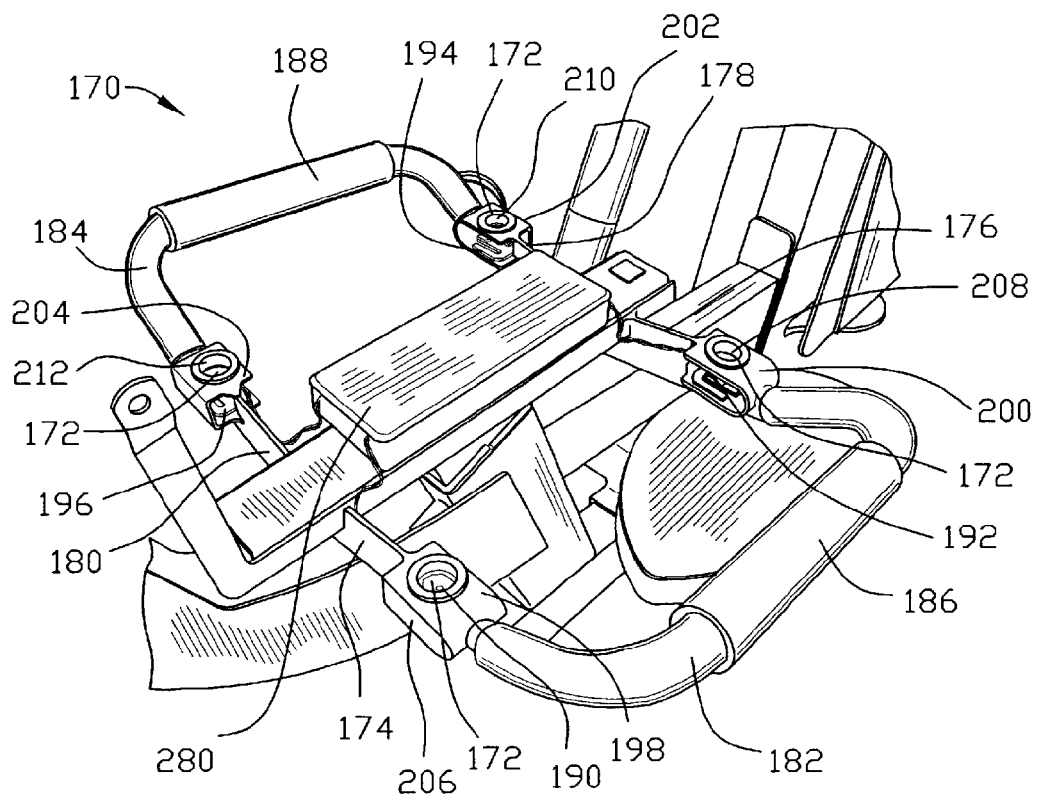
FIG. 15 is an isometric view of lower portion of FIG. 2 without a seat.
Figure 16:
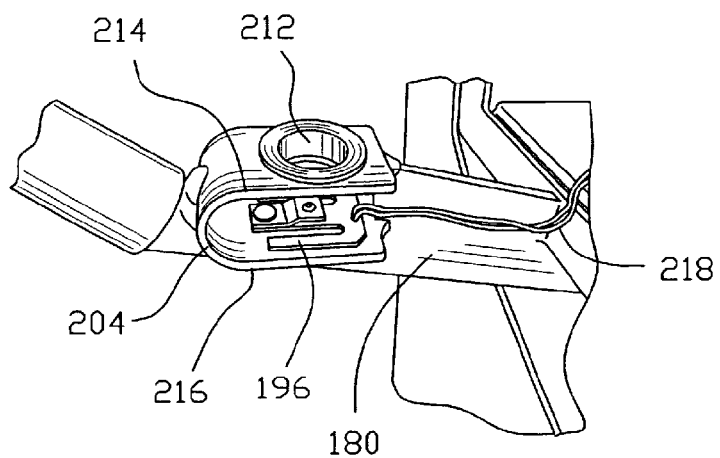
FIG. 16 is a magnified view of a portion of FIG. 14.

FIGS. 15-17 are views of a scale 170 for measuring a body weight of the operator 12. The scale 70 may comprises a plurality of strain gage load cell sensors 172. The seat 24 is secured to the frame 14 by a first, second, third and fourth seat support 174, 176, 178 and 180 extending from the lower frame unit 16. A first seat bar 182 having a first handle 186 may slidably engage the first and second seat support 174 and 176 for providing a body stabilizer for the operator 12. Similarly, a second seat bar 184 having a second handle 188 may slidably engage the third and fourth seat support 178 and 180 for providing a body stabilizer for the operator 12. The first, second, third and fourth seat support 174, 176, 178 and 180 include a first, second, third and fourth channel 198, 200, 202 and 204 respectively. The first, second, third and fourth channels include an upper leg 214 and a lower leg 216. Each of the upper legs 214 of the first, second, third and fourth channels include a first, second, third and fourth aperture 206, 208, 210 and 212 respectively. A first, second, third and fourth strain gage load cell sensor 190, 192, 194 and 196 are positioned on the first, second, third and fourth lower leg 216 of the first, second, third and fourth channel 198, 200, 202 and 204 respectively. The seat 24 has a front seat surface 220 and a rear seat surface 222. A first and a second support 224 and 226 are positioned on the underside of the seat 24 and extend past the front seat surface 220. A first and second bridge 228 and 230 extend over the first and second support 224 and 226. The first bridge 228 includes a first and a forth rod 232 and 238 for slidably engaging through the first and fourth apertures 206 and 212 to rest upon the first and fourth strain gage load cell sensors 190 and 196, respectively. The second bridge 230 includes a second and third rod 234 and 236 for and second bridge 228 and 230 include a slidably engaging through the second and third apertures 208 and 210 to rest upon the second and third strain gage load cell sensors 192 and 196, respectively.

FIGS. 18 and 19 are views of a monitor 250 for determining the number of the plurality of weights 40 that well be displaced upon the press 50 being displaced by the operator 12. The monitor 250 may include a plurality of infrared LEDs 257 and a plurality of optical sensors 258 positioned on a monitor plate 252. The monitor plate 252 includes a first and second anchor plate 254 and 256 for securing the monitor 250 adjacent to the lower frame unit 16. With the monitor plate 252 is positioned adjacent to the plurality of weights 40, as the pin 48 is inserted into horizontal weight cavity 46 of the plurality of weights 40 the light emitted from the infrared LED 257 is reflected back to the adjacent optical sensor 258 to product an electrical current.

The monitor 250 also includes a plurality of signals 260 for receiving an electrical current. The plurality of signals 260 instruct the operator 12 to place the pin 48 in one of the horizontal weight cavities 46 of the plurality of weights 40. The plurality of signals 260 may include a plurality of Bi-Color LED lights 262. A Bi-Color LED light 262 will generate a flashing green color to instruct the operator 12 to place the pin 48 in the aligning horizontal weight cavity 46. If the operator 12 places the pin in the aligning horizontal weight cavity 46 adjacent to the flashing LED light 262, the LED light 262 will convert to a steady green color. If the operator 12 places the pin in an alternative horizontal weight cavity 46 which is not adjacent to the flashing LED light 262, the LED light 262 adjacent to the pin will generate a steady red color. The monitor 250 also includes a plurality of weight values 264 to provide the operator 12 with the load value the operator 12 will be displacing upon displacement of the press 50.

Figure 20:
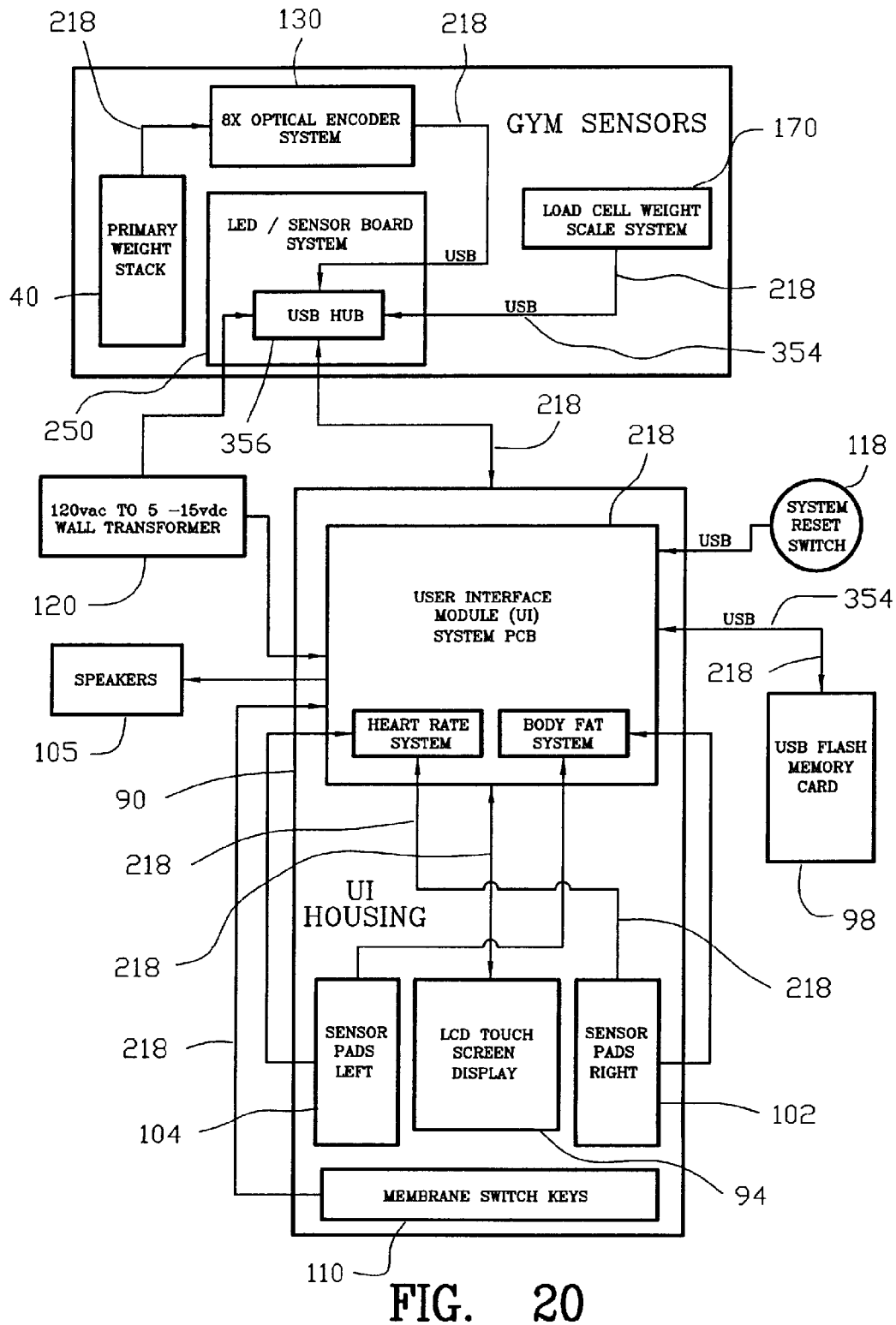
FIG. 20 is a wire diagram of the electrical components of the apparatus for enabling the operator to exercise incorporating the present invention.

FIG. 20 is a wire diagram of the electrical components of the apparatus 10 for instructing the operator 12 thru an interactive exercise program. A user interface module (UI) 90 contains a printed circuit board (PCB) 280 containing a central processing unit (CPU) 350. The CPU 350 performs the arithmetic and logical operations, namely the data received from the sensor 130, scale 170, monitor 250, the liquid crystal touch screen display 94 and memory storage 96. The PCB 280 also contains read only memory (ROM) 352 for storing software programs. The software programs instruct the operator 12 thru an interactive exercise program that monitors the operator's exercise program progress, provides exercise tips, records the operator's personal data and fitness program results and exports the operator's data to a memory storage 96. The PCB 280 is in electrical communication with the liquid crystal touch screen display 94, sensor 130, scale 170, contact 100, monitor 250, and memory storage 96 by a plurality of wires 218. The electrical communication between the PCB 280 and liquid crystal touch screen display 94, sensor 130, scale 170, contact 100, monitor 250, and memory storage 96 may include a Universal serial bus (USB) interface system 354.

More specifically, the PCB 280 communicates with the liquid crystal touch screen display 94 for providing exercising instructions to the operator 12. The operator 12 may input data from the liquid crystal touch screen display 94 to the PCB 280. The PCB 280 also receives data from the sensor 130 for processing the performance of the exercising instruction by the operator 12. The sensor 130 monitors any movement of the sensor pulley 134. The CPU 350 converts this movement into speed and direction data. The speed and direction data is displayed on the liquid crystal touch screen display 94 to provide an on-screen visual display of the speed and direction data of the plurality of weights 40 in real-time. This visual display may be beneficial for practicing the correct rate and pace for a particle exercise.

The PCB 280 receives data from the scale 170 for processing the weight of the operator 12. The scale 170 includes first, second, third and fourth strain gage load cell sensors 190, 192, 194 and 196 that are incorporated into the seat 24. The PCB 280 interprets and integrates the strain gage load cell sensors signals. The scale data is displayed on the liquid crystal touch screen display 94 and is stored on the memory storage 96 to record the operator's weight. The PCB 280 further receives data from the contact 100 for processing the heart rate and the body fat of the operator 12. The contact 100 is incorporated into the user interface module 280. The contact 100 provides sensor input to the PCB 280. The contact data is displayed on the liquid crystal touch screen display 94 and is stored on the memory storage 96 to record the operator's heart rate and body fat. The stored heart rate and body fat data is used to track the health of the operator 12.

The PCB 280 further receives data from the monitor 250 for processing the number of plurality of weights 40 displaced by the operator 12. The monitor 250 includes a plurality of infrared LED 257 aligned with a plurality of optical sensors 258 adjacent to each of the plurality of weights 40. The monitor 250 provides sensor input to the PCB 280 as to the position of the pin 48 upon the pin 48 blocking the light emitting from the infrared LED 257 to the optical sensor 258. The plurality of weight data is displayed on the liquid crystal touch screen display 94 and is stored on the memory storage 96 to record the weight lifted by the operator 12. The monitor 260 also includes a plurality of signals 260 comprising a bio-colored LEDs 262 adjacent to each of the plurality of weights 40. The software calculates the proper weight for the operator's program. The PCB 280 transmits a signal to the monitor 260 to illuminate the bio-colored LED 262 adjacent the proper weight. The illuminated bio-colored LED 262 provides a visual indication to the operator 12 regarding the pin 48 placement for an exercise. The normal condition the bio-colored LED 262 is not illuminated. When the software program sends a signal to the proper plurality of weights 40 for the operator's program, the bio-colored LED 262 will illuminate a flashing green signal to inform the operator 12 in which plurality of weights 40 to insert the pin 48. When the operator 12 has properly placed the pin 48 adjacent to the flashing green bio-colored LED 262, the optical sensor 258 senses the location of the pin 48 and will send a corresponding signal back to the PCB 280 as confirmation. The software program will then send a response signal back to the bio-colored LED 262 and turn the bio-colored LED 262 to steady green to notify the operator 12 that they have the pin 48 in the proper position for the exercise.

If the operator 12 elects to not place pin 48 in the recommended position, and places the pin 48 in an alternate position, the optical sensor 258 at the alternate position will send a signal to the PCB 280 of the alternative selection and in turn generate a pop-up notice on the liquid crystal touch screen display 94 and also send a signal to the bio-colored LED 262 at the alternate position and create a flashing red signal. The bio-colored LED 262 that was recommended for the pin 48 location will continue to flash green. If the operator 12 confirms the use of the alternate pin 48 location by interacting with the liquid crystal touch screen display 94, the software will send an appropriate signal to the alternate position of the bio-colored LED 262 and create a steady green bio-colored LED 262 condition and extinguish the bio-colored LED 262 at the recommended position. At the same time the software will change the operator's program to use the alternate position for the exercise program.

The PCB 280 receives data from both the sensor 130 and the monitor 250 thru a USB Hub system 356 that is integrated into a monitor PCB board. The user interface module 90 may also includes an audio system 106, a system reset switch 118. The audio system 105 has a first speaker 106 and a second speaker 108 that produces feedback tones during the operator's interaction with the apparatus 10. The PCB 280 may be powered by a wall transformer 120 wherein the 120 vac is converted to 5-15 vdc.

The PCB 280 further transfers data to the memory storage 96 for saving the weight and the heart rate and the body fat of the operator 12 and the number of plurality of weights 40 displaced and the performance of the exercising instruction by the operator 12. The memory storage 96 is inserted into the input port 95 located on the face of the user interface module 90. The memory storage 96 allows the apparatus 10 to acknowledge individual operators 12 and for the operator 12 to record and analyze individual personal data after the exercise session is completed. The memory storage 96 may include a removable memory device 98. The function of the removable memory device 98 may include acting as an ignition key to start the application software and load personal data and exercise programs into the user interface module 90, acting as a repository of personal operator data and exercise program data that can be removed and reinserted into any gym having an apparatus 10 to automatically load the appropriate personal operator data and continue the operator's exercise program. The removable memory device 98 may also function to allow the operator 12 to access and print out the operator's daily exercise results on a system located in a exercise facility, to permit the operator 12 to upload the operator's data to the a common Website for remote access via password encryption and permit connection to the World Wide Web and uploads data that will be used by the manufacture to populate a Global Database with information such as: Gender, Age, Height, Weight, Strength Test Results, Body Fat, Heart Rate, Resting Metabolic rate, Exercise Program Information, Program intensity Factors, Etc.

Figure 21:
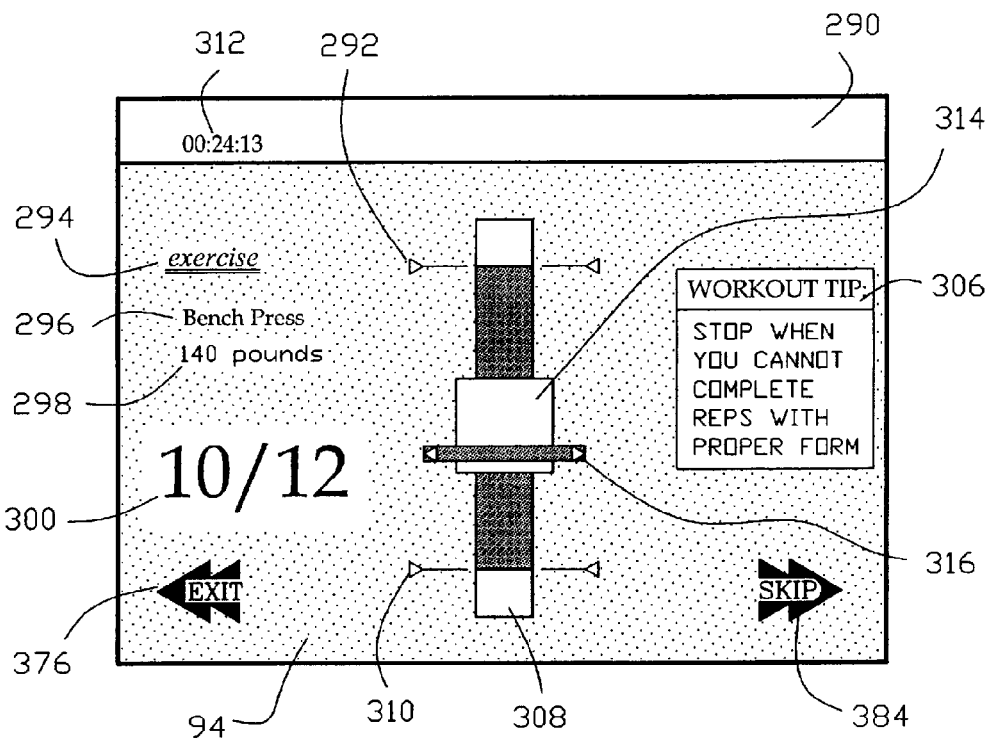
FIG. 21 is a visual image displayed on the display.
Figure 22:
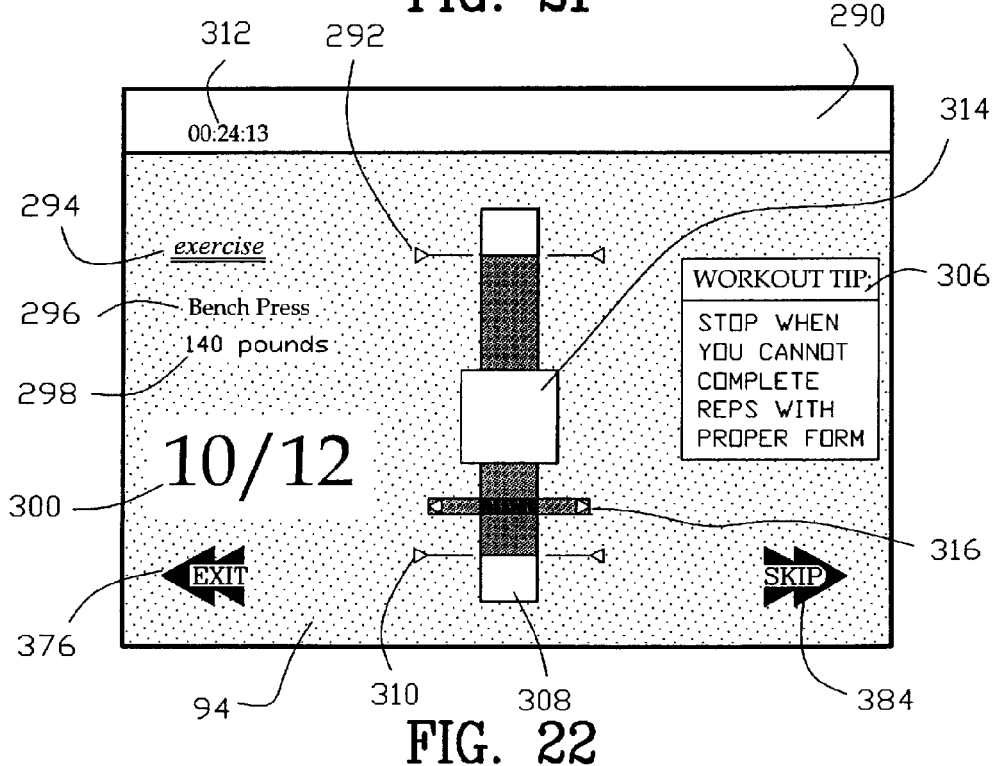
FIG. 22 is a view similar to FIG. 21.

FIG. 21 illustrates the PCB 280 transferring data to the liquid crystal touch screen display 94 for providing an exercise instruction to the operator 12. The exercising instruction 294 provided by the PCB 280 to the liquid crystal touch screen display 94 may include visual data comprising the time 292, the press type 296, the weight value 298, and the number of executed reps 300. The exercising instruction 294 may also include visual data for illustrating the displacement and the speed of the linkage 80 with respect to a predetermined standard in real time. More specifically, the visual data includes a rate of executed exercise 308 including a lower range of exercise 310 and an upper range of exercise 312. As the operator 12 displaces the press 50 to displace the load 38, the sensor 130 relays the displacement and the speed of the linkage 80. The PCB 280 then relays a graphical image of the displacement and the speed to the liquid crystal touch screen display 94. The displacement and speed of the linkage 80 is visually displayed by the operator pace bar 316. The PCB 280 provides an approximate programmed displacement and speed by a pace bar 314. The operator 12 is to match the displacement and speed of the press 50 with the displacement and speed of the 314. FIG. 22 illustrates the operator pace bar 314 outside the recommended pace bar 314. In this event, the operator 12 would need to adjust the displacement and speed of the press 50 to match the displacement and speed of the pace bar 314.

The exercising instruction 294 may further include an exercising notice 306 instructing the operator 12 to terminate exercising the current exercising instruction 294 once the operator 12 can not maintain the operator pace bar 316 within the pace bar 314.

Figure 23:
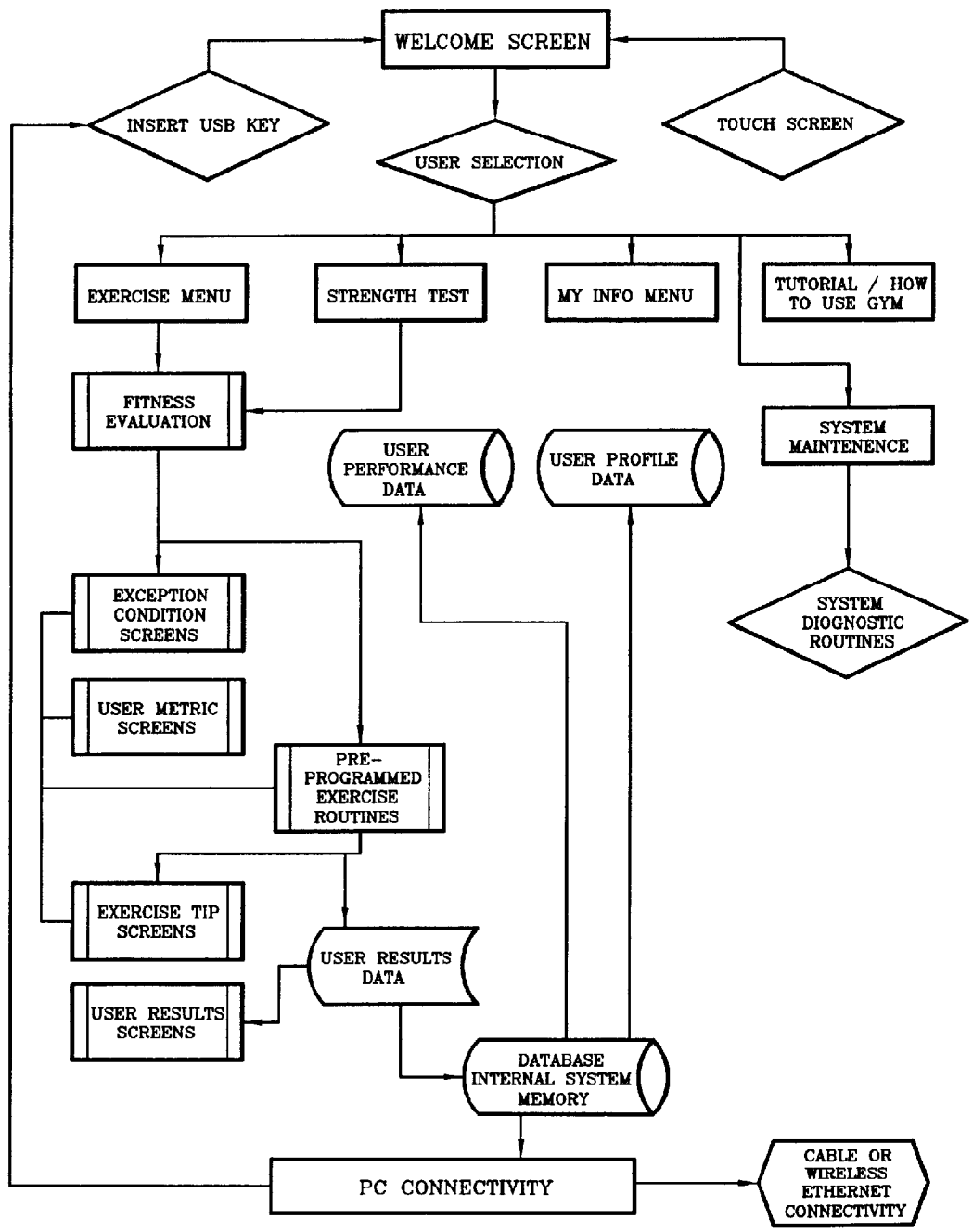
FIG. 23 is a flow chart of the process for utilizing the apparatus for enabling the operator to exercise incorporating the present invention.

FIG. 23 is a flow chart of the application software process for utilizing the apparatus 10 for enabling the operator 12 to exercise. FIGS. 24-41 illustrate the process of enabling an operator 12 to exercise incorporating the present invention, comprising the steps of inserting a memory storage into a processor for reading and storing data, providing an exercising instruction to the operator, processing the performance of the exercising instruction by the operator, and saving the performance of the exercising instruction by the operator on the memory storage. More specifically the process of enabling an operator to exercise may include the steps of inserting a removable memory device into a processor for reading and storing data, providing an exercising instruction to the operator, processing the performance of the exercising instruction by the operator, measuring the weight of the operator, measuring the heart rate and the body fat of the operator, counting the number of plurality of weights displaced by the operator, and saving the weight and the heart rate and the body fat of the operator and the number of plurality of weights displaced and the performance of the exercising instruction by the operator on the removable memory device.

Figure 24:
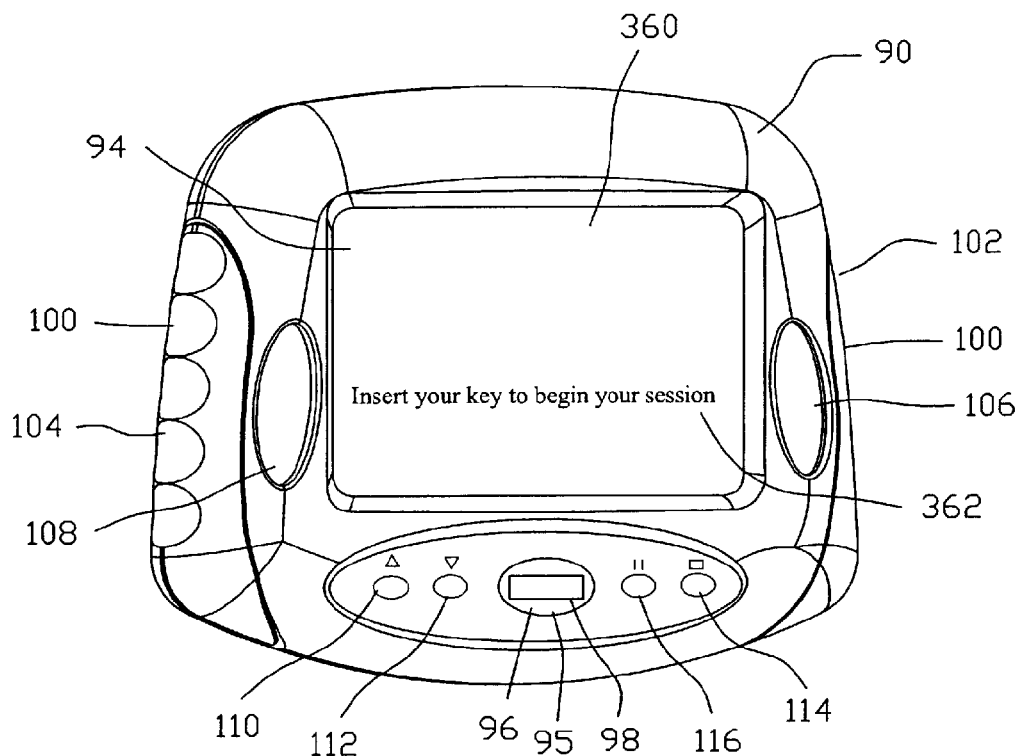
FIG. 24 is an enlarged view similar to FIG. 9.

FIG. 24 illustrates the liquid crystal touch screen display 94 of the user interface module 90 displaying a welcome screen 360. The welcome screen 360 include welcome text 362 instructing the operator 12 to insert the removable memory device 98 into the input port 95 to begin the operator's exercise program.

Figure 25:
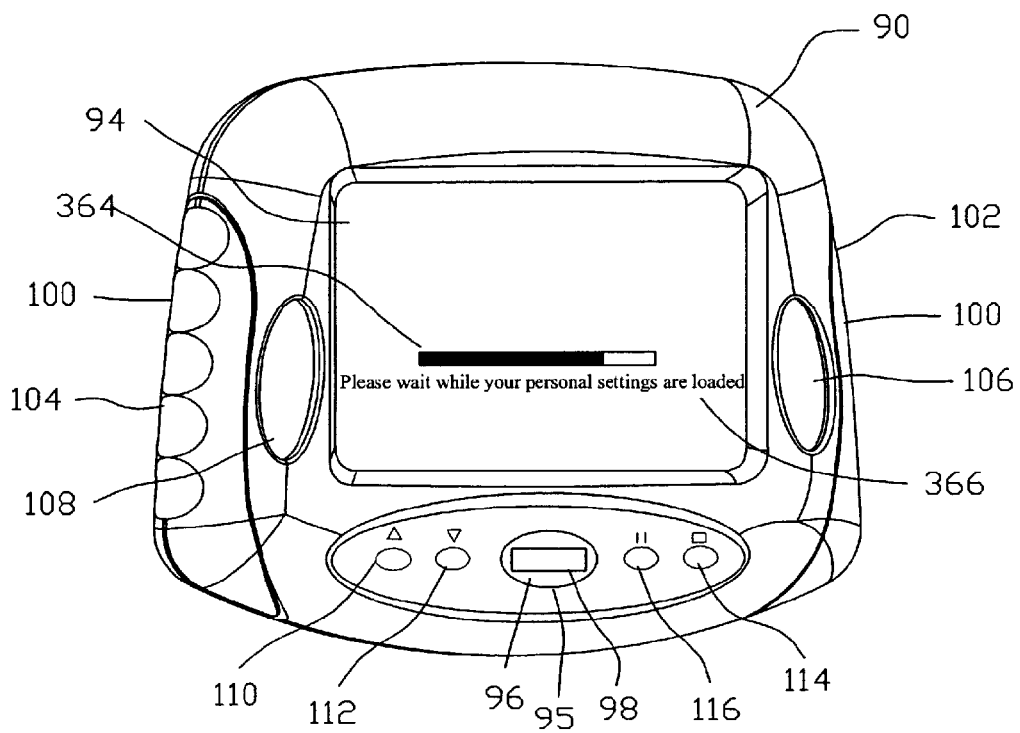
FIG. 25 is an enlarged view similar to FIG. 9.

FIG. 25 illustrates the liquid crystal touch screen display 94 displaying a data loading bar 364 and loading text 366 instructing the operator 12 to wait for data to be loaded. The insertion of the removable memory device 98 starts the application software and loads personal data and exercise programs into the user interface module 90.

Figure 26:
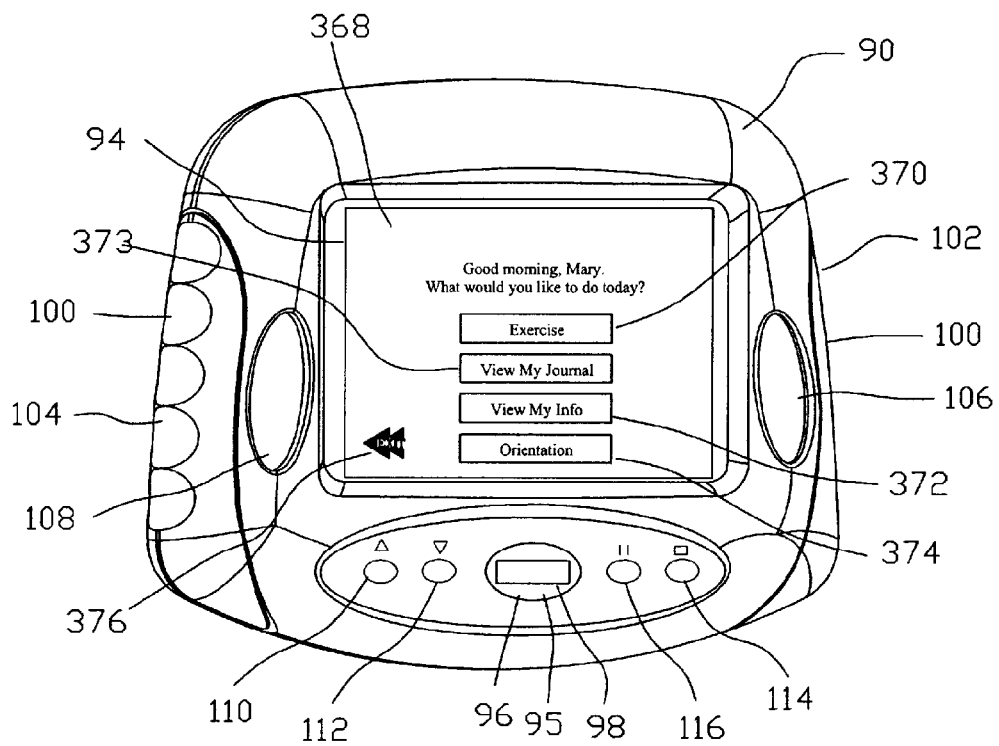
FIG. 26 is an enlarged view similar to FIG. 9.

FIG. 26 illustrates the liquid crystal touch screen display 94 displaying an option screen 368. The option screen 368 includes an exercise option 370 to begin exercising instructions, a journal option 372 to review the exercising history of the operator 12, a view information option 373 to review the operator's personal information and an orientation option 374 to review a tutorial on the operation of the apparatus 10. The option screen 368 also includes an exit function 376 to terminate the program.

Figure 27:
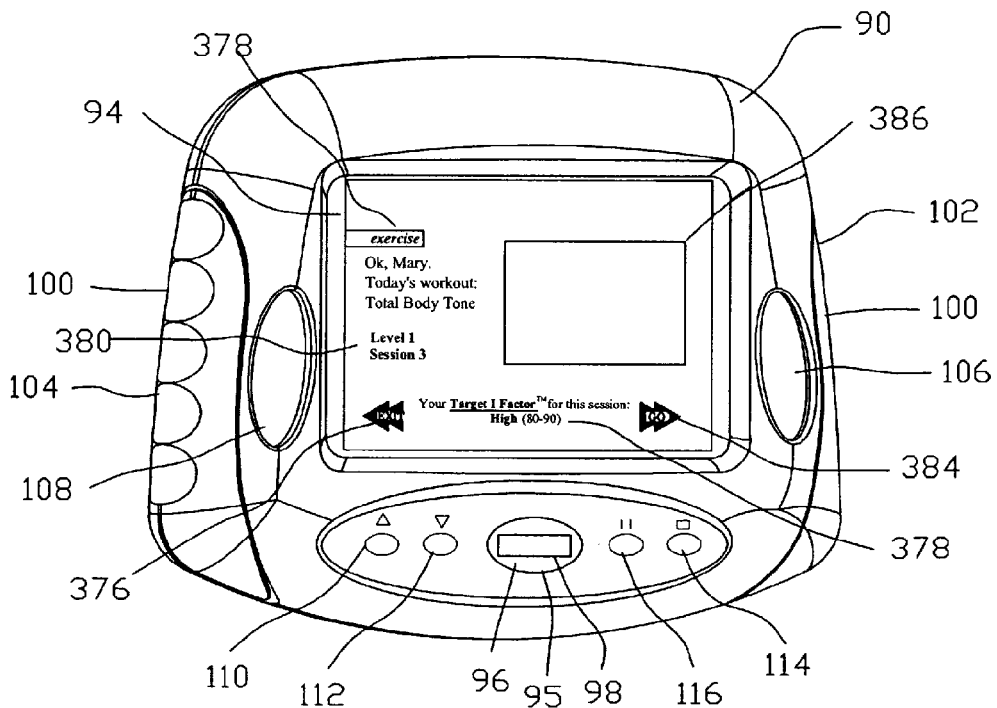
FIG. 27 is an enlarged view similar to FIG. 9.

FIG. 27 illustrates the liquid crystal touch screen display 94 displaying an exercising menu 378 to instruct the operator to begin utilizing the apparatus 10 to exercise. The exercising menu 378 includes an exercising intensity level indicator 380 to instruct the operator as to the difficult and number of the specific exercise. The exercising menu 378 also includes a target indicator 382 for disclosing an exercise parameter to be reached. The exercising menu 378 further includes a go function 384 for forwarding the program to the next exercise. The exercise menu 378 may also comprise an image portion 386 for displaying either a picture or a motion picture of an individual using the current exercise to illustrate the usage of the apparatus 10.

Figure 28:
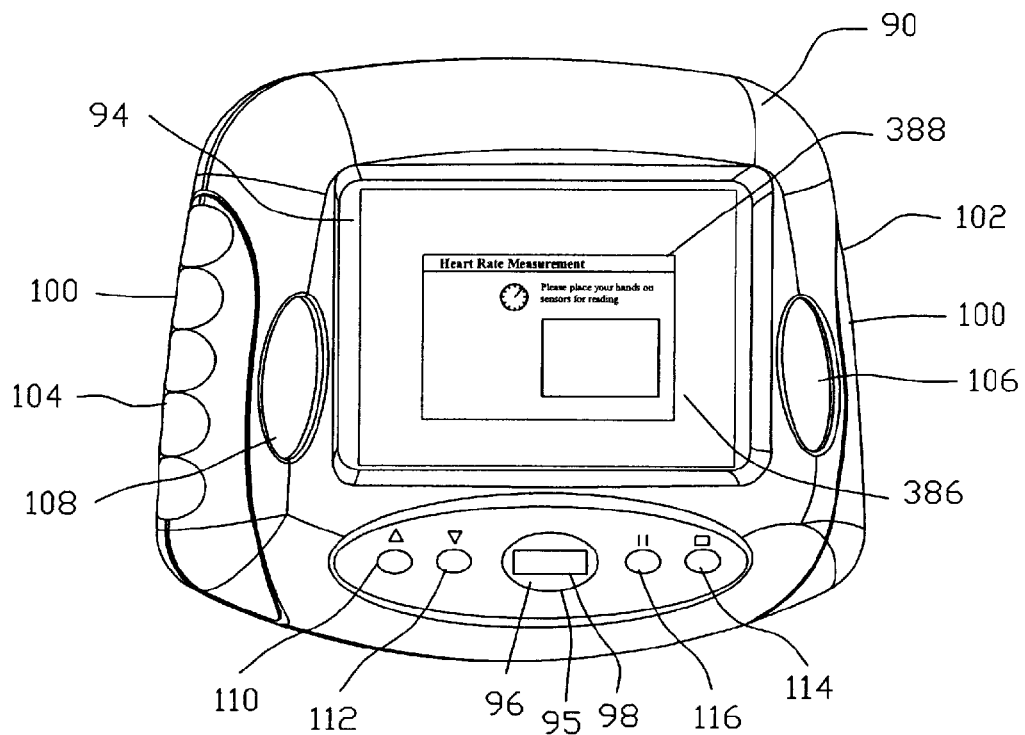
FIG. 28 is an enlarged view similar to FIG. 9.

FIG. 28 illustrates the liquid crystal touch screen display 94 displaying a heart rate menu 388. The heart rate menu 388 instructs the operator 12 to stop exercising and to place the operator's hands on the user interface module 280 with the hands contacting the first and second contact pads 102 and 104. The measuring of the operator's body fat is conducted similar to the measurement of the heart rate of the operator 12.

Figure 29:
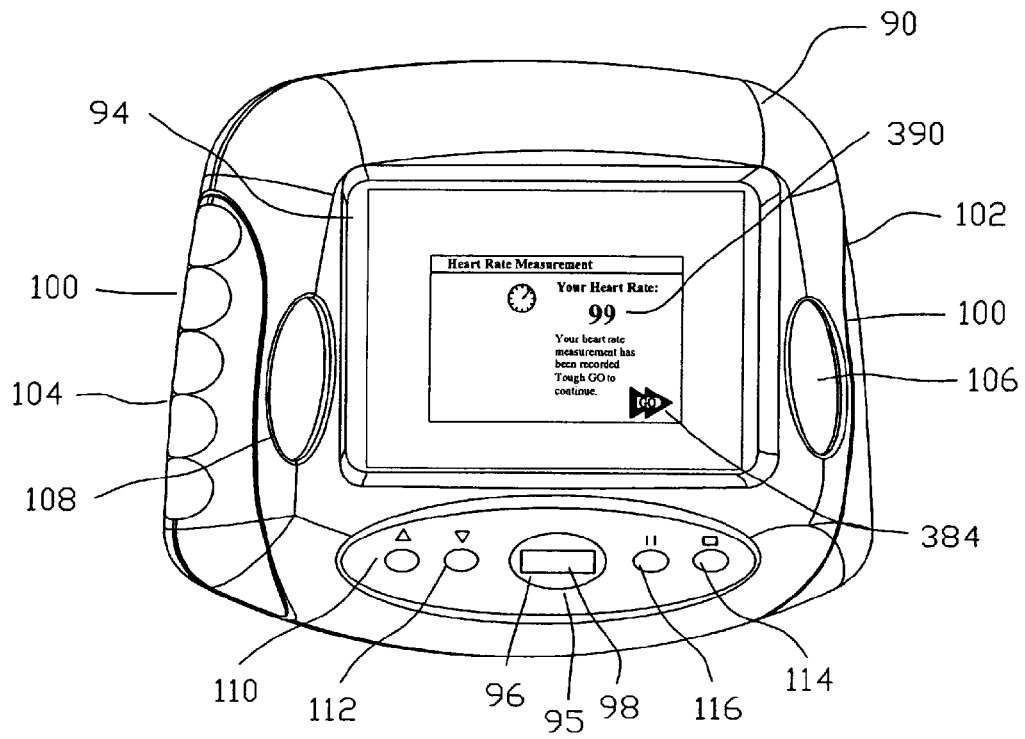
FIG. 29 is an enlarged view similar to FIG. 9.

FIG. 29 illustrates the liquid crystal touch screen display 94 displaying a heart rate menu 388. The heart rate menu 388 displays the operator's heart rate 390 and instructs the operator 12 to continue utilizing the apparatus 10 for exercising. The heart rate information is saves to the removable memory device 98.

Figure 30:
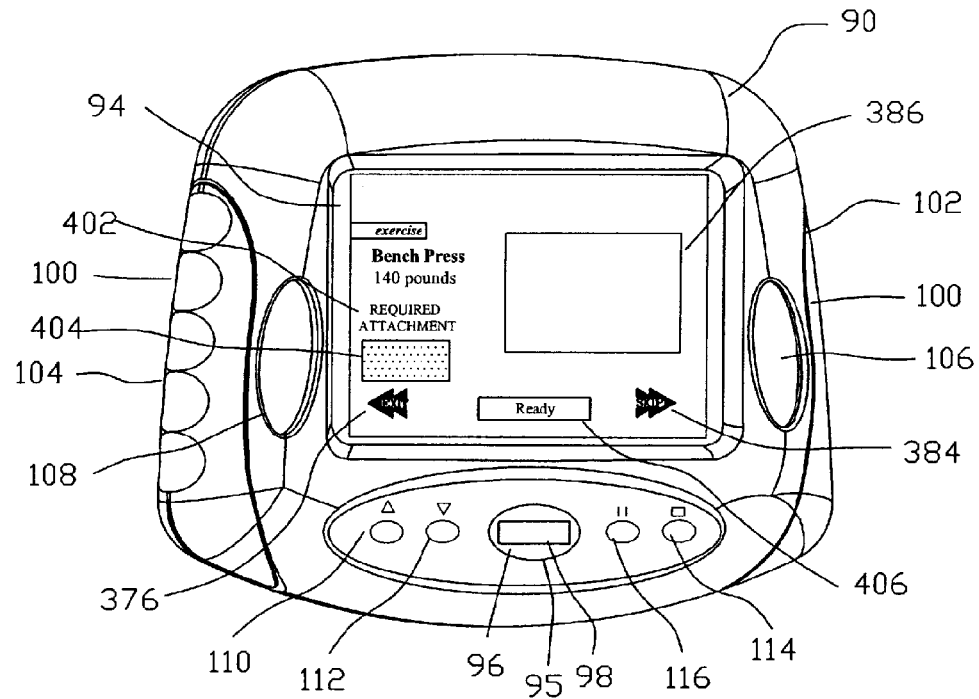
FIG. 30 is an enlarged view similar to FIG. 9.

FIG. 30 illustrates the liquid crystal touch screen display 94 displaying a second exercising menu 400 to instruct the operator 12 to begin utilizing the apparatus 10 to exercise. The second exercising menu 400 includes an attachment notification 402 for indicating an exercising attachment requirement for the next exercise. The attachment notification 402 may also include an image or motion picture of the exercising attachment 404. The second exercising menu 400 also includes a confirmation input 406 to confirm the exercising attachment is ready to be utilized.

Figure 31:
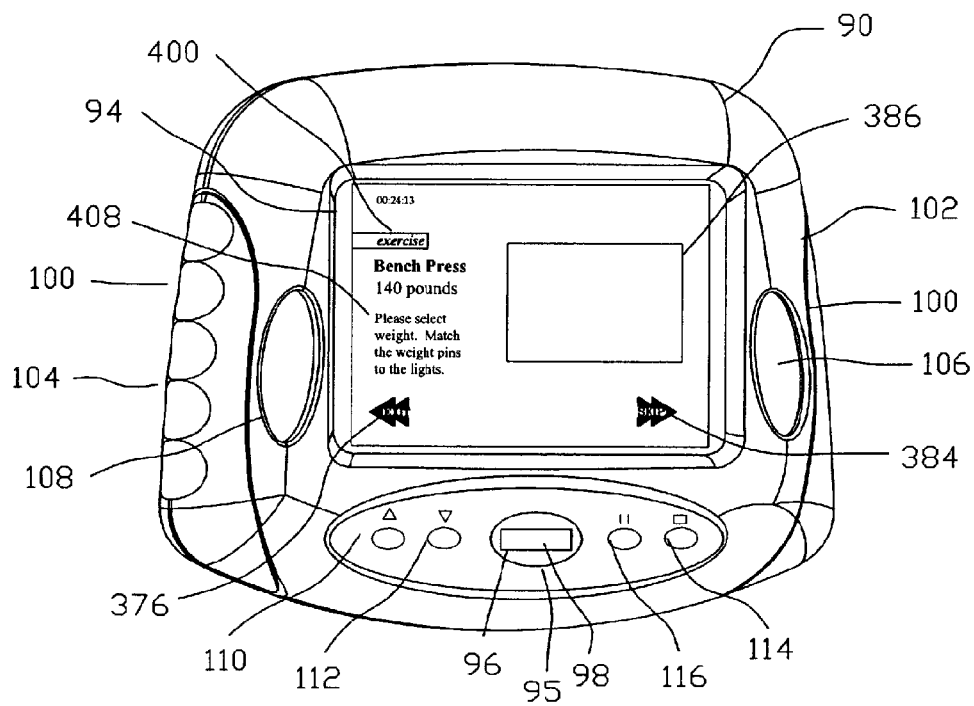
FIG. 31 is an enlarged view similar to FIG. 9.

FIG. 31 illustrates the liquid crystal touch screen display 94 displaying the second exercising menu 400 including a weight selection notification 408 to instruct the operator 12 to insert the pin 48 into one of the plurality of weights 40 which is adjacent to the flashing green bio-colored LED 262.

Figure 32:
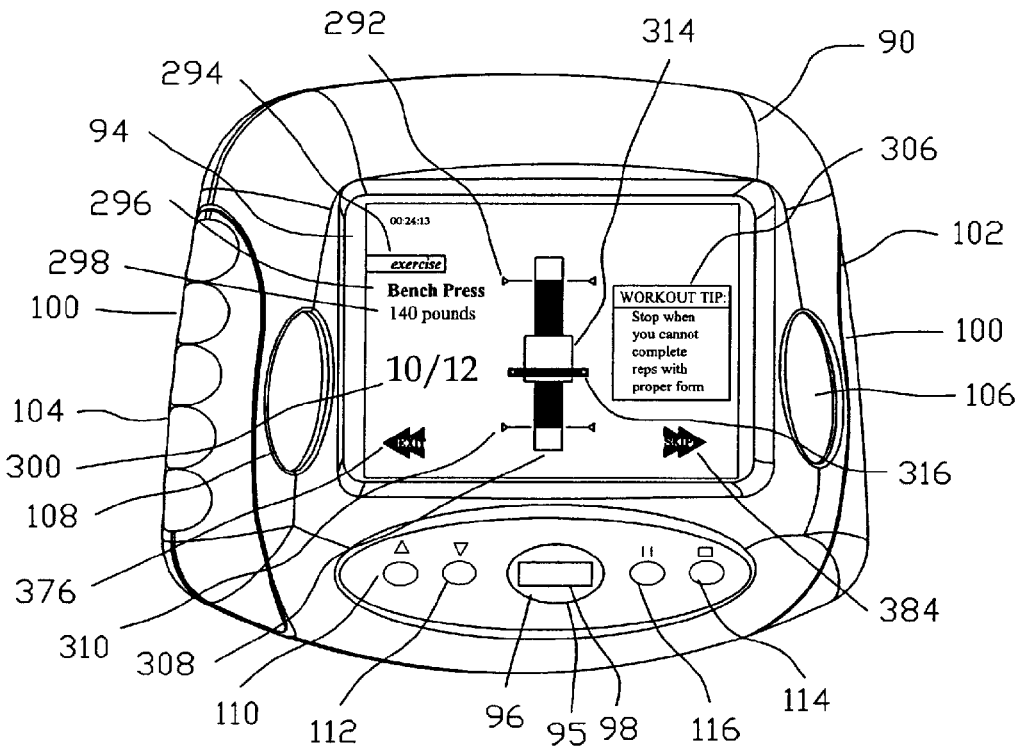
FIG. 32 is an enlarged view similar to FIG. 9.

FIG. 32 is similar to FIGS. 21 and 22 which illustrates the liquid crystal touch screen display 94 displaying visual data for illustrating the displacement and the speed of the linkage 80 with respect to a predetermined standard in real time. More specifically, the visual data includes a rate of executed exercise 308 including a lower range of exercise 310 and an upper range of exercise 312. The exercising instruction 294 may further include an exercising notice 306 instructing the operator 12 to terminate exercising the current exercising instruction 294 once the operator 12 can not maintain the operator pace bar 316 within the pace bar 314.

Figure 33:
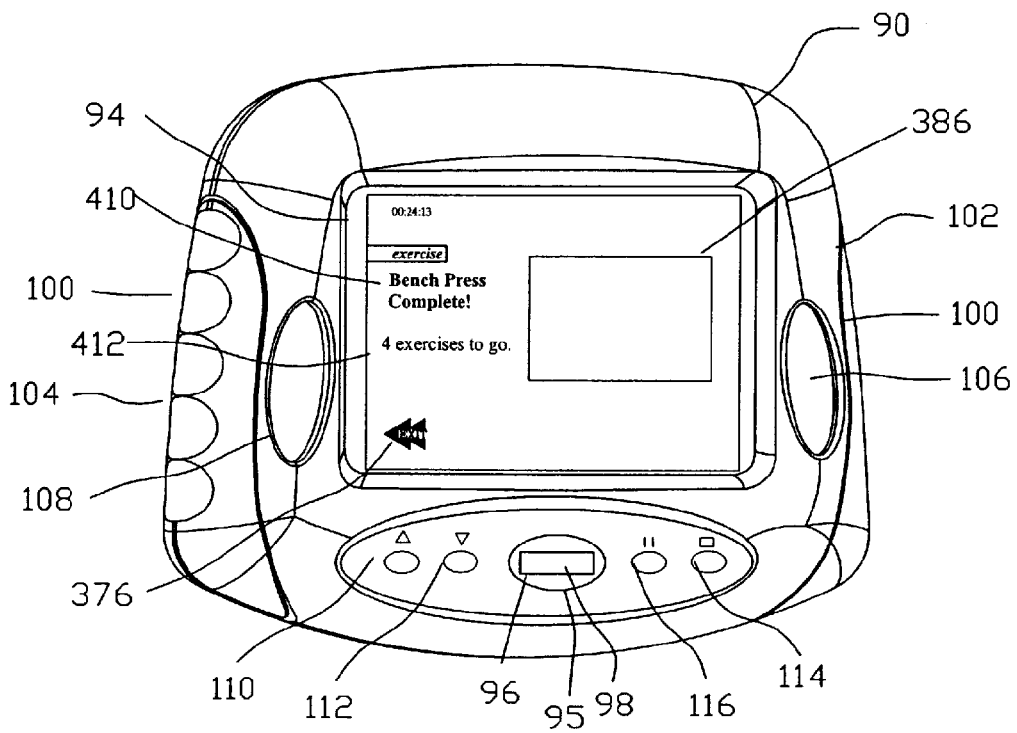
FIG. 33 is an enlarged view similar to FIG. 9.

FIG. 33 illustrates the liquid crystal touch screen display 94 displaying a termination menu 410 for a specific exercise. The termination of a specific exercise menu 410 including a notification of any remaining exercises to be completed 412.

Figure 34:
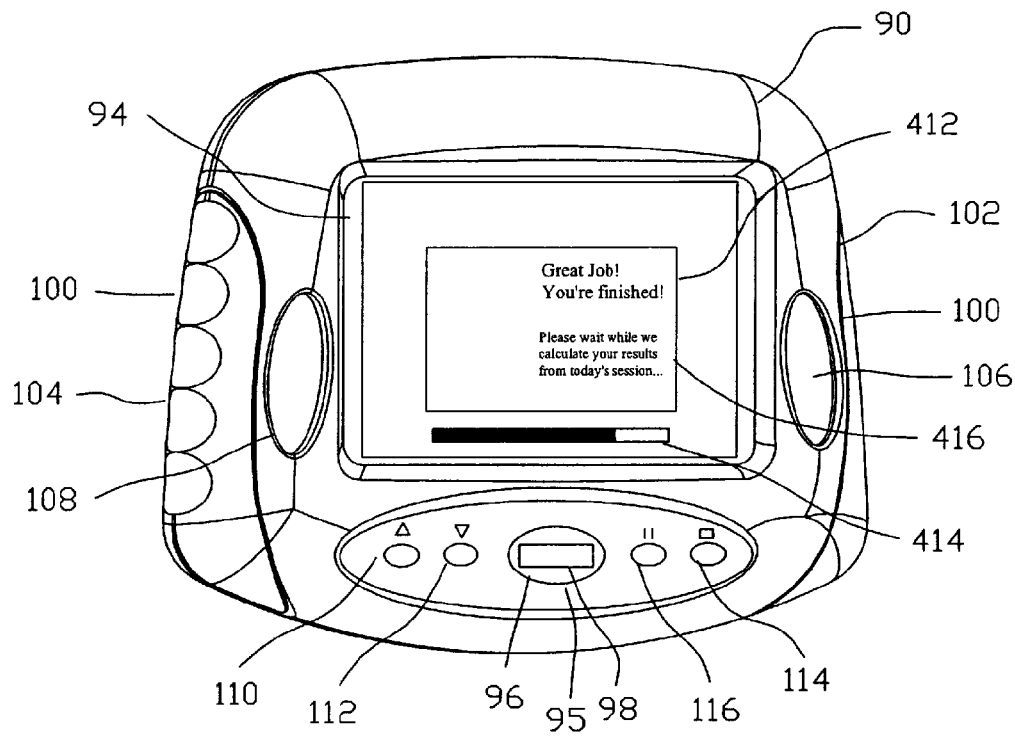
FIG. 34 is an enlarged view similar to FIG. 9.

FIG. 34 illustrates the liquid crystal touch screen display 94 displaying a second termination menu 412 indicating termination of all exercises. The second termination menu 412 includes a data calculating bar 414 and calculating text 416 instructing the operator 12 to wait for data to be calculated.

Figure 35:
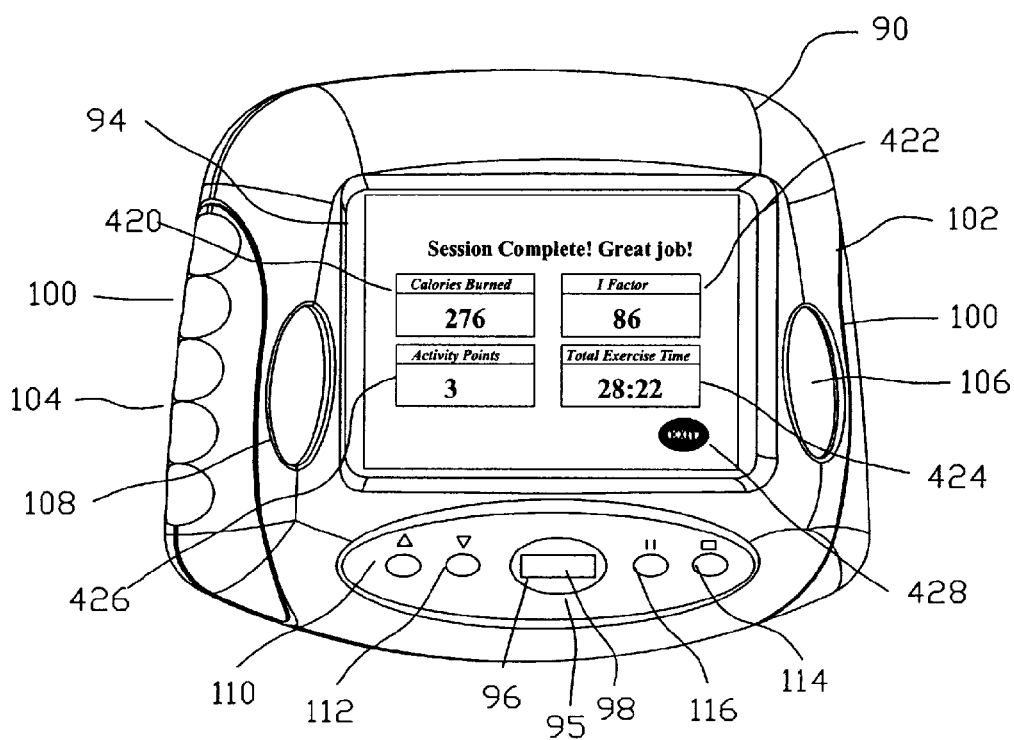
FIG. 35 is an enlarged view similar to FIG. 9.

FIG. 35 illustrates the liquid crystal touch screen display 94 displaying a performance menu 418. The performance menu 418 includes the calculations for calories burned 420, targeted heart rate 422, total exercise time 424 and points acquired 426 for the exercise session. The performance menu also includes an exit function 428 for terminating the performance menu.

Figure 36:
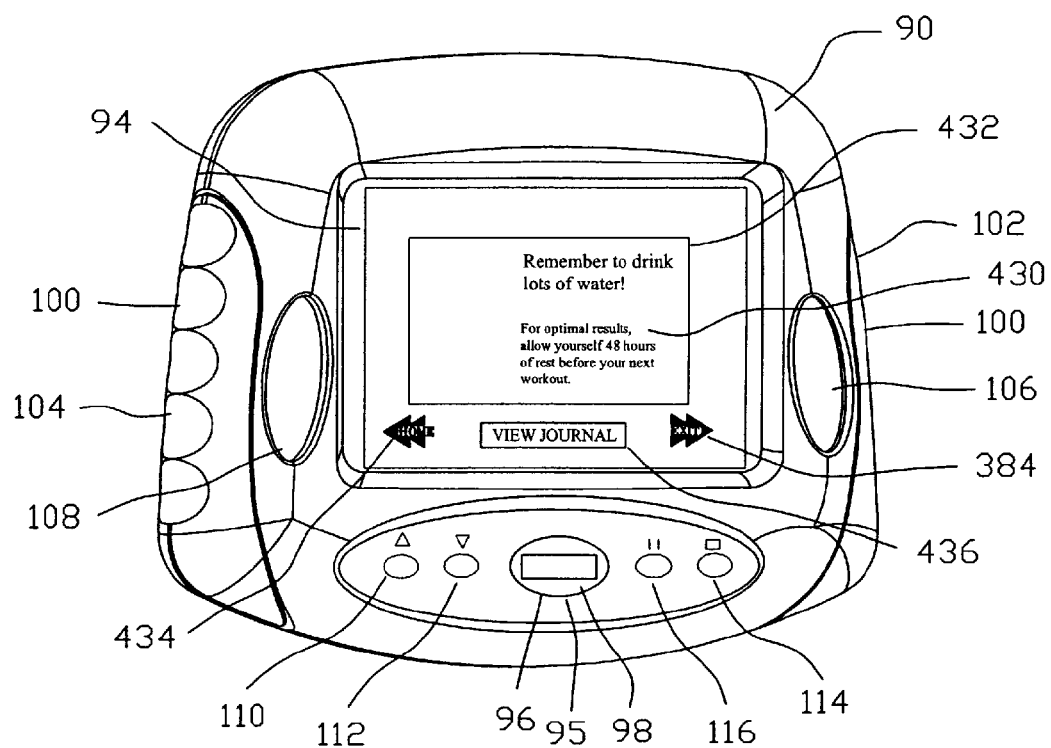
FIG. 36 is an enlarged view similar to FIG. 9.

FIG. 36 illustrates the liquid crystal touch screen display 94 displaying a scheduling menu 430 for the operator to return for the next exercise session. The scheduling menu 430 includes a notice 432 to include pertinent information such as to consume water after exercising. The scheduling menu 430 may also include a home function 434 and a journal function 436. The home function 434 returns the program to the main menu. The journal function 436 forwards the program to a journal menu.

Figure 37:
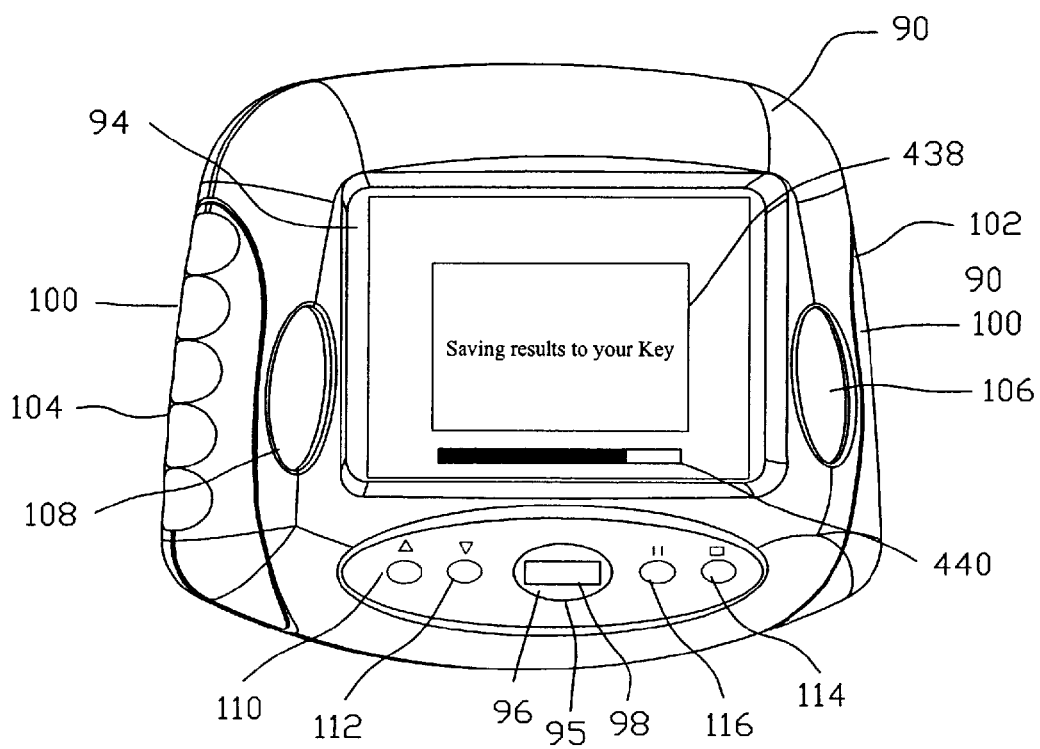
FIG. 37 is an enlarged view similar to FIG. 9.

FIG. 37 illustrates the liquid crystal touch screen display 94 displaying a saving menu 438 for indicating data being stored on the removable memory device 98. The saving menu 438 includes a storage bar 440 for instructing the operator 12 to wait for data to be stored on removable memory device 98.

Figure 38:
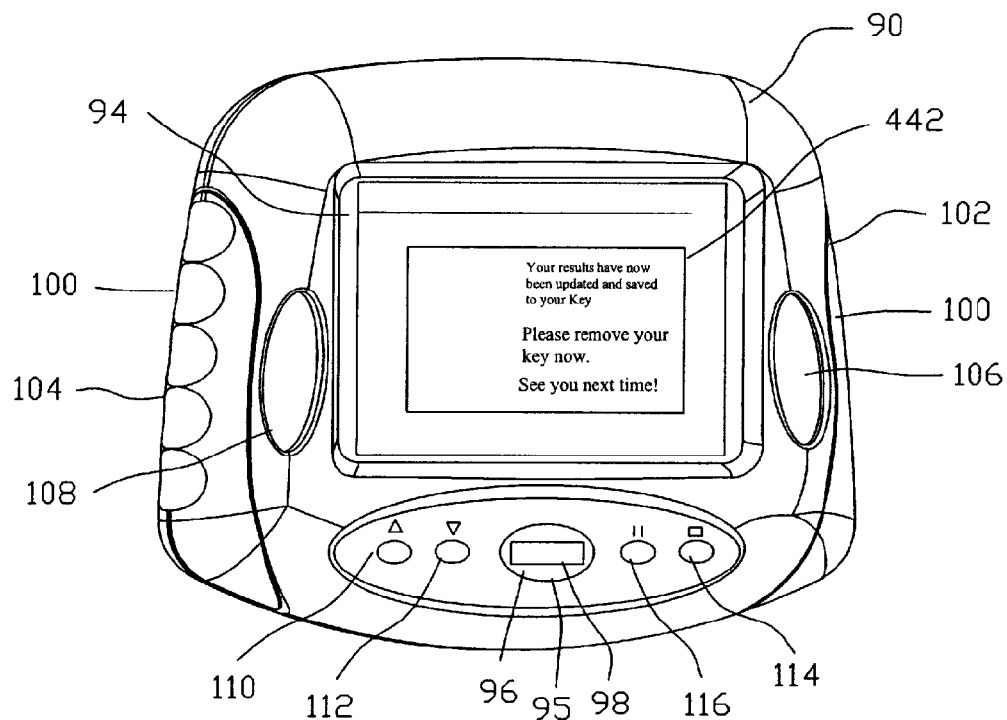
FIG. 38 is an enlarged view similar to FIG. 9.

FIG. 38 illustrates the liquid crystal touch screen display 94 displaying a conclusion menu 442 for instructing the operator 12 to remove the removable memory device 98.

Figure 39:
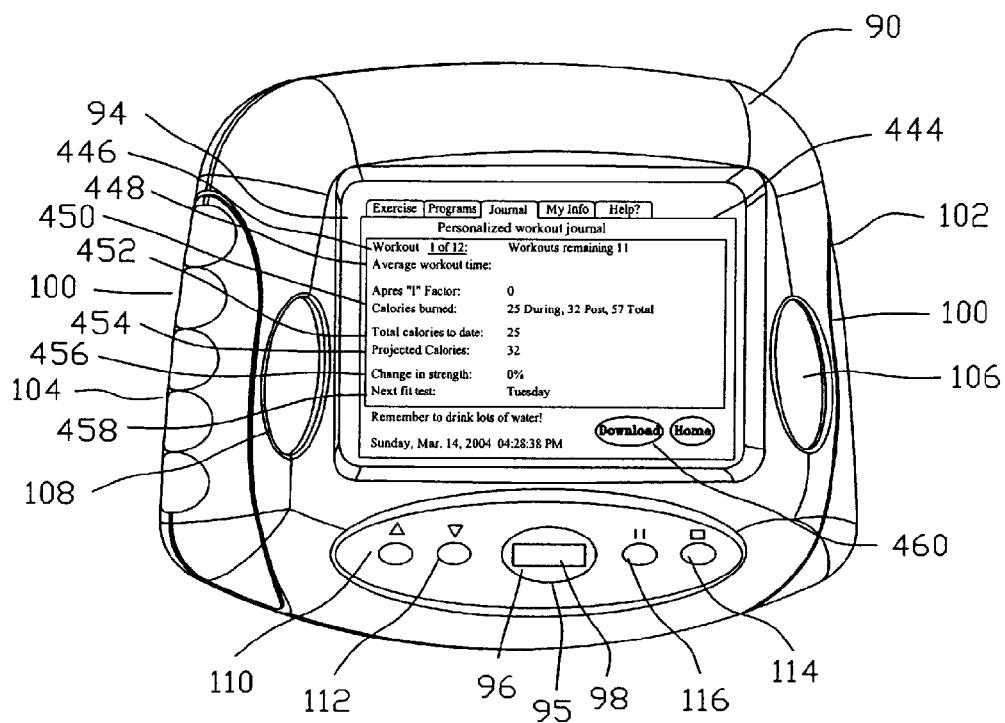
FIG. 39 is an enlarged view similar to FIG. 9.

FIG. 39 illustrates the liquid crystal touch screen display 94 displaying a first journal menu 444 including a review the exercising history and future exercise sessions to be conducted by the operator 12. The first journal menu 444 may comprise: number of workout 446, average workout time 448, calories burned 450, total calories to date 452, projected calories 454, change in strength 456, and next fit test 458. The first journal menu 444 may also include a download function 460 to transfer the journal data to the removable memory device 98.

Figure 40:
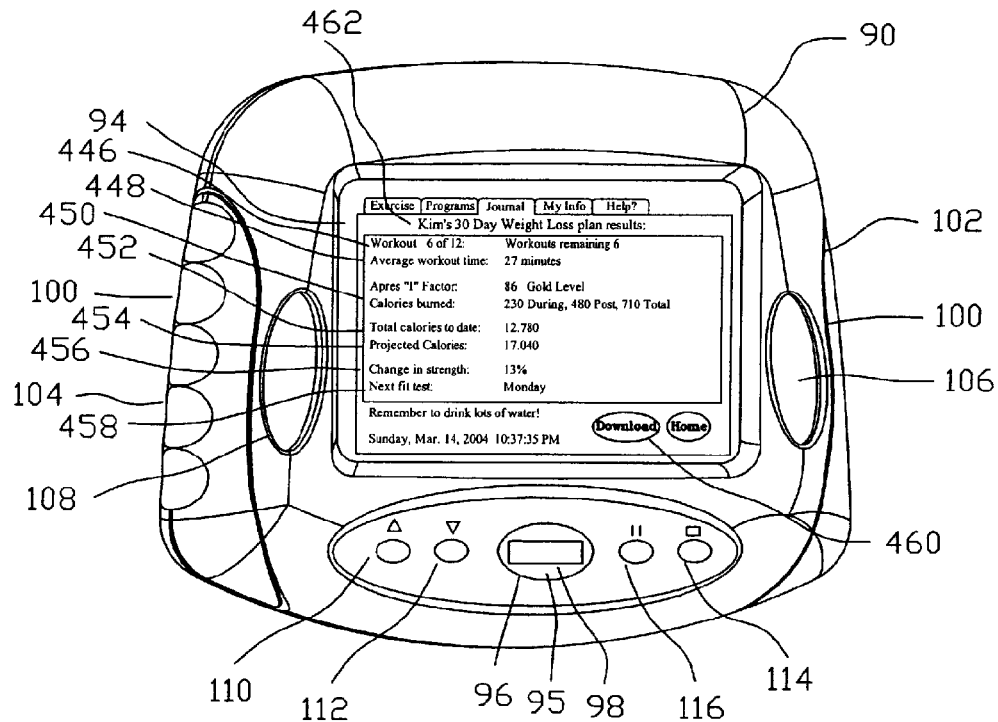
FIG. 40 is an enlarged view similar to FIG. 9.

FIG. 40 is a similar view of FIG. 39 displaying a second journal menu 462. The second journal menu 462 comprises an exercising schedule including a 30 day weight loss plan for the operator 12.

Figure 41:
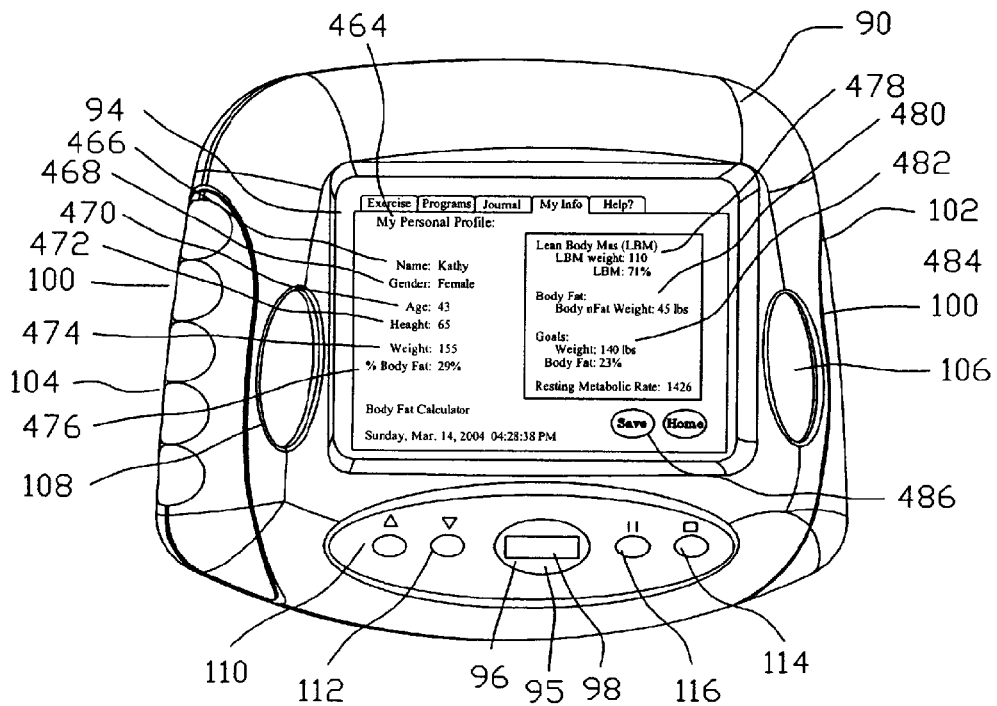
FIG. 41 is an enlarged view similar to FIG. 9.

FIG. 41 illustrates the liquid crystal touch screen display 94 displaying a personal information menu 464. The personal information menu 464 comprises the operator's personal profile including name 466, gender 468, age 470, height 472, weight 474, percent body fat 476, lean body mass 478, body fat 480, goals 482 and resting metabolic rate 484. The personal information menu 464 may also include a save function 486 to save the operator's profile to the removable memory device 98.

FIGS. 42-49 illustrate a second embodiment of the subject invention. An apparatus 500 enables an operator to exercise. The apparatus 500 includes a frame 502 having a body 504, a base 506 and a top 508. The body 504 includes a first frame coupling 510 and a second frame coupling 512 interposed between the base 506 and the top 508.

A load 514 is positioned on the frame 502 for providing a resistive force. A press 516 is positioned on the frame 502 for displacement by the operator. A linkage 518 joins the load 514 with the press 516 for displacing the load 514 upon displacement of the press 516 by the operator.

An arm 530 extends between a support end 532 and a user end 534. The arm 530 has an interior chamber 536 and extends from a first end 538 to a second end 540. The arm 530 may include a cylindrical tube 542 having a ninety degree bend 544 for forming a generally L-shape 546. Preferably, the arm 530 is constructed from a metallic material such as steel or aluminum.

As best seen in FIGS. 42-54 the arm 530 is attached to the top 508 of the frame 502 by a support pivot 560. The support pivot 560 secures the support end 532 of the arm 530 to the top 508 of the frame 502. The support pivot 560 permits the arm 530 to pivot about the frame 502 for positioning the user end 534 in multiple positions relative to the apparatus 500. The support pivot 560 includes a cylindrical body 562 defining an interior chamber 564 extending between a first end 566 and a second end 568. Preferably, the support pivot 560 is constructed from a metallic material such as steel or aluminum. The cylindrical body 562 has an arm aperture 570 for engaging the first end 538 and allowing a continuous conduit 572 from the arm 530 to the interior of the support pivot 560. The support pivot 560 and the arm 530 may be fused by welding.

The support pivot 560 further includes a pin receiver 574 including a cylindrical body 575 defining an interior chamber 576 extending between a first end 578 and a second end 580. Preferably, the pin receiver 574 is constructed from a metallic material such as steel or aluminum. The pin receiver 574 is secured within the interior chamber 564 of the cylindrical body 562 by a first support plate 582 and a second support plate 584. Both the first support plate 582 and the second support plate 584 extend between the pin receiver 574 and the support pivot 560 for securing the pin receiver 574 within the interior chamber 564 of the cylindrical body 562. The first support plate 582 is positioned at the first end 578 of the pin receiver 574 and the second support plate 584 is positioned at the second end 580 of the pin receiver 574. Preferably, the first and second support plates 582 and 584 are constructed from a metallic material such as steel or aluminum. Both the first support plate 582 and second support plate 584 are secured between the pin receiver 574 to the cylindrical body 562 of the support pivot 560 by welding or other fastening.

The first support plate 582 includes a first opening 588 and the second support plate 584 includes a second opening 590. The first and second openings 588 and 590 may be created by removing a portion of the first support plate 582 and second support plate 584 respectively. The first and second openings 588 and 590 permit an electrical conductor 589 to traverse from the interior chamber 536 of the arm 530 and through the support pivot 560 and still allow the arm 530 to pivot about the frame 502 for positioning the user end 534 in multiple positions relative to the apparatus 500.

A first bearing 592 is positioned within the first end 578 of the pin receiver 574. A second bearing 594 is positioned within the second end 580 of the pin receiver 574. The first and second bearings 592 and 594 may include a thrust bearing 596. The first and second bearings 592 and 594 receive a pin 598 for pivotably mounting the support pivot 560 to the top 508 of the frame 502.

The top 508 of the frame 502 includes a rectangular cylindrical body 610 having a top face 612 and a bottom face 614. The top face 612 has a top aperture 616 and the bottom face 614 has a bottom aperture 618. Preferably, the rectangular cylindrical body 610 is constructed from a metallic material such as steel or aluminum. The top face 612 may further include a conductor aperture 619 for permitting the electrical conductor 589 to traverse from the support pivot 560 and into the top 508 of the frame 502 still allow the arm 530 to pivot about the frame 502 for positioning the user end 534 in multiple positions relative to the apparatus 500.

The pin 598 has a cylindrical body 600 extending between a first end 602 and a second end 604. The first end 602 includes a ledge 606 that divides the cylindrical body 600 from a thread surface 608. A bearing ledge 601 divides the pin 598 between a first pin diameter 603 and a second pin diameter 605. The first pin diameter 603 is smaller than the second pin diameter 605. The first pin diameter 603 is sized to traverse through the first and second bearings 592 and 594. The second pin diameter 605 is sized to abut the second bearing 594 for supporting the support pivot 560. The second pin diameter 605 is sized to slidably engage the top aperture 618 and the bottom aperture 619 of the rectangular cylindrical body 610. The second end 604 may include a step 607 for engaging the bottom aperture 618. The step 607 permits a portion of the second end 604 of the pin 598 to traverse into the bottom aperture 618 for preventing lateral movement of the second end 604 of the pin 598 relative to the bottom face 614. The length of the pin 598 having the second pin diameter 605 is greater than the distance from the bottom face 614 to the top face 612 for positioning the bearing ledge 601 above the face 612. The length of the pin 598 having the first pin diameter 603 is greater than the distance from the first bearing 592 and the second bearing 594 for positioning the thread surface 608 above the first bearing 592.

The pin 598 is inserted into the top 508 by inserting a second end 604 first through the top aperture 616 and in engagement with the step receiver 617. The second end 604 is secured to the bottom face 614 by a weld 620. The first and second bearings 592 and 594 are slidably engaged over the first pin diameter 603 until the second bearing 594 abuts the bearing ledge 601. The pin 598 traverses through the top 612 of the frame 502 and through the second bearing 594 and the first bearing 592 of the pin receiver 574 to pivotably mount the support pivot 560 to the top 508 of the frame 502.

A nut 609 threadably engages the thread surface 608 for applying a compressive force between the pin receiver 574 and the pin 598. A cap 628 may be engaged into the first end 566 of the support pivot 560 for covering the interior chamber 564 of the support pivot 560.

The support pivot 560 may also include a stop plate 650 having a first stop surface 652 and a second stop surface 654 extending from the second end 568 of cylindrical body 562.

Preferably, the cylindrical body 562 and the first and second stop surfaces 652 and 654 are an integral one-piece unit. A stop pin 656 extends from the top face 612 of the rectangular cylindrical body 610. The stop pin 656 contacts the first stop surface 652 for terminating the rotation of the arm 530 in a first arm position 660. The stop pin 656 contacts the second stop surface 654 for terminating the rotation of the arm 530 in a second arm position 662.

The support pivot 560 may also include a brake plate 670 extending from the second end 568 of cylindrical body 562. Preferably, the cylindrical body 562 and the brake plate 670 are an integral one-piece unit. A brake 672 extends from the top 508 of the frame 502 for contacting the brake plate 670 for restricting the rotational speed of the arm 530. The brake 672 further includes a brake housing 674 having a cylindrical body 676 defining an interior chamber 678 extending between a closed end 680 and a brake aperture 682. A brake pad 684 slidably engages along the interior chamber 678 of the brake housing 674. A brake spring 686 applies a compressive force between the closed end 680 and the brake pad 684 for pressing the brake pad 684 against the brake plate 670 for restricting the rotational speed of the arm 530. The brake pad 684 may include a polymeric material or other rigid material.

Figures 44, 45:
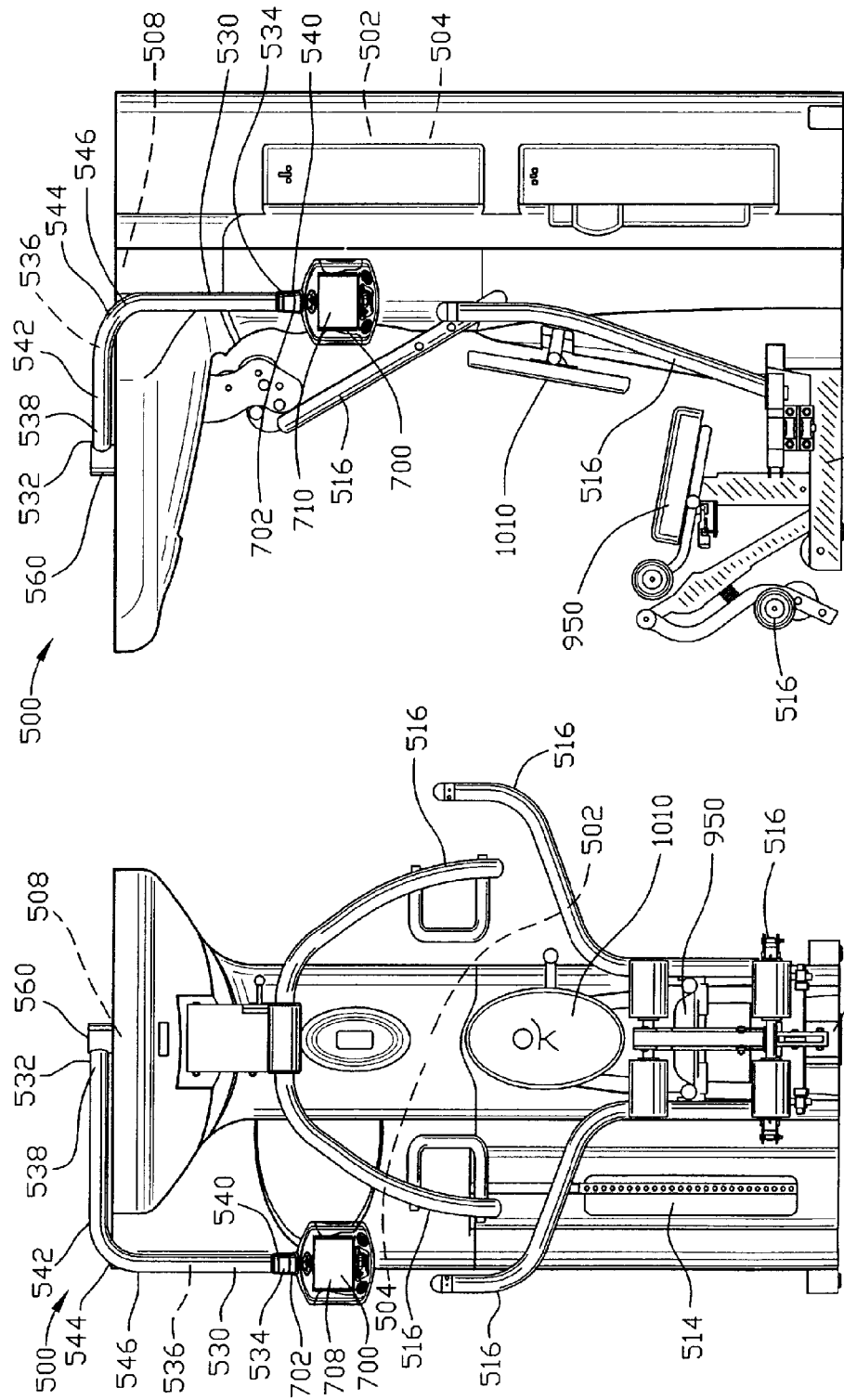
FIG. 44 is a view similar to FIG. 42 illustrating the arm and the user interface in an alternative position.
FIG. 45 is a right side view of FIG. 42 illustrating the arm and the user interface in an alternative position.
Figures 46, 47:
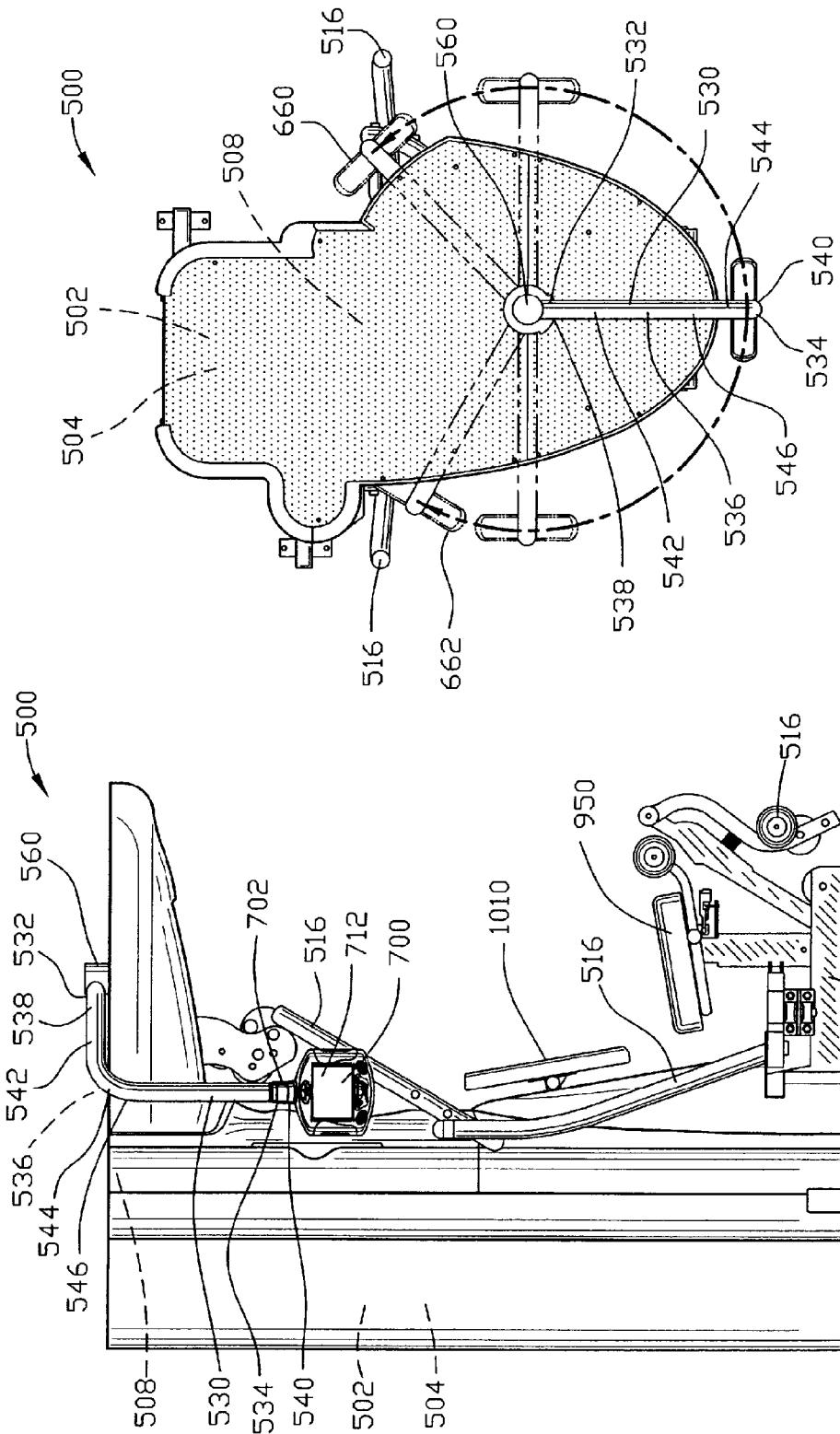
FIG. 46 is a left side view of FIG. 42 illustrating the arm and the user interface in an alternative position.
FIG. 47 is a top view of FIG. 42 illustrating the arm and the user interface in alternative positions.
Figure 49:
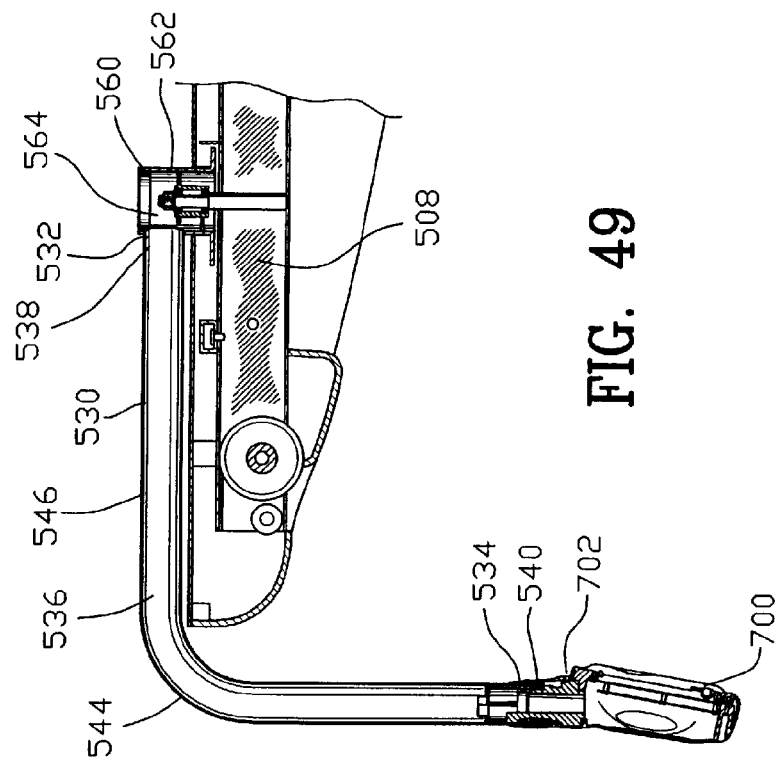
FIG. 49 is a magnified view of a portion of FIG. 48.
Figure 48:
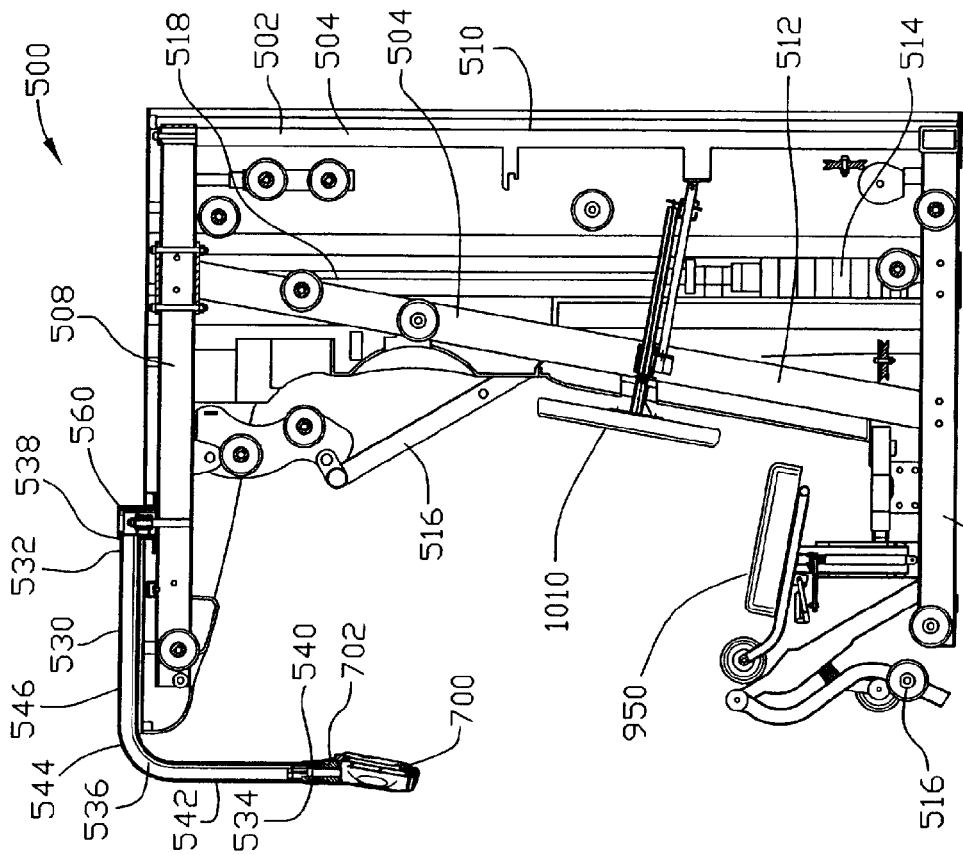
FIG. 48 is a sectional view along line 48-48 in FIG. 42.
Figures 52, 53:
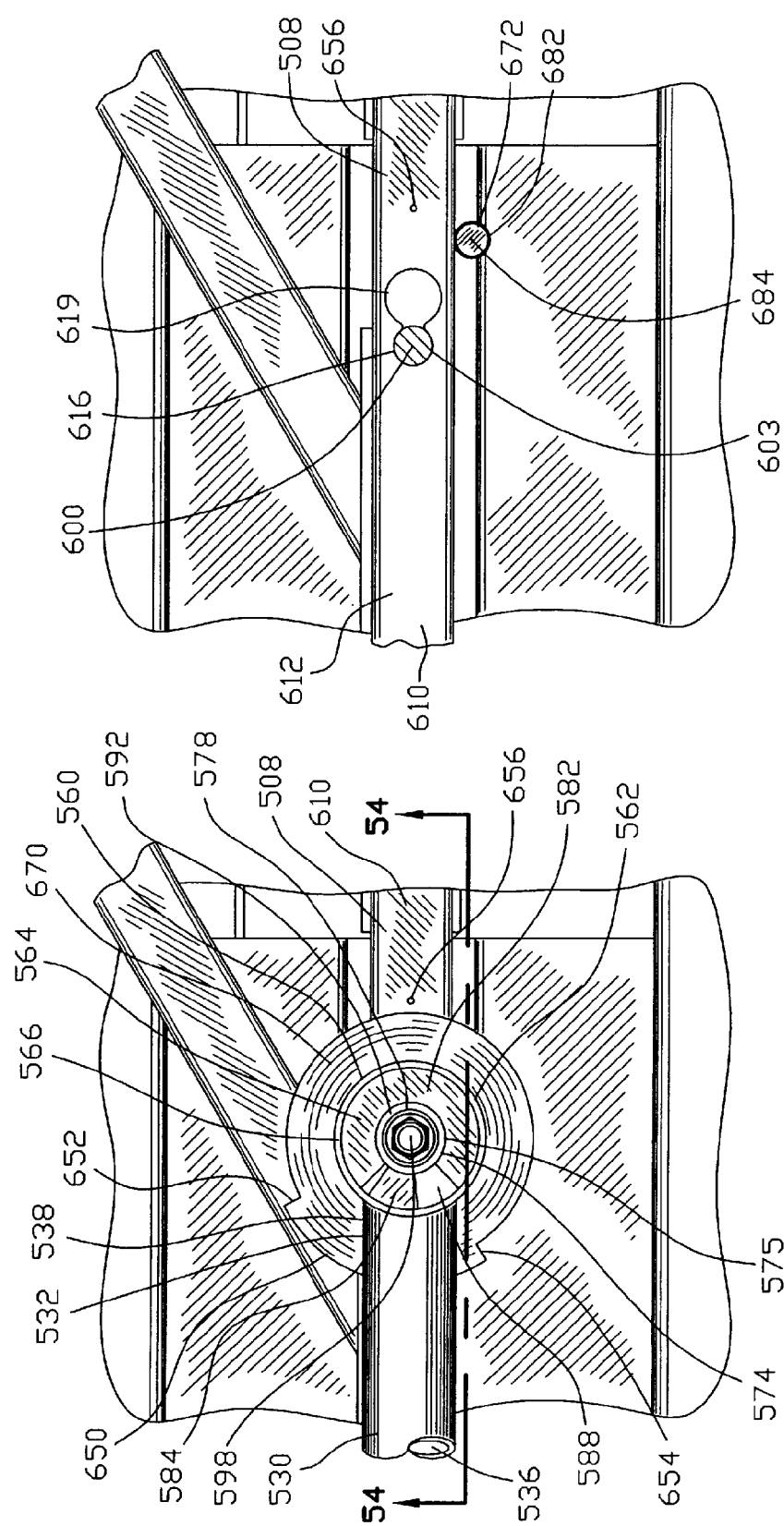
FIG. 52 is a sectional view along line 52-52 in FIG. 50.
FIG. 53 is a sectional view along line 53-53 in FIG. 50.
Figure 54:
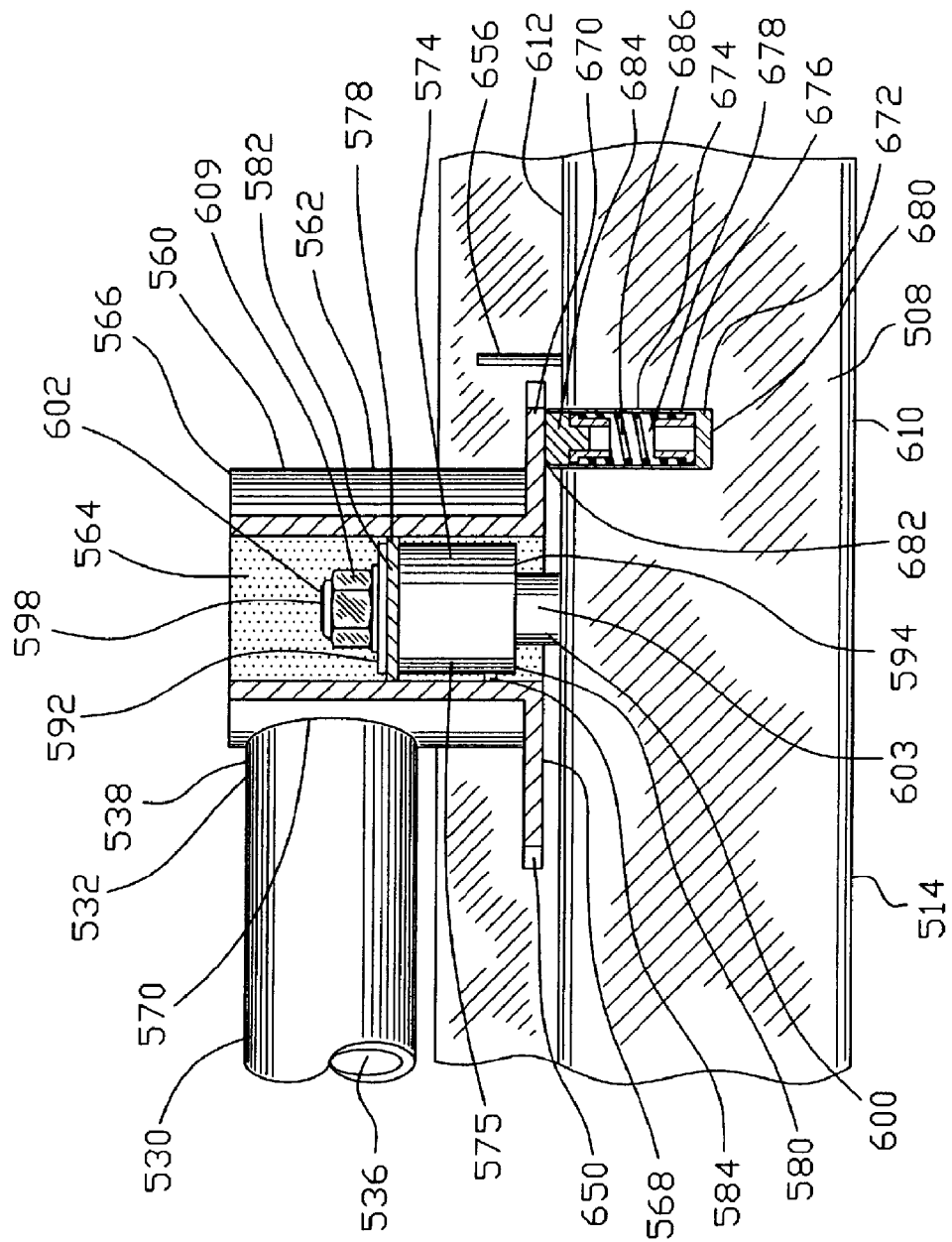
FIG. 54 is a sectional view along line 54-54 in FIG. 50.
Figure 60:
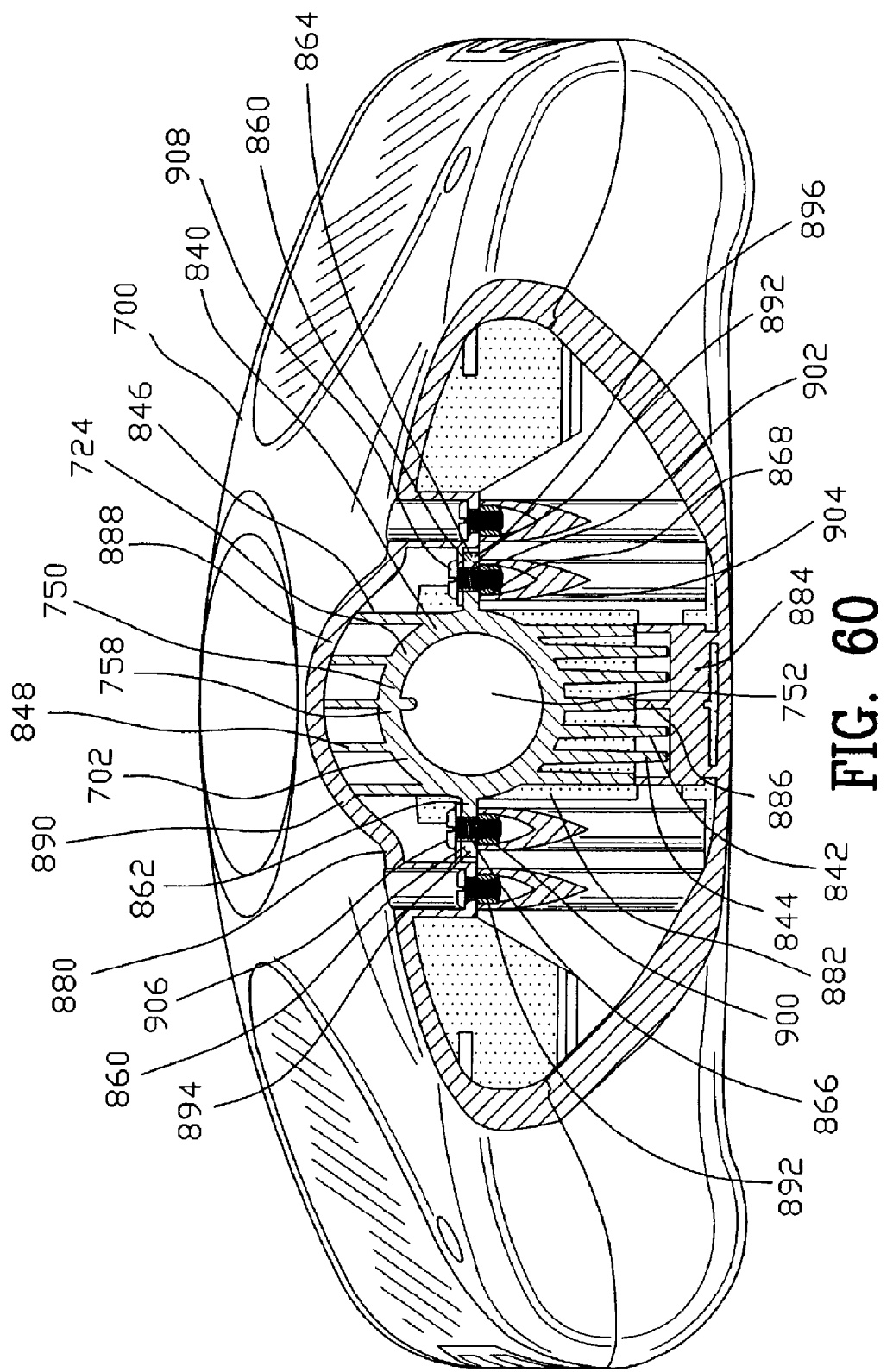
FIG. 60 is a sectional view along line 60-60 in FIG. 55.
Figure 63:
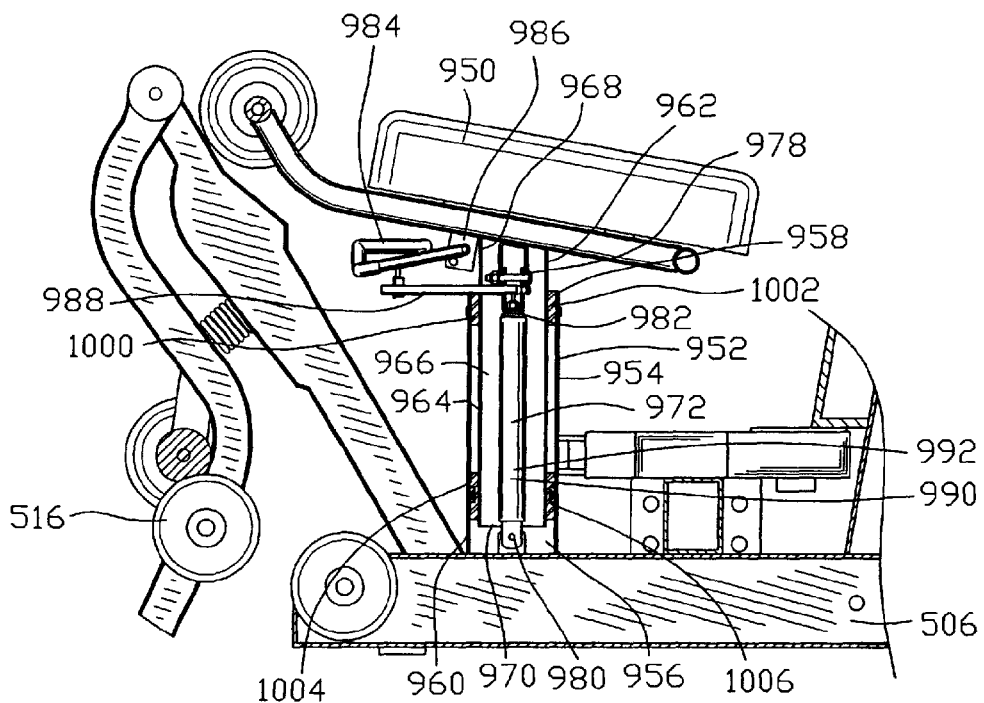
FIG. 63 is a sectional view along line 63-63 in FIG. 44.
Figure 64:
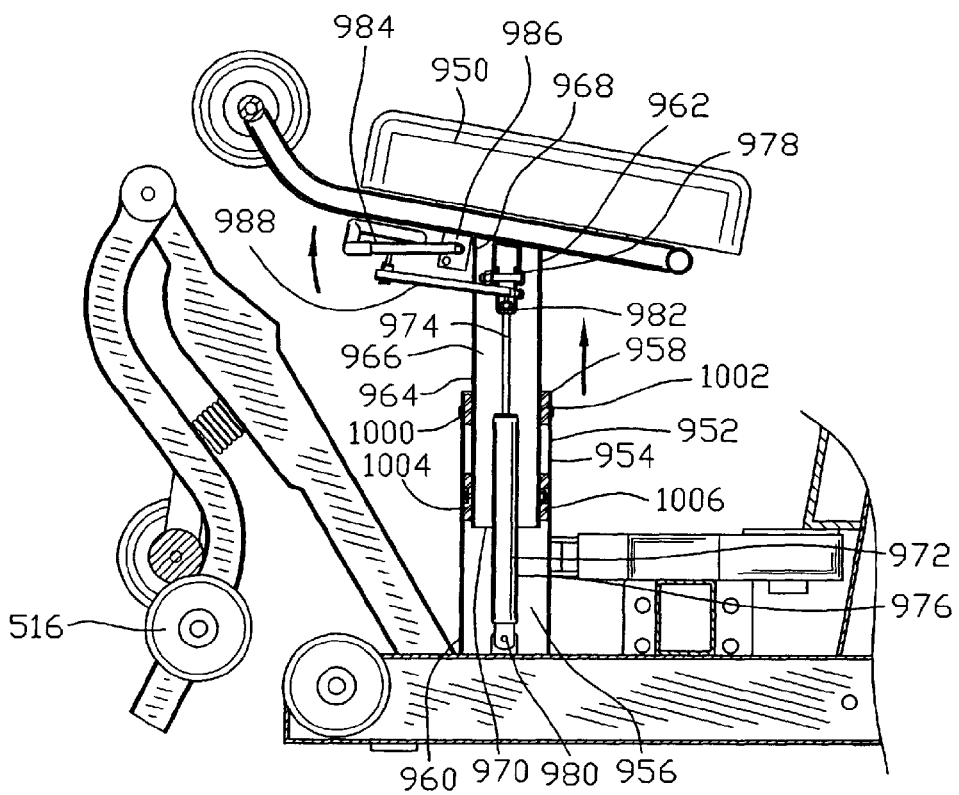
FIG. 64 is a view similar to FIG. 63 illustrating the seat and backseat positioned in the second position.
Figure 65:
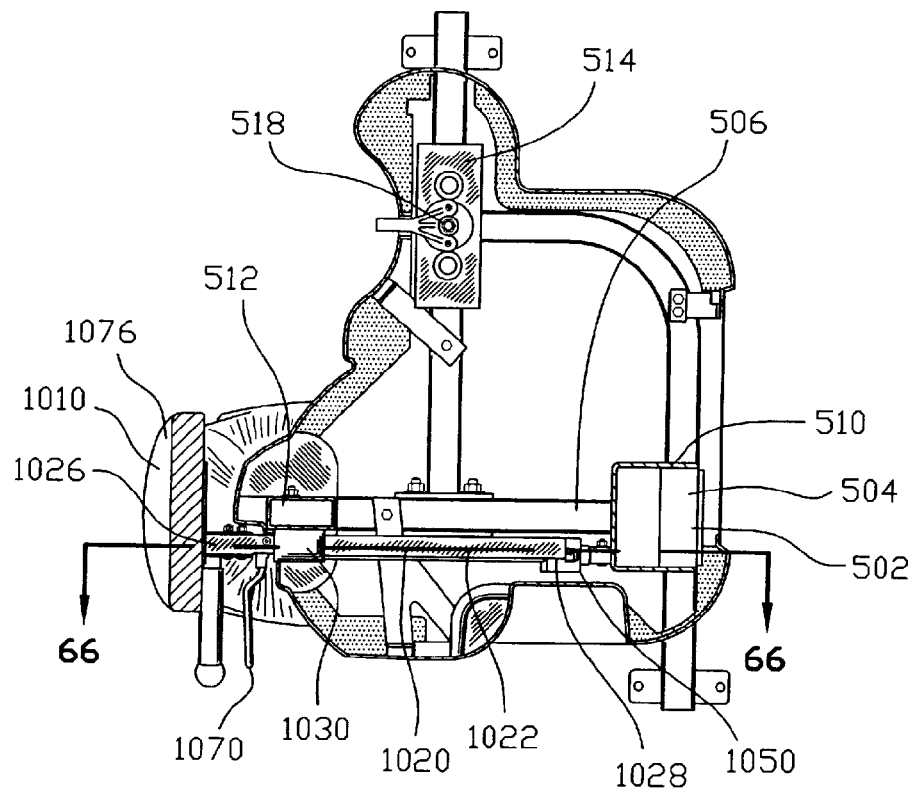
FIG. 65 is a bottom view of FIG. 61.
Figure 66:
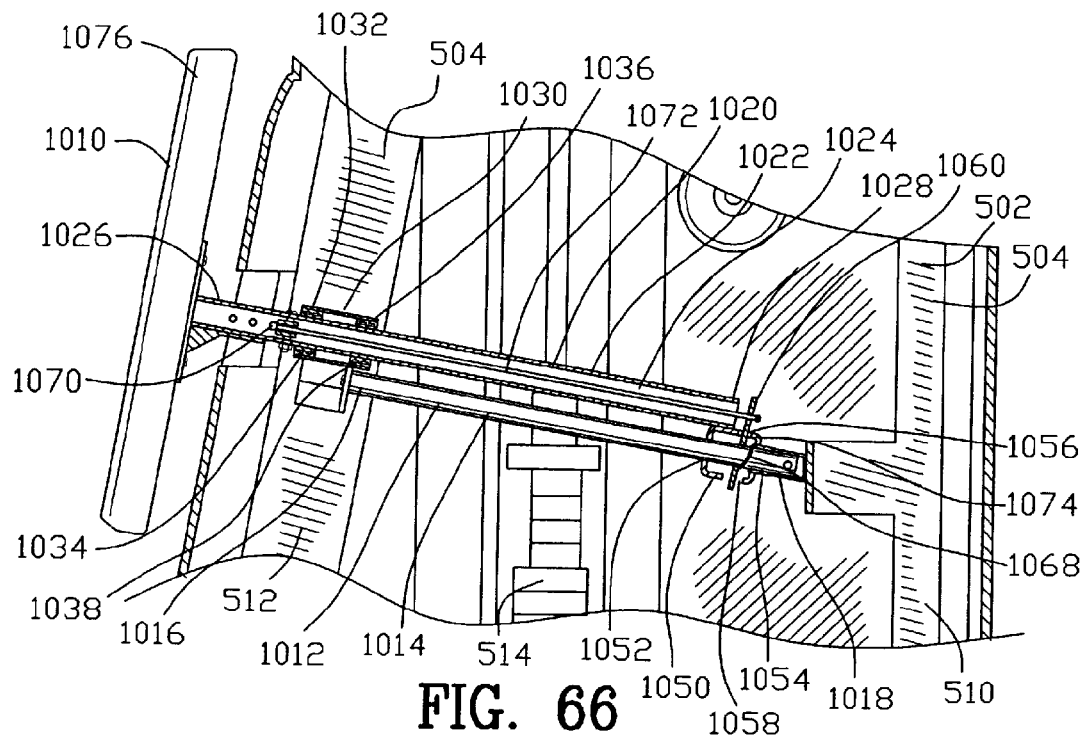
FIG. 66 is a sectional view along line 66-66 in FIG. 65.
Figure 67:
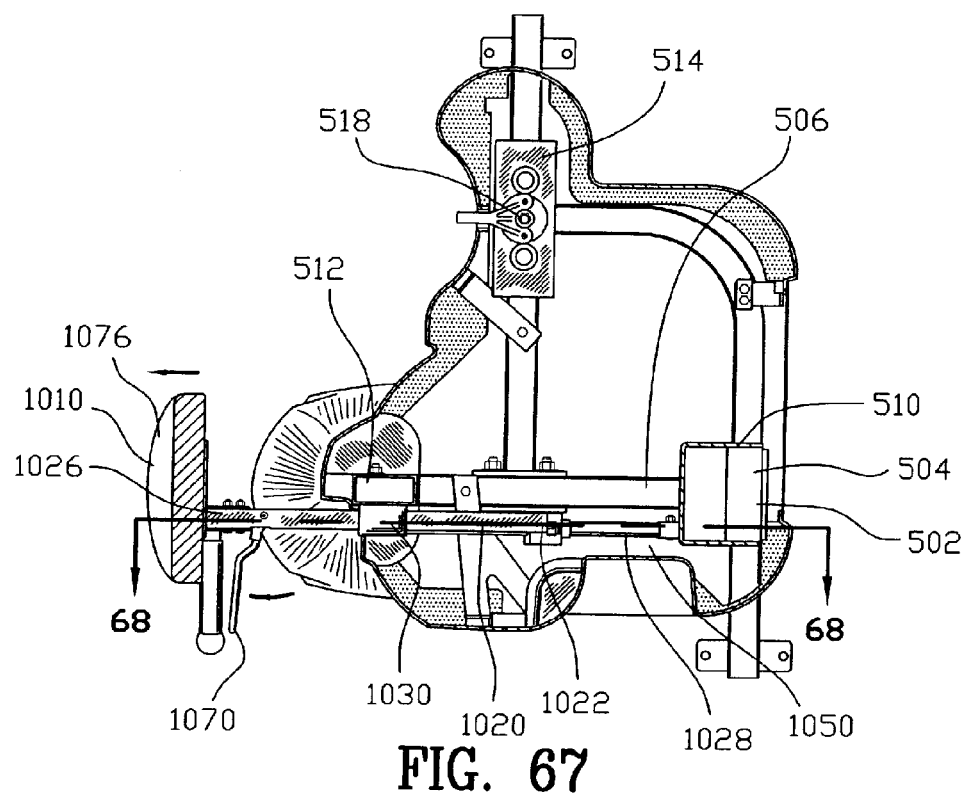
FIG. 67 is a bottom view of FIG. 62.
Figure 68:
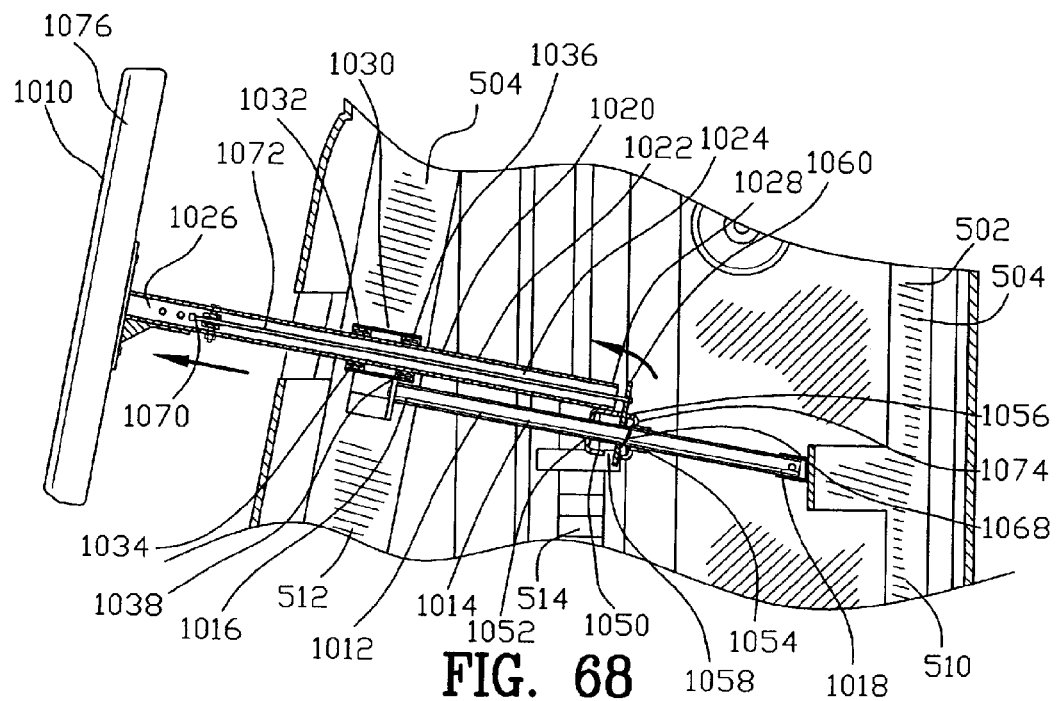
FIG. 68 is a sectional view along line 68-68 in FIG. 67.
Figure 69:
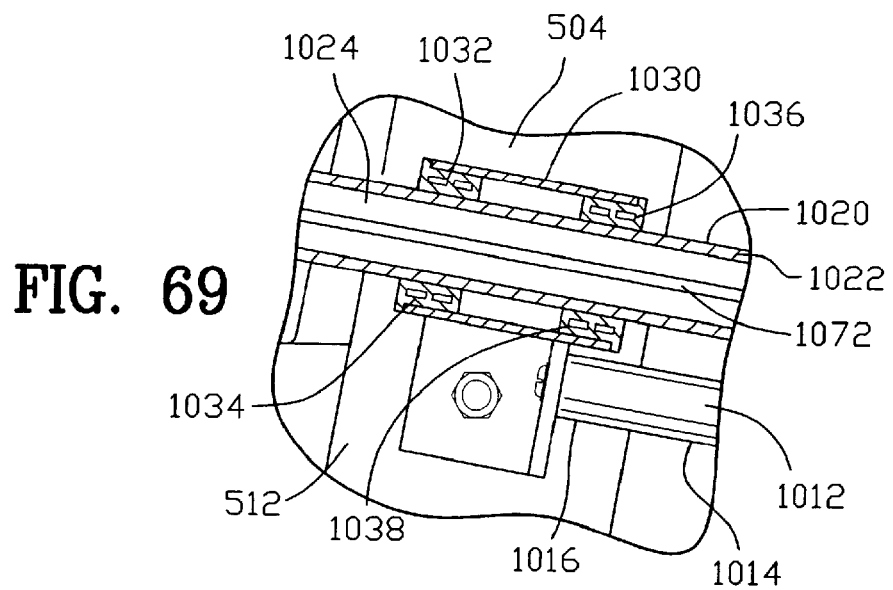
FIG. 69 is a magnified view of a first portion of FIG. 68.
Figure 70:
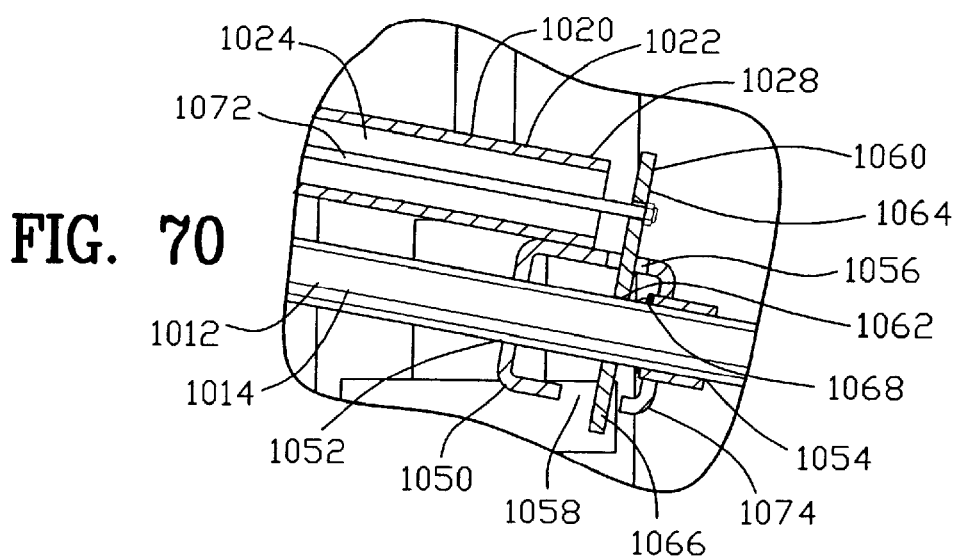
FIG. 70 is a magnified view of a second portion of FIG. 68.
Figure 71:
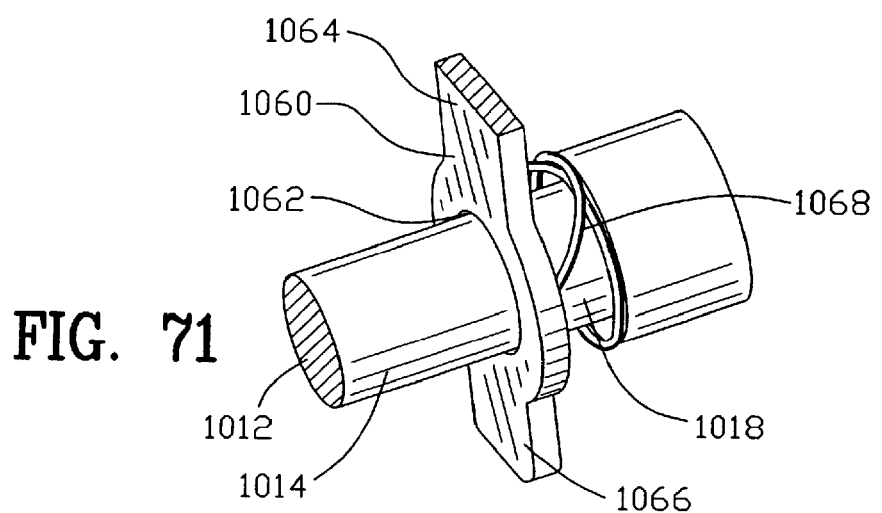
FIG. 71 is an isometric view of a portion of FIG. 70.

As best seen in FIGS. 42-49 and 55-60 a user interface 700 is pivotably secured to the user end 534 of the arm 530 by a user pivot 702. The user pivot 702 pivots the user interface 700 about the user end 534 of the arm 530 for positioning the user interface 700 in multiple positions relative to the arm 530. More specifically, the user pivot 702 may pivot the user interface 700 to a first user interface position 704 as seen in FIG. 42, a second user interface position 706 as seen in FIG. 43, a third user interface position 708 as seen in FIG. 44, a fourth user interface position 710 as seen in FIG. 45, and a fifth user interface position 712 as seen in FIG. 46.

The user interface 700 outputs data and permits the input of data. The data may constitute visual, audio or data inputted by the touch screen display. The data may include updated software, updated firmware, exercise performance, exercise history, custom reports, alerts, service requests and/or advertisements.

The user pivot 702 includes a bushing bearing neck 720 interposed between a pivot head 722 and a pivot base 724. Preferably, the user pivot 702 is constructive of a polymeric material or other rigid material. The pivot head 722 has a cylindrical body 730 defining an interior chamber 732 extends between a first end 734 and a second end 736. The bushing bearing neck 720 has a cylindrical body 740 defining an interior chamber 742 extends between a first end 744 and a second end 746. The pivot base 724 has a cylindrical body 750 defining an interior chamber 752 extends between a first end 754 and a second end 756. Preferably, the pivot head 722, bushing bearing neck 720 and pivot base 724 are an integral one piece unit 758.

The user pivot 702 further includes a first bushing 770 defines a generally C-shape 772 extending between a first end 774 and second end 776 for rotatably engaging the bushing bearing neck 720. The user pivot 702 also includes a second bushing 780 defines a generally C-shape 782 extending between a first end 784 and second end 786 for rotatably engaging the bushing bearing neck 720. The first and second bushings 770 and 780 have an upper slot 790 and a lower slot 792. A first bushing O-ring 794 engages the upper slot 790 of the first bushing 770 and the upper slot 790 of the second bushing 780. A second bushing O-ring 796 engages the lower slot 792 of the first bushing 770 and the lower slot 792 of the second bushing 780. The first and second bushing O-rings 794 and 796 compress when inserted into the interior chamber 536 of the arm 530 for retaining the first and second bushings 770 and 780 firmly against the bushing bearing neck 720 and retaining the first and second O-rings 794 and 796 firmly against the interior chamber 536 of the arm 530.

The bushing bearing neck 720 may further include a neck slot 800 located at the second end 746 of the bushing bearing neck 720. A neck bushing O-ring 802 engages the neck slot 800 for compression between the bushing bearing neck 720 and the first and second bushings 770 and 780. The neck bushing O-ring 802 provides a user interface brake 804 for restricting the rotational speed of the user interface 700.

The first end 774 of the first bushing 770 includes a top block pin 806 extending vertically from the first end 774. The top block pin 806 engages a head groove 808 integral to the second end 736 of the pivot head 722. The head groove 808 has a first block surface 810 and a second block surface 812. Upon rotation of the user interface 700, the top block pin 806 slidably engages the head groove 808 until the top block pin 806 contacts either the first or second block surfaces 810 or 812. Upon the top block pin 806 contacting the first or second block surfaces 810 or 812, the rotation of the user interface 700 will terminate.

The second end 776 of the first bushing 770 includes a bottom block pin 820 extending vertically from the second end 776. The bottom block pin 820 engages a base groove 822 integral to the first end 754 of the pivot base 724. The base groove 822 has a first block surface 824 and a second block surface 826. Upon rotation of the user interface 700, the bottom block pin 820 slidably engages the base groove 822 until the bottom block pin 820 contacts either the first or second block surfaces 824 or 826. Upon the bottom block pin 820 contacting the first or second block surfaces 824 or 826, the rotation of the user interface 700 will terminate. Preferably, the first and second block surfaces 810 and 812 of the head groove 808 are aligned with the first and second block surfaces 824 and 826 of the base groove 822 so that both the top block pin 806 and the bottom block pin 820 simultaneously contact the respective block surfaces.

The pivot base 724 includes a keying mount 840 that is integral to the pivot base 724. The keying mount 840 is received within the user interface 700 to lock the user pivot 702 to the user interface 700. The keying mount 840 may include a first keying mount 842 integral to the pivot base 724 and comprising a first plurality of ribs 844. The keying mount 840 also includes a second keying mount 846 integral to the pivot base 724 and comprising a second plurality of ribs 848. Preferably, the first keying mount 842 and the second keying mount 846 are positioned on opposing sides of the pivot base 724.

The pivot base 724 may further include a plate mount 860 that is integral to the pivot base 724. The plate mount 860 is received within the user interface 700 to lock the user pivot 702 to the user interface 700. The plate mount 860 may include a first plate mount 862 integral to the pivot base 724. The plate mount 860 also includes a second plate mount 864 integral to the pivot base 724. Preferably, the first plate mount 862 and the second plate mount 864 are positioned on opposing sides of the pivot base 724. The first plate mount 862 has a first fastener aperture 866 and the second plate mount 864 has a second fastener aperture 868. Preferably, the keying mount 840 and the plate mount 860 are an integral one piece unit 870.

The user interface 700 includes a base receiver 880 for receiving the pivot base 724 of the user pivot 702. The base receiver 880 includes a keying receiver 882 that is integral to the base receiver 880. The keying receiver 882 receives the pivot base 724 of the user pivot 702 to lock the user pivot 702 to the user interface 700. The keying receiver 882 may include a first keying receiver 884 integral to the base receiver 880 and comprising a first plurality of ribs receptacles 886. The first keying receiver 884 engages the first keying mount 842 of the user pivot 702 to lock the user pivot 702 to the user interface 700. The keying receiver 882 also includes a second keying receiver 888 integral to the base receiver 880 and comprising a contoured receiving surface 890. The second keying receiver 888 engages the second keying mount 846 of the user pivot 702 to lock the user pivot 702 to the user interface 700. Preferably, the first keying receiver 884 and the second keying receiver 888 are positioned on opposing sides of the user interface 700 for alignment of the first keying mount 842 and the second keying mount 846.

The user interface 700 may further include a plate receiver 892 that is integral to the base receiver 880. The plate receiver 892 receives the pivot base 724 to lock the user pivot 702 to the user interface 700. The plate receiver 892 may include a first plate receiver 894 integral to the base receiver 880. The plate receiver 892 also includes a second plate receiver 896 integral to the base receiver 880. Preferably, the first plate receiver 894 and the second plate receiver 896 are positioned on opposing sides of the base receiver 880 for alignment of the first plate mount 862 and the second plate mount 864. The first plate receiver 894 has a first fastener mount 900 and the second plate receiver 896 has a second fastener mount 902. Preferably, the keying receiver 882 and the plate receiver 892 are an integral one piece unit 904.

A first plate fastener 906 traverses through the first fastener aperture 866 of the first plate mount 862 and threadably engages the first fastener mount 900 for securing the plate mount 860 to the plate receiver 892. A second plate fastener 908 traverses through the second fastener aperture 868 of the second plate mount 864 and threadably engages the second fastener mount 902 for securing the plate mount 860 to the plate receiver 892.

The first bushing 770 includes a first fastener passage 910 and the second busing 780 include a second fastener passage 912. The user end 534 of the arm 530 includes a first fastener bore 914 and a second fastener bore 916 positioned on opposing sides of the arm 530. The pivot head 722 and the bushing bearing neck 720 are inserted into the interior chamber 536 of the arm 530 for positioning the first bushing 770 and the second bushing 780 within the arm 530. A first fastener 920 traverses through first fastener bore 914 and into the first fastener passage 910 of the first bushing 770. The first fastener 920 secures the first bushing 770 relative to the arm 530 for rotatably pivoting said user pivot 702 relative to the arm 530. A second fastener 922 traverses through second fastener bore 916 and into the second fastener passage 912 of the second bushing 780. The second fastener 922 secures the second bushing 780 relative to the arm 530 for rotatably pivoting said user pivot 702 relative to the arm 530. Preferably, the first and second fasteners 920 and 922 include a screw that threadably engage a threading core positioned within the first and second fastener passages 910 and 912. Alternatively, the first and second fasteners 920 and 922 may include rivets or other fasteners.

A boot 930 having an interior chamber 932 extends between a first end 934 and a second end 936. The boot 930 extends between the user end 534 of the arm 530 to the user interface 700 to conceal the user pivot 702. The first end 934 of the boot 930 slidably engages the user end 534 of the arm 530 upon rotation of the user interface 700. The second end 936 of the boot 930 includes a boot channel 938 for locking the boot 930 to the user interface 700.

A pivot head cap 940 engages the first end 734 of the pivot head 722 for coupling the electrical conductors 589 traversing from the user interface 700, through the user pivot 702 and out through the arm 530.

FIGS. 61-64 illustrate the apparatus 500 having a seat 950 for supporting a seated operator. The seat 950 includes a first seat support 952 having a cylindrical body 954 that defines an interior chamber 956 extending between a first end 958 and a second end 960. The second end 960 of the first seat support 952 is secured to the base 506. A second seat support 962 includes a cylindrical body 964 that defines an interior chamber 966 extending between a first end 968 and a second end 970. The second end 970 of the second seat support 962 is inserted into the first end 958 of the first seat support 952 for telescoping the second seat support 962 within the interior chamber 956 of the first seat support 952. Preferably, the first and second set support 952 and 962 have a rectangular cross section and are constructed from a metallic material such as steel or aluminum. The seat 950 is secured to the first end 968 of the second seat support 962.

A pneumatic cylinder 972 is interposed between the first end 968 of the second seat support 962 and the base 506 for supporting the seat 950 at multiple positions. The pneumatic cylinder 972 has a shaft 974 that is slidably engaged with a cylinder 976. The shaft 974 is secured to the seat 950 by a seat coupler 978. The cylinder 976 is secured to the base 506 by a base coupler 980. The shaft 974 includes a valve actuator 982 for operating the pneumatic cylinder 972. The valve actuator 982 is positioned within the seat coupler 978. A seat actuator 984 is pivotably secured to the seat 950 by a seat actuator mount 986. A seat actuator linkage 988 is interposed between the seat actuator 984 and the seat coupler 978 for conveying a displacement of the seat actuator 984 to displace the valve actuator 982. The seat actuator 984 is utilized by the operator to control the pneumatic cylinder 972. The pneumatic cylinder 972 adjusts the vertical level of the seat 950. The pneumatic cylinder 972 may include a single acting pneumatic cylinder 990, double acting pneumatic cylinder 992 or other pneumatic cylinder 990. The pneumatic cylinder 972 may have a mechanical lock 994 for locking the shaft 974 relative to the cylinder 976 during the operator utilizing the pneumatic cylinder 972. The mechanical lock 994 also serves as a safety mechanism in case of air supply lost or a reduction in pressure within the pneumatic cylinder 972.

The first end 958 of the first seat support 952 may include a first seat bushing 1000 and a second seat bushing 1002 positioned on opposing sides of the first seat support 952. The first seat bushing 1000 and a second seat bushing 1002 slidably engage the second seat support 962 for guiding the telescoping engagement between the second seat support 962 within the interior chamber 956 of the first seat support 952. The first seat bushing 1000 and a second seat bushing 1002 may be constructed from polymeric material or other rigid material.

The second end 970 of the second seat support 962 may include a first seat bushing 1004 and a second seat bushing 1006 positioned on opposing sides of said second seat support 962. The first seat bushing 1004 and a second seat bushing 1006 slidably engage the first 952 for guiding the telescoping engagement between the second seat support 962 within the interior chamber 956 of the first seat support 952. The first seat bushing 1004 and a second seat bushing 1006 may be constructed from polymeric material or other rigid material.

FIGS. 61, 62 and 65-71 illustrate the apparatus 500 having a backseat support device 1010 for supporting the back of an operator. The backset 1010 includes a first backseat support 1012 having a cylindrical body 1014 extending between a first end 1016 and a second end 1018. The second end 1018 of the first backseat support 1012 is secured to the first frame coupling 510. The first end 1016 of the first backseat support 1012 is secured to the second frame coupling 512. Preferably, the first backseat support 1012 is constructed from a of metallic material such as steel or aluminum.

A second backseat support 1020 having a cylindrical body 1022 defining an interior chamber 1024 extending between a first end 1026 and a second end 1028. Preferably, the second backseat support 1020 is constructed from a cylindrical square stock of metallic material such as steel or aluminum.

A first backseat guide 1030 is secured to the second frame coupling 512 for slidably engaging the cylindrical body 1022 of the second backseat support 1020. Preferably, the first backseat guide 1030 is constructed from a cylindrical square stock of metallic material such as steel or aluminum such that second backseat support 1020 may slidably engage within the first backseat guide 1030. The first backseat guide 1030 may further include a first backseat bushing 1032 and a second backseat bushing 1034 positioned on opposing sides of the first backseat guide 1030. An additional third backseat bushing 1036 and a fourth backseat bushing 1038 may be also positioned on opposing sides of the first backseat guide 1030. The first, second, third and fourth backseat bushings 1032, 1034, 1036, and 1038 slidably engage second backseat support 1020 for guiding the slidable engagement between the second backseat support 1020 within the first backseat guide 1030. The first, second, third and fourth backseat bushings 1032, 1034, 1036, and 1038 may be constructed from polymeric material or other rigid material.

A second backseat guide 1050 is secured to the second end 1028 of the second backseat support 1020 for slidably engaging the cylindrical body 1014 of the first backseat support 1012. The second backseat guide 1050 includes a first slide aperture 1052 that is aligned with a second slide aperture 1054. The first and second slide apertures 1052 and 1054 slidably engage the cylindrical body 1014 of the first backseat support 1012. The second backseat guide 1050 further includes a first plate aperture 1056 aligned with a second plate aperture 1058. The alignment of the first and second slide apertures 1052 and 1054 is generally perpendicular to the alignment of the first and second plate apertures 1056 and 1058.

A locking plate 1060 pivotably engages the second backseat guide 1050 and slidably engaging the cylindrical body 1014 of the first backseat support 1012 for locking the second backseat guide 1050 relative to the first backseat support 1012. The locking plate 1060 includes a plate slide aperture 1062 for slidably engaging the cylindrical body 1014 of the first backseat support 1012. The locking plate 1060 further includes a first tab 1064 and a second tab 1066 for inserting into the first plate aperture 1056 and the second plate aperture 1058 respectively. A backseat spring 1068 is interposed between the first backseat support 1012 and the locking plate 1060 for biasing the plate slide aperture 1062 wedged against the first backseat support 1012 for terminating movement of the second backseat guide 1050 relative to the first backseat support 1012.

A backseat actuator 1070 is pivotably secured to the first end 1026 of the second backseat support 1020 to engage and disengage the locking plate 1060 from the first backseat support 1012. A backseat actuator linkage 1072 is positioned within the interior chamber 1024 of the second backseat support 1020 and interposed between the backseat actuator 1070 and the first tab 1064 of the locking plate 1060 for conveying a displacement of the backseat actuator 1070 to a displacement of the locking plate 1060. Displacement of the backseat actuator 1070 in the direction of the first end 1026 of the second backseat support 1020 overcomes the biasing force of the backseat spring 1068 to displace the locking plate 1060 from a generally non-perpendicular position relative to the first backseat support 1012. More specifically, the displacement of the backseat actuator 1070 in the direction of the first end 1026 of the second backseat support 1020 displaces the locking plate 1060 from a generally non-perpendicular position relative to the first backseat support 1012 to a generally perpendicular position relative to the first backseat support 1012. Where the locking plate 1060 is in a generally perpendicular position relative to the first backseat support 1012, the wedge between the second backseat guide 1050 and the locking plate 1060 against the first backseat support 1012 is removed allowing the second backseat support 1020 to slidably engage within the first backseat guide 1030.

Upon the release of the displacement of the backseat actuator 1070, the backseat spring 1068 causes the locking plate 1060 to revert back to a generally non-perpendicular position relative to the first backseat support 1012 for creating a wedge camp 1074 between the second backseat guide 1050 and the locking plate 1060 against the first backseat support 1012.

A backseat 1076 is secured to the first end 1026 of the second backseat support 1020 for supporting the backside of the operator. By utilizing the backseat actuator 1070 to engage and disengage the wedge camp 1074, the backseat may be positioned in multiple positions.

The present disclosure includes that contained in the appended claims as well as that of the foregoing description. Although this invention has been described in its preferred form with a certain degree of particularity, it is understood that the present disclosure of the preferred form has been made only by way of example and that numerous changes in the details of construction and the combination and arrangement of parts may be resorted to without departing from the spirit and scope of the invention.

What is claimed is:

1. An apparatus for enabling an operator to exercise, comprising:
    a frame having a body portion, a base portion and an upper portion;
    a load positioned on said frame to provide a resistive force;
    a press positioned on said frame for displacement by the operator;
    a linkage joining said load with said press for displacing said load upon displacement of said press by the operator;
    an arm having first and second ends;
    a support pivot securing said first end of said arm to said upper portion of said frame for rotating said arm about said upper portion of said frame;
    a user interface device to input and output data; and
    a pivot securing said user interface to said second end of said arm to pivot said user interface about said second end of said arm.

2. An apparatus for enabling an operator to exercise as set forth in claim 1, wherein said support pivot securing said first end of said arm to said frame permits a portion of said arm secured to the frame to rotate in a horizontal plane with respect to said frame.

3. An apparatus for enabling an operator to exercise as set forth in claim 1, wherein said support pivot has a cylindrical interior chamber extending between a first end and a second end, the apparatus further comprising:
    a pin receiver defining a pin receiver interior chamber secured within said interior chamber of said cylindrical body; and a pin traversing through said top of said frame and through said pin receiver interior chamber to pivotably mount said support pivot to said top of said frame.

4. An apparatus for enabling an operator to exercise as set forth in claim 1, wherein said support pivot has a cylindrical an interior chamber extending between a first end and a second end, the apparatus further comprising:
- a pin receiver defining a pin receiver interior chamber extending between a first pin receiver end and a second pin receiver end and secured within said interior chamber of said cylindrical body;
- a first bearing positioned within said first pin receiver end; and
- a second bearing positioned within said second pin receiver end; and
- a pin traversing through said top of said frame and through said second bearing and said first bearing of said pin receiver to pivotably mount said support pivot to said top of said frame.

5. An apparatus for enabling an operator to exercise as set forth in claim 1, wherein said support pivot has a cylindrical an interior chamber extending between a first end and a second end, the apparatus further comprising:
- a pin receiver defining a pin receiver interior chamber extending between a first pin receiver end and a second pin receiver end and secured within said interior chamber of said cylindrical body;
- a first support plate positioned at said first pin receiver end and extending between said pin receiver and said support pivot for securing said pin receiver within said interior chamber of said cylindrical body;
- a second support plate positioned at said second pin receiver end and extending between said pin receiver and said support pivot for securing said pin receiver within said interior chamber of said cylindrical body; and
- a pin traversing through said top of said frame and through said pin receiver interior chamber to pivotably mount said support pivot to said top of said frame.

6. An apparatus for enabling an operator to exercise as set forth in claim 1, wherein said support pivot has a cylindrical an interior chamber extending between a first end and a second end, the apparatus further comprising:
- a pin traversing through said top of said frame and through said interior chamber of said support pivot to pivotably mount said support pivot to said top of said frame;
- a stop plate extending from said second end of said cylindrical body; and
- a stop pin extending from said top of said frame for contacting said stop plate for terminating rotation of said arm.

7. An apparatus for enabling an operator to exercise as set forth in claim 1, wherein said support pivot has a cylindrical an interior chamber extending between a first end and a second end, the apparatus further comprising:
- a pin traversing through said top of said frame and through said interior chamber of said support pivot to pivotably mount said support pivot to said top of said frame;
- a first stop surface extending from said second end of said cylindrical body;
- a second stop surface extending from said second end of said cylindrical body; and
- a stop pin extending from said top of said frame for contacting said first stop surface for terminating rotation of said arm in a first arm position and contacting said second stop surface for terminating rotation of said arm in a second arm position.

8. An apparatus for enabling an operator to exercise as set forth in claim 1, wherein said support pivot has a cylindrical an interior chamber extending between a first end and a second end, apparatus further comprising:
- a pin traversing through said top of said frame and through said interior chamber of said support pivot to pivotably mount said support pivot to said top of said frame;
- a brake plate extending from said second end of said cylindrical body; and
- a brake extending from said top of said frame for contacting said brake plate for restricting the rotational speed of said arm.

9. An apparatus for enabling an operator to exercise as set forth in claim 1, wherein the user interface further comprises:
- a display device to render instructions to the user; and
- a computing device disposed in the display device to generate instructions to the user.

10. An apparatus for enabling an operator to exercise as set forth in claim 9, wherein the display device is a touch screen display device to render instructions to the user and to input data from the user.

11. An apparatus for enabling an operator to exercise as set forth in claim 1, wherein said arm has a cylindrical arm body defining a generally L-shape; and said arm includes an arm interior chamber extending between a first arm end and a second arm end; and said pivot includes:
- a bushing bearing neck interposed between a pivot head and a pivot base;
the apparatus further comprising:
- a first bushing and a second bushing rotatably engaging said bushing bearing neck;
- a base receiver positioned within said user interface for receiving said pivot base of said pivot.

12. An apparatus for enabling an operator to exercise as set forth in claim 1, wherein:
- said arm includes an arm interior chamber extending from said second end;
- said pivot includes:
- a bushing bearing neck interposed between a pivot head and a pivot base; and
- said pivot head includes a cylindrical pivot head body defining a pivot head interior chamber extending between a first pivot head end and a second pivot head end;
- a first bushing having a generally C-shape extending between a first end and second end for rotatably engaging said bushing bearing neck;
- a second bushing having a generally C-shape end for rotatably engaging said bushing bearing neck; and
- a base receiver positioned within said user interface for receiving said pivot base of said pivot.

13. An apparatus for enabling an operator to exercise as set forth in claim 12, the apparatus further comprising:
- a keying receiver integral to said base receiver;
- a keying mount integral to said pivot base for engaging said keying receiver to lock said pivot to said user interface.

14. An apparatus for enabling an operator to exercise as set forth in claim 1, wherein:
- said arm includes an arm interior chamber extending from said user end; and
- said pivot includes a bushing bearing neck interposed between a pivot head and a pivot base:
the apparatus further comprising:
- a first bushing and a second bushing rotatably engaging said bushing bearing neck;
- a base receiver positioned within said user interface for receiving said pivot base of said pivot;

a plate receiver integral to said base receiver;
a plate mount integral to said pivot base for engaging said plate receiver;
a plate fastener securing said plate mount to said plate receiver to lock said pivot to said user interface;
said pivot head and said bushing bearing neck inserted into said arm interior chamber for positioning said first bushing and said second hushing within said arm;
a first fastener securing said first bushing relative to said arm for rotatably pivoting said pivot relative to said arm; and
a second fastener securing said second bushing relative to said arm for rotatably pivoting said pivot relative to said arm.

15. An apparatus for enabling an operator to exercise as set forth in claim 1, wherein:
said arm includes an arm interior chamber extending from said user end; and
said pivot includes a bushing bearing neck interposed between a pivot head and a pivot base;
the apparatus further comprising:
a first bushing and a second bushing rotatably engaging said bushing bearing neck;
an upper slot and a lower slot positioned on said first bushing;
an upper slot and a lower slot positioned on said second bushing;
a first bushing O-ring engaging said upper slot of said first bushing and said upper slot of said second bushing for compression against said arm interior chamber;
a second bushing O-ring engaging said lower slot of said first bushing and said lower slot of said second bushing for compression against said arm interior chamber;
a base receiver positioned within said user interface for receiving said pivot base of said pivot;
a keying receiver integral to said base receiver;
a keying mount integral to said pivot base for engaging said keying receiver to lock said pivot to said user interface;
said pivot head and said bushing bearing neck inserted into said arm interior chamber for positioning said first bushing and said second bushing within said arm;
a first fastener securing said first bushing relative to said arm for rotatably pivoting said pivot relative to said arm; and
a second fastener securing said second bushing relative to said arm for rotatably pivoting said pivot relative to said arm.

16. An exercise apparatus, comprising:
a frame having a body, a base portion and a top portion;
a load supported by the body portion of the frame to provide a resistive force;
a press supported on the frame for displacement by an operator;
a linkage joining the load with the press for displacing the load upon displacement of the press by the operator;
an arm member having a first end rotatably coupled to the top portion of the frame to permit the arm to rotate in a horizontal plane about the frame; and
an electronic device to input data and to output data, the electronic device rotatably coupled to a second end of the arm member.

17. The exercise apparatus of claim 16, wherein the electronic device comprises a liquid crystal touch screen display for presenting visual data.

18. The exercise apparatus of claim 16 wherein the electronic device includes an input port for receiving a memory storage device of receiving data.

19. The exercise apparatus of claim 16 wherein the electronic device includes one or more speaker units to provide audible feedback to the operator.

20. The exercise apparatus of claim 16, further comprising:
a seat support;
a seat secured to the seat support.

21. The exercise apparatus of claim 16 wherein the arm member defines a generally L-shape.

22. The exercise apparatus of claim 16 further comprising a sensor to measure displacement of the press support that feeds a signal related to the displacement to the electronic device.

23. The exercise apparatus of claim 16 comprising a support pivot for attaching the arm member to the top portion of the frame.

24. The exercise apparatus of claim 16 wherein the arm member is configured to pivot about the frame to position the electronic device coupled to the second end of the arm member at multiple positions relative to the apparatus.

25. The exercise apparatus of claim 16 further comprising a stop pin for terminating a movement of the arm about the frame.

26. The exercise apparatus of claim 16 further comprising a brake for restricting a rotational speed of the electronic device about the frame.

27. The exercise apparatus of claim 16 wherein the electronic device comprises a user interface for instructing the operator of the apparatus through an interactive exercise program.

* * * * *